United States Patent
Kranz et al.

(10) Patent No.: US 10,464,987 B2
(45) Date of Patent: Nov. 5, 2019

(54) HUMAN SINGLE-CHAIN T CELL RECEPTORS

(75) Inventors: David M. Kranz, Champaign, IL (US); David H. Aggen, Savoy, IL (US)

(73) Assignee: AbbVie Inc., Chicago, IL (US)

( * ) Notice: Subject to any disclaimer, the term of this patent is extended or adjusted under 35 U.S.C. 154(b) by 0 days.

(21) Appl. No.: 13/500,123

(22) PCT Filed: Oct. 6, 2010

(86) PCT No.: PCT/US2010/051559
§ 371 (c)(1),
(2), (4) Date: Jun. 11, 2012

(87) PCT Pub. No.: WO2011/044186
PCT Pub. Date: Apr. 14, 2011

(65) Prior Publication Data
US 2012/0252742 A1    Oct. 4, 2012

Related U.S. Application Data

(60) Provisional application No. 61/248,924, filed on Oct. 6, 2009.

(51) Int. Cl.
*C07K 14/705* (2006.01)
*C07K 14/725* (2006.01)

(52) U.S. Cl.
CPC .................. *C07K 14/7051* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,927,193 A | 12/1975 | Hansen et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,331,647 A | 5/1982 | Goldenberg |
| 4,348,376 A | 9/1982 | Goldenberg |
| 4,361,544 A | 11/1982 | Goldenberg |
| 4,366,241 A | 12/1982 | Tom et al. |
| 4,444,744 A | 4/1984 | Goldenberg |
| 4,640,561 A | 2/1987 | George |
| 5,059,413 A | 10/1991 | Reardan et al. |
| 5,101,827 A | 4/1992 | Goldenberg |
| 5,299,253 A | 3/1994 | Wessels |
| RE35,500 E | 5/1997 | Rhodes |
| 6,121,034 A | 9/2000 | Laroche et al. |
| 6,759,243 B2 | 7/2004 | Kranz et al. |
| 7,456,263 B2 | 11/2008 | Sherman et al. |
| 7,462,486 B2 | 12/2008 | Vandenbark |
| 7,569,664 B2 | 8/2009 | Jakobsen et al. |
| 6,759,243 C1 | 5/2014 | Kranz et al. |
| 6,759,243 C2 | 9/2015 | Kranz et al. |
| 2003/0144474 A1 | 7/2003 | Weidanz et al. |
| 2006/0166875 A1 | 7/2006 | Jakobsen et al. |
| 2007/0116718 A1 | 5/2007 | Weidanz et al. |
| 2009/0208502 A1 | 8/2009 | Willemsen |

FOREIGN PATENT DOCUMENTS

| | | |
|---|---|---|
| EP | 0137457 B1 | 3/1988 |
| WO | WO-1999/36569 | 7/1999 |
| WO | WO 2006103429 A2 * | 10/2006 |

OTHER PUBLICATIONS

Richman, Sarah A. et al; "Structural features of T-cell receptor variable regions that enhance domain stability and enable expression as single chain ValphaVbeta fragments". Mol. Immun; (2009) 46(5) p. 902-916.*

Perlin, Lynne et al; "Production and perfomrance of biomaterials containing RGD peptides." Soft Matter (2008) 4 p. 2331-2349.*

Ding, Yuan-Hua et al, "Two human t cell receptors bind in a similar diagonal mode to the hla-a2/tax peptide complex using different to amino acids." Immunity (1998) 8 p. 403-411.*

The peptide sequence for chain D of human A6-TCR, peptide database accession No. 1QSE_D, submitted Jun. 21, 1999.*

Utz, Ursula et al, "Analysis of the t-cell receptor repertoire of human t-cell leukemia virus type 1(htlv-1) tax specific cd8+ cytotoxic t lymphocytes from patients with htlv-1 associated disease: evidence for oligoclonal expansion." J. Virol. (1996) 70(2) p. 843-851.*

Soo Hoo, William F. et al, "Characterization of a single-chain t-cell receptor expressed in *Escerichia coli*." Proc. Natl. Acad. Sci. USA (1992) 89 p. 4759-4763.*

Anikeeva et al., Can oligomeric T-cell receptor be used as a tool to detect viral peptide epitopes on infected cells?, Clinical Immunology, 2009, 98-109, 130.

Boder et al., Yeast Surface Display for Directed Evolution of Protein Expression, Affinity, and Stability, Methods in Enzymology, 2000, 430-444, 328.

Boulter et al., Stable, soluble T cell receptor molecules for crystallization and therapeutics, Protein Engineering, 2003, 707-711, 16(9).

Carpenito et al., Control of large, established tumor xenografts with genetically retargeted human T cells containing CD28 and DC 137 domains, PNAS, Mar. 3, 2009, 3360-3365, 106(9).

Chatal et al., Clinical Prospective Study with Radioiodinated Monoclonal Antibodies Directed against Colorectal Cancer, Chapter 8, Monoclonal Antibodies for Cancer Detection and Therapy, Academic Press, San Diego, 1985, 159-179.

(Continued)

*Primary Examiner* — Fred H Reynolds
(74) *Attorney, Agent, or Firm* — Womble Bond Dickson (US) LLP; Cristin H. Cowles; Kevin A. Fiala

(57) ABSTRACT

A soluble human single-chain T cell receptor (TCR) having the structure: Vα2-L-Vβ or Vβ-L-Vα2, wherein L is a linker peptide that links Vβ with Vα, Vβ is a TCR variable β region, and Vα2 is a TCR variable α region of the family 2 is provided. The provided scTCR is useful for many purposes, including the treatment of cancer, viral diseases and autoimmune diseases.

18 Claims, 28 Drawing Sheets
Specification includes a Sequence Listing.

(56) References Cited

OTHER PUBLICATIONS

Chervin et al., The Impact of TCR-Binding Properties and Antigen Presentation Format on T Cell Responsiveness, The Journal of Immunology, 2009, 1166-1178, 183.
Cohen et al., Enhanced Antitumor Activity of T Cells Engineered to Express T-Cell Receptors with a Second Disulfide Bond, Cancer Research, 2007, 3898-3903, 678.
Correia-Neves et al., Amino Acids Specifying MHC Class Preference in TCR V alpha2 Regions, The Journal of Immunology, 1999, 5471-5477, 163.
De Witte et al., Requirements for Effective Antitumor Responses of TCR Transduced T Cells, The Journal of Immunology, 2008, 5128-5136, 181.
Dietrich et al., Prevalent Role of TCR alpha-Chain in the Selection of the Preimmune Repertoire Specific for a Human Tumor-Associated Self-Antigen, The Journal of Immunology, 2003, 5103-5109, 170.
Dossett et al., Adoptive Immunotherapy of Disseminated Leukemia With TCR-transduced, CD8+ T Cells Expressing Known Endogenous TCR, Molecular Therapy, 2009, 742-749, 17(4).
Dunn et al., Directed evolution of human T cell receptor CDR2 residues by phage display dramatically enhances affinity for cognate peptide-MHC without increasing apparent cross-reactivity, Protein Science.org, 2006, 710-721, 15.
Garboczi et al., Structure of the complex between human T-cell receptor, viral peptide and HLA-A2, Nature, 1996, 134-141, 384.
Garcia et al., Kinetics and thermodynamics of T cell receptor-autoantigen interactions in murine experimental autoimmune encephalomyelitis, PNAS, Jun. 5, 2001, 6818-6823, 98(12).
Hart et al., Retroviral transfer of a dominant TCR prevents surface expression of a large proportion of the endogenous TCR repertoire in human T cells, Gene Therapy, 2008, 625-631, 15.
Heemskerk et al., Efficiency of T-Cell receptor expression in dual-specific T cells is controlled by the intrinsic qualities of the TCR chains within the TCR-CD3 complex, Blood, 2007, 235-243, 109.
Hilyard et al., Binding of soluble natural ligands to a soluble human T-cell receptor fragment produced in *Escherichia coli*, Proc. Natl. Acad. Sci. USA, 1994, 9057-9061, 91.
Holler et al., TCRs with high affinity for foreign pMHC show self-reactivity, Nature Immunology, Jan. 2003, 55-62, 4(1).
Holler et al., In vitro evolution of a T cell receptor with high affinity for peptide/MHC, PNAS, May 9, 2000, 5387-5392, 97(10).
Jones et al., Engineering and Characterization of a Stabilized alpha1/alpha2 Module of the Class I Major Histocompatibility Complex Product Ld, Journal of Biological Chemistry, 2006, 25734-25744, 281.
Kieke et al., Selection of functional T cell receptor mutants from a yeast surface-display library, Proc. Natl. Acad. Sci. USA, 1999, 5651-5656, 96.
Kochenderfer et al., Construction and Preclinical Evaluation of an Anti-CD19 Chimeric Antigen Receptor, J. Immunotherapy, 2009, 689-702, 32(7).
Kuball et al, Facilitating matched pairing and expression of TCR chains introduced into human T cells, Blood by American Society of Hematology, 2007, 2331-2338, 109.
Li et al., Directed evolution of human T-cell receptors with picomolar affinities by phage display, Nature Biotechnology, 2005, 349-354, 23(3).
Mantovani et al., Dominant TCR-alpha Requirements for a Self Antigen Recognition in Humans, The Journal of Immunology, 2002, 6253-6260, 169.
Martinez-Hackert et al., Protein Structure and Folding: Structural Basis for Degenerate Recognition of Natural HIV Peptide Variants by Cytotoxic Lymphocytes, The Journal of Biological Chemistry, 2006, 20205-20212, 281.
Milone et al., Chimeric Receptors Containing CD137 Signal Transduction Domains Mediate Enhanced Survival of T Cells and Increased Antileukemic Efficacy in Vivo, Molecular Therapy, 2009, 1453-1464, 17(8).

Novotny et al., A soluble, single-chain T-cell receptor fragment endowed with antigen-combining properties, Proc. Natl. Acad. Sci. USA, Oct. 1991, 8646-8650, 88.
Olsnes et al., Chimeric Toxins, Pharmac. Ther., 1982, 355-381, 15.
Park et al., Limitations of yeast surface display in engineering proteins of high thermostability, Protein Engineering, Design & Selection, 2006, 211-217, 19(5).
Richman et al., Display, engineering, and applications of antigen-specific T cell receptors, Elsevier/Biomolecular Engineering, 2007, 361-373, 24.
Richman et al., Biosensor Detection Systems: Engineering Stable, High-Affinity Bioreceptors by Yeast Surface Display, Chapter 19, Methods in Molecular Biology: Biosensors and Biodetection, 2009, 323-350, 504.
Richman et al., Structural features of T cell receptor variable regions that enhance domain stability and enable expression as single-chain ValphaVbeta fragments, Molecular Immunology, 2009, 902-916, 46.
Rudolph et al., How TCRs Bind MHCs, Peptides, and Coreceptors, Annu. Rev. Immunol, 2006, 419-466, 24.
Sadelain et al., The promise and potential pitfalls of chimeric antigen receptors, Current Opinion in Immunology, 2009, 215-223, 21.
Sami et al., Crystal structures of high affinity human T-Cell receptors bound to peptide major histocompatibility complex reveal native diagonal binding geometry, Protein Engineering, Design & Selection, 2007, 397-403, 20(8).
Schmitt et al., T Cell Receptor Gene Therapy for Cancer, Human Gene Therapy, 2009, 1240-1248, 20.
Shusta et al., Yeast Polypeptide Fusion Surface Display Levels Predict Thermal Stability and Soluble Secretion Efficiency, 1999, 949-956, 292.
Shusta et al., Directed evolution of a stable scaffold for T-cell receptor engineering, Nature Biotechnology, 2000, 754-759, 18.
Sommermeyer et al., Designer T cells by T cell receptor replacement, European Journal of Immunology, 2006, 3052-3059, 36.
Soo Hoo et al., Characterization of a single-chain T-cell receptor expressed in *Escherichia coli*, Proc. Natl. Acad. Sci. USA, 1992, 4759-4763, 89.
Starr et al., Positive and Negative Selection of T Cells, Annu. Rev. Immunol, 2003, 139-176, 21.
Stone et al., T-cell receptor binding affinities and kinetics: impact on T-cell activity and specificity, Immunology, 2009, 165-176, 126.
Tammana et al., 4-1BB and CD28 Signaling Plays a Synergistic Role in Redirecting Umbilical Cord Blood T Cells Against B-Cell Malignancies, Human Gene Therapy, 2010, 75-86, 21.
Turnbull et al., HIV-1 Epitope-Specific CD8+ T Cell Responses Strongly Associated with Delayed Disease Progression Cross-Recognize Epitope Variants Efficiently, The Journal of Immunology, 2006, 6130-6146, 176.
Warrens et al., Splicing by overlap extension by PCR using asymmetric amplification: an improved technique for the generation of hybrid proteins of immunological interest, Gene, 1997, 29-35, 186.
Weber et al., Class II-restricted T cell receptor engineered in vitro for higher affinity retains peptide specificity and function, PNAS, 2005, 19033-19038, 102(52).
Varela-Rohena et al., Control of HIV-1 immune escape by CD8 T cells expressing enhanced T-cell receptor, Nature Medicine, 2008, 1390-1395, 14(12).
Zhang et al., Transgenic TCR expression: comparison of single chain with full-length receptor constructs for T-cell function, Cancer Gene Therapy, 2004, 487-496, 11.
Zhang et al., Equilibrium between Host and Cancer Caused by Effector T Cells Killing Tumor Stroma, Cancer Research, 2008, 1563-1571, 68.
Alberti S., A high affinity T cell receptor?, Immunol. Cell. Biol. 74(3): 292-7 (1996).
Cho B.K. et al., Characterization of a single-chain antibody to the beta-chain of the T cell receptor, J. Biol. Chem. 270(43) :25819-26 (1995).
Corr M. et al., T cell receptor-MHC class I peptide interactions: affinity, kinetics and specificity, Science 265(5174): 946-9 (1994).

(56) References Cited

OTHER PUBLICATIONS

Grégoire C. et al., Covalent assembly of a soluble T cell receptor-peptide-major histocompatibility class I complex, *Proc. Natl. Acad. Sci. USA* 93(14): 7184-9 (1996).
Manning T.C. et al., Alanine scanning mutagenesis of an αβ T cell receptor: Mapping the energy of antigen recognition, *Immunity* 8(4): 413-25 (1998).
Manning T.C. et al., Effects of complementarity determining region mutations on the affinity of an α/β T cell receptor: Measuring the energy associated with CD4/CD8 repertoire skewing, *J. Exp. Med.* 189(3): 461-70 (1999).
Schlueter C.J. et al., A residue in the center of peptide QL9 affects binding to both Ld and the T cell receptor, *J. Immunol.* 157(10): 4478-85 (1996).
Schlueter C.J. et al., Specificity and binding properties of a single-chain T cell receptor, *J. Mol. Biol.* 256(5): 859-69 (1996).
Williamson M.P., The structure and function of proline-rich regions in proteins, *Biochem. J.* 297: 249-60 (1994).
Arden et al., Human T-cell receptor variable gene segment families, Immunogenetics 42:455-500 (1995).
Arden et al., Mouse T-cell receptor variable gene segment families, Immunogenetics 42:501-530 (1995).
Bosc et al., The Mouse (*Mus musculus*) T Cell Receptor Beta Variable (TRBV), Diversity (TRBD) and Joining (TRBJ) Genes, Exp. Clin. Immunogenet 17:216-228 (2000).
Bosc et al., The mouse (*Mus musculus*) T cell receptor alpha (TRA) and delta (TRD) variable genes, Developmental and Comparative Immunology 27:465-497 (2003).
Clark et al., Comparison of human and mouse T-cell receptor variable gene segment subfamilies, Immunogenetics 42:531-540 (1995).
Folch et al., The Human T cell Receptor Beta Variable (TRBV) Genes, Exp. Clin. Immunogenet 17:42-54 (2000).
Scaviner et al., The Human T Cell Receptor Alpha Variable (TRAV) Genes, Exp. Clin. Immunogenet 17:83-96 (2000).

Aggen et al., Identification and engineering of human variable regions that allow expression of stable single-chain T cell receptors, Protein Eng. Des. Sel. 24(4):361-372 (2011).
Arstila et al., A Direct Estimate of the Human αβ T Cell Receptor Diversity, Science 286(5441):958-961 (1999).
Chang et al., A general method for facilitating heterodimeric pairing between two proteins: Application to expression of α and β T-cell receptor extracellular segments, Proc. Natl. Acad. Sci. USA 91:11408-11412 (1994).
Chung et al., Functional three-domain single-chain T-cell receptors, Proc. Natl. Acad. Sci. USA 91:12654-12658 (1994).
Embleton et al., In-cell PCR from mRNA: amplifying and linking the rearranged immunoglobulin heavy and light chain V-genes within single cells, Nucleic Acids Res. (20(15):3831-3837 (1992).
Freeman et al., Profiling the T-cell receptor beta-chain repertoire by massively parallel sequencing, Genome Res. 19(10):1817-1824 (2009).
Gunnarsen et al., Periplasmic expression of soluble single chain T cell receptors is rescued by the chaperone FkpA, BMC Biotechnol. 10(8):1-13 (2010).
Kurucz et al., A bacterially expressed single-chain Fv construct from the 2B4 T-cell receptor, Proc. Natl. Acad. Sci. USA 90:3830-3834 (1993).
McKeever et al.,Immunization with soluble BDC 2.5 T cell receptor-immunoglobulin chimeric protein:antibody specificity and protection of nonobese diabetic mice against adoptive transfer of diabetes by maternal immunization, J. Exp. Med. 184(5):1755-1768 (1996).
Plaksin et al., A T cell receptor V alpha domain expressed in bacteria: does it dimerize in solution?, J. Exp. Med. 184(4):1251-1258 (1996).
Robins et al., Comprehensive assessment of T-cell receptor β-chain diversity in αβ T cells, Blood 114(19):4099-4107 (2009).
Varani et al., Solution mapping of T cell receptor docking footprints on peptide-MHC, Proc. Natl. Acad. Sci. USA 104(32):13080-13085 (2007).

\* cited by examiner

FIG. 1

868 Vβ-L-Vα-CD28,CD3ζ,LCK

☐ = CDR Loop Mutations that Increase Affinity

Black – WT1/HLA.A2 PE Tetramer 10 nM
Red – SL9 HIV-Gag/HLA.A2 PE Tetramer 10 nM

HUMAN SINGLE-CHAIN T CELL RECEPTORS

CROSS-REFERENCE TO RELATED APPLICATIONS

This application is the U.S. National Stage of International Application No. PCT/US2010/051559, filed Oct. 6, 2010, which claims the benefit of U.S. provisional application Ser. No. 61/248,924, filed Oct. 6, 2009, both of which are incorporated by reference in entirety.

STATEMENT REGARDING FEDERALLY SPONSORED RESEARCH OR DEVELOPMENT

This invention was made with U.S. Government support under Grant number R01 GM55767 awarded by the National Institutes of Health. The U.S. Government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is IMMU_001_01US_ST25.txt. The text file is 30 KB, was created on Sep. 17, 2014, and is being submitted electronically via EFS-Web.

BACKGROUND OF THE INVENTION

T cell receptors (TCRs) mediate recognition of a foreign or self-peptide presented in the context of a self major histocompatability (MHC) complex protein (1). During development, T cells expressing the highest affinity receptors are deleted in the thymus (negative selection). Survival of the T cell, however, depends on a minimal affinity for self MHC (positive selection), assuring that T cells recognition is MHC restricted (2). After development, if recognition of peptide:MHC (pepMHC) is of sufficient affinity, the T cell becomes activated and causes lysis of the target cell. The affinity of the TCR:pepMHC interaction is relatively low, with KD values on the order of 1-500 uM (3).

In recent years, in vitro engineering by yeast and phage display has yielded T cell receptors with >1,000 fold improvements in affinity (4-9). To date there have been only three MHC restricted human TCRs engineered for such improved affinity (reviewed in (10) and Varela-Rohena, 2008 (9). These three receptors were engineered in a full-length TCR format, with the addition of two non-native cysteines in each of the TCR constant domains (Cα and Cβ) to facilitate TCR heterodimer formation through an inter-chain disulfide bond (11). The addition of this disulfide bond allows the TCR to be expressed at higher levels on the surface of yeast (12) or phage (11). Other engineering efforts have focused on using a single-chain TCR (scTCR) format, consisting of the variable domains of the T cell receptor connected by a flexible linker (Vα-linker-Vβ or Vβ-linker-Vα). Although the first scTCRs were described eighteen years ago (13, 14), there have been major difficulties in producing quantities sufficient for clinical or even pre-clinical use (10). Although analogous to antibody fragments in many aspects (reviewed in (10)), unlike the hundreds to thousands of antibody single-chain fragments (scFv) that have been expressed to date, the scTCR format has required mutations to allow for stable, higher level expression of the variable domains in the absence of the constant domains (12). Accordingly, stable scTCRs have been isolated by yeast display only through random mutagenesis and subsequent selection with clonotypic antibodies to select for mutations that allow for surface expression on yeast and expression at high levels in soluble form (6, 15, 16). These stable scTCR scaffolds were subsequently used for engineering receptors of enhanced affinity (4, 6).

Single-chain TCRs afford significant advantages in contrast to the full length TCR format for engineering, soluble protein expression, and clinical potential. From the perspective of further engineering, higher surface levels of the scTCR can be achieved relative to the full-length TCR in the yeast display system (12). As more TCR molecules are displayed on the surface of each yeast cell, there are improved avidity effects in the detection of peptide-MHC multimers and improved sensitivity of detection. From the perspective of soluble protein expression (i.e. manufacturing), the scTCR is produced as a single polypeptide, avoiding the requirement for production of each TCR chain as separate polypeptides and allowing for production of larger quantities of the properly assembled scTCR that binds to its peptide-MHC ligand. This feature can allow for production yields that are necessary for clinical use. Finally, from the clinical perspective, scTCRs can be formatted as therapeutics or diagnostic reagents similar to scFv fragments. The scTCR has the added advantage of improved tissue penetration because of the reduced size of the scTCR relative to the full-length receptor. This is especially important in cases when the TCR is directed against a tumor antigen, where tumor stroma can be targeted to effectively destroy cancerous cells (17).

Previous efforts to engineer single-chain TCRs were facilitated by having probes available to assess proper folding of both TCR V domains. In the well-characterized 2C (15) and 3L.2 (6) TCR systems, stabilized scTCRs were identified using clonotypic antibodies that recognized the conformation of the properly folded Vα and Vβ domains. Because the wild-type affinity of these receptors for specific pepMHC is relatively low, pep:MHC tetramers could not be used to detect properly folded, stabilized scTCRs.

In the present invention, the three known high-affinity human T cell receptors were cloned into a single-chain format to isolate the first human stabilized scTCRs. The features of the scTCRs that allowed them to be expressed as stable proteins are described. For example, the high-affinity scTCRs were used as templates for random mutagenesis (error-prone PCR), and the stabilized scTCRs were isolated by selection with soluble pep:MHC tetramers. Because the TCRs selected already contained mutations which enhance affinity for pep:MHC, soluble pep:MHC tetramers could be used as probes for the selection of scTCRs with stabilizing mutations. The scTCRs were subsequently produced in large quantities in *E. coli*. More specifically, the isolation of mutants of two stabilized, human scTCRs are described: 1) A6 scTCR specific for a peptide derived from the human T cell lymphotrophic virus Tax protein (peptide: $Tax_{11-19}$, Sequence: LLFGYPVYV, SEQ ID NO:1), and 2) 868 scTCR specific for a human immunodeficiency virus derived peptide from the GAG protein (peptide: $SL9_{77-85}$, Sequence: SLYNTVATL, SEQ ID NO:2). Both of these TCRs used the same exceptionally stable Vαdomain: Vα2 (IMGT: TRAV12 family, Table 1). Herein, it is also demonstrated that a single mutation in the Vα2 controls resistance to thermal denaturation of the Vα2 domain and enhances the stability of the corresponding Vβ domain of the scTCR. The scTCRs described herein have many applications. As an example of an application of the scTCRs of the invention for targeting the peptide-MHC antigens, we show the ability of the soluble 868 scTCR to recognize antigen presenting cells with a peptide derived from HIV Gag protein at low nM peptide concentrations. As a further example of an application of the scTCRs of the invention, the scTCR can be fused to a T cell signaling construct, allowing the gene transfected T cells to mediate recognition of the specific peptide-MHC and a response to the specific peptide-MHC.

SUMMARY OF THE INVENTION

Generally, provided is a single chain VαVβ TCR. The provided scTCR is useful for many purposes, including the treatment of cancer, viral diseases and autoimmune diseases. In a particular embodiment, the scTCR can be prepared and used with a "payload" such as a cytokine or other protein to deliver effector molecules to a cancer cell or virus infected cell. The scTCR provided here can also be used for diagnosis by linking a detectable group to the scTCR. In an embodiment, the scTCR described herein is displayable on the surface of yeast and can be used to engineer scTCRs with higher affinity to a particular ligand. In an embodiment, the scTCR described herein can be expressed in *E. coli* or other art-known protein expression sources and produced in large quantities. The scTCR can be generated against a particular antigen, and used, for example to detect a specific peptide/MHC on the surface of a cell. In an embodiment, the scTCRs disclosed herein can be expressed on yeast for affinity engineering to an antigen. In an embodiment, the scTCRs disclosed can be linked to signaling domains and introduced into T cells that can eliminate the targeted cells.

More specifically, the current invention provides a single-chain VαVβ T cell receptor (sc VαVβ TCR). In the sc VαVβ TCR provided, the variable alpha and variable beta chains are connected using any suitable linker, including those known in the art (for example, the well-known linker that contains repeats of glycine and serine, GGGS, (SEQ ID NO:3) linkers). In an embodiment, provided is a soluble human single-chain TCR having the structure: Vα2-L-Vβ or Vβ-L-Vα2, wherein L is a linker peptide that links Vβ with Vα, Vβ is a TCR variable β region, and Vα2 is a TCR variable a region of the family 2. In an embodiment, the Vα2 region is subfamily Vα2.1. In an embodiment, the single-chain T cell receptor of the current invention uses the Vα2 chain known as IMGT: TRAV12. In an embodiment, in the sc VαVβ TCR provided, the Vα2 region contains a mutation at position 49. In an embodiment, the mutation is Phe$_{V\alpha49}$Ser. In an embodiment, the sc VαVβ TCR of the invention further comprises one or more mutations in CDR2β or CDR3α. In an embodiment, the sc VαVβ TCR of the invention further comprises one or more mutations in CDR3β or CDR2α. In an embodiment, the linker peptide contains more than 5 lysine residues. In an embodiment, the linker peptide contains between 10 and 30 amino acids, based on previous studies with single-chain antibodies (scFv). In an embodiment, the linker peptide is GSADDAKKDAAKKDGKS (SEQ ID NO:4). In an embodiment, the sc VαVβ TCR provided does not contain a constant region. When the terminology sc VαVβ TCR is used herein, it is understood that sc VβVα TCR is also included as the terminology is understood and used in the art. Thus, the Vα and Vβ chains can be connected to each other in any configuration through the linker.

In an aspect of the invention, the sc VαVβ TCR of the invention binds specifically to a ligand with an equilibrium binding constant $K_D$ of between about $10^{-6}$ M and $10^{-12}$ M and all individual values and ranges therein. In an embodiment of this aspect of the invention, the ligand is a peptide/MHC ligand. In an embodiment of this aspect of the invention, the ligand includes a peptide known as SL9 (SEQ ID NO:2) from the HIV Gag protein. In an embodiment, the sequence of the Vα (SEQ ID NO:59) and Vβ (SEQ ID NO:53) regions is from the scTCR known as 868-Z11. In an embodiment, the sc VαVβ TCR of the invention has enhanced stability toward thermal denaturation as compared to the wild type TCR. In an embodiment, the sc VαVβ TCR of the invention has enhanced affinity toward a ligand than the wild type TCR. In an embodiment, the invention includes a TCR functionally equivalent to a TCR specifically provided herein.

Also provided is a sc VαVβ TCR as described herein which includes a biologically active group. As used herein, "biologically active group" means a group that causes a measurable or detectable effect in a biological system. In an embodiment, the biologically active group is selected from: an anti-inflammatory group, an anti-tumor agent, a cytokine, a radioisotope, a prodrug, an immunostimulant, a toxin, or an antibody such as a single-chain Fv. In an embodiment of this aspect of the invention, the biologically active group is a cytotoxic molecule. As used herein, "cytotoxic" means toxic to cells. Cytotoxic molecules do not need to cause complete cell death, but rather, a measurable or detectable inhibition of growth or decrease in cell activity. The scTCR of the invention may be linked to an enzyme capable of converting a prodrug into a drug. This is useful, for example, by allowing the drug to be created where targeted by the scTCR. In an embodiment, the biologically active group is bound to the single-chain TCR through a linker.

Also provided is a sc VαVβ TCR as described herein which includes a detectable group. In an embodiment, the detectable group is one that can be detected by spectroscopic or enzyme-based methods. In an embodiment, the detectable group is a fluorescent group, a radiolabeled group, an absorbing group, or an enzyme with properties that generate detectable products. As known in the art, a biologically active group, detectable group or other group attached to the scTCR can be attached using a flexible peptide linker or other means, and can be covalently or noncovalently attached to the scTCR. These biologically active groups, detectable groups or other groups attached to the scTCR and their use and preparation are known in the art.

Also provided are sc VαVβ TCRs that recognize (or target) a specific antigen. In an embodiment, the TCR is specific for recognition of a virus or fragment thereof. In an embodiment, the TCR is specific for recognition of a cancer-specific epitope. In an embodiment, the TCR is specific for recognition of autoimmune associated epitope. Other targets include those listed in The HLA Factsbook (Marsh, 2000, Academic Press) and others known in the art. Specific target antigens include HIV Gag epitope known as SL9 (SEQ ID NO:2) bound to HLA-A2, the virus epitope from HTLV known as Tax (SEQ ID NO:1)/HLA-A2, and the cancer epitope known as MART1(SEQ ID NO:61)/HLA-A2.

Also provided is a human single-chain TCR for use in a method of treating a disease state in a mammal, comprising: administering an effective amount of the TCR linked to a therapeutically effective molecule to a mammal. As used herein a "disease state" is an abnormal function or condition of an organism. In an embodiment, the disease state is selected from the group consisting of: cancer, virus, bacterial or autoimmune disease. Also provided is a method for producing single-chain T cell receptors comprising expressing a scTCR as described herein in *E. coli*. Also provided is an isolated single-chain TCR as described herein. Also provided is a pharmaceutical composition comprising a scTCR as described herein and a pharmaceutically acceptable carrier. Also provided is the sc VαVβ TCR described herein which has been linked to signaling domains that yields an active TCR on the surface of a T cell. In an embodiment, this scTCR can be used in a method of treating a disease state in a mammal, comprising: cloning the TCR into a vector, introducing the vector into T cells of a patient, and adoptive transferring of the T cells back into a patient.

The variable alpha and variable beta regions preferably correspond to those of a human TCR. However, as long as the TCR retains the desired function, amino acid deletion and/or substitution as compared to the human region is acceptable. The invention includes alpha-beta human scTCRs, as well TCRs from other mammals, including mouse.

BRIEF DESCRIPTION OF THE DRAWINGS

FIG. 1. Sequences of scTCR Templates. Black Background, White Text: High-affinity CDR mutations as identified for A6 in Li et al (7), and for 868 in Varela-Rohena, et al (9). Gray: Ig Fold Residues are shown for reference. Both A6 and 868 belong to TRAV12-2, but 868 shares some residues with TRAV12-1 (boxed residues). CDR2a residue F49 (Residue is highlighted in Gray, Phe (F) residues boxed) is designated as a polymorphic residue by IMGT nomenclature. The Vβ sequences for 1G4 Vβ13.1 (SEQ ID NO:38), A6 Vβ13.1 (SEQ ID NO:39), and 868 Vβ5.2 (SEQ ID NO:40) are shown. The Vα sequences for 1G4 Vα23 (SEQ ID NO:41), A6 Vα2 (SEQ ID NO:42), 868 Vα2 (SEQ ID NO:43), TRAV12-2 (Vα2) (SEQ ID NO:44) and TRAV12-1 (Vα2) (SEQ ID NO:45) are shown.

Black Shaded Background, White Text: High-affinity CDR mutations as identified previously for A6 and for 868 (7, 9). Gray: Ig fold residues. Boxed, Bold Residues: Mutations isolated in more stable scTCR Variants. Top, A6 scTCR sequences of highest yeast surface expressing A6 scTCR mutants. Four Vβ mutations (CDR2β: Ala52Val, Framework 3: Asn63Asp, Asn66Lys, and CDR3β: Gln106Leu) allow for improved stability. Wild type 868 Vβ (SEQ ID NO:52), 868 template Vβ (SEQ ID NO:40), 868-Z6 Vβ (SEQ ID NO:40), 868-Z11 Vβ (SEQ ID NO:53), 868-Z12 Vβ (SEQ ID NO:54), 868-Z17 Vβ (SEQ ID NO:55), 868-Z19 Vβ (SEQ ID NO:56), wild type 868 Vα (SEQ ID NO:52), 868 template Vα (SEQ ID NO:43), 868-Z6 Vα (SEQ ID NO:58), 868-Z11 Vα (SEQ ID NO:59), 868-Z12 Vα (SEQ ID NO:59), 868-Z17 Vα (SEQ ID NO:60) and 868-Z19 Vα (SEQ ID NO:59) are shown in FIG. 6B. Bottom, 868 scTCR variants that allow for improved stability following temperature challenge at 40 degrees celsius. The only conserved mutation among these variants is a residue flanking CDR2α, Phe49Ser.

Figure 7:
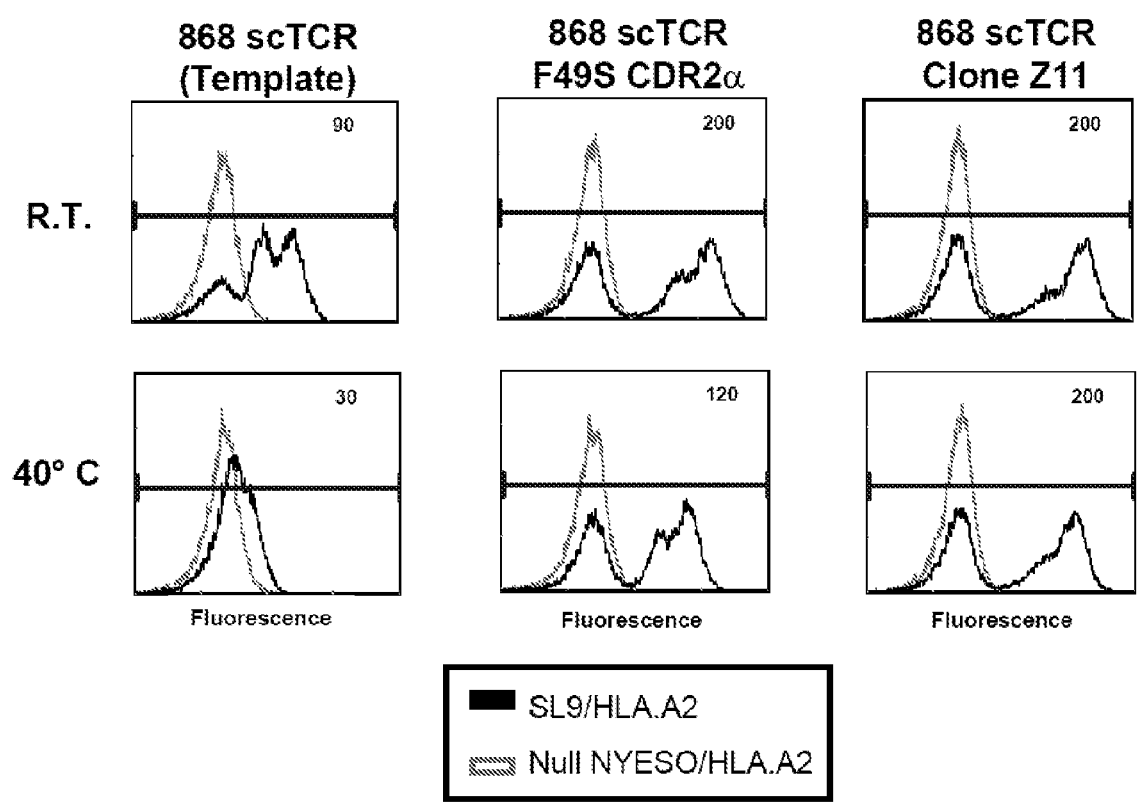

FIG. 7. A Single CDR2a Mutation Allows for Increased Stability (i.e. Surface Levels and Resistance to Thermal Denaturation). The F49S CDR2a mutation was introduced into the 868 scTCR template (Vβ SEQ ID NO:40 and Vα SEQ ID NO:43). Yeast cells expressing the 868 scTCR template (Vβ SEQ ID NO:40 and Vα SEQ ID NO:43), template with mutation, and the clone Z11 (which contains the mutation (Vβ SEQ ID NO:53 and Vα SEQ ID NO:59)) were incubated at room temperature (top row) or at 40° C. for 30 min and then stained with 10 nM SL9 (SEQ ID NO:2)/HLA.A2 phycoerythrin tetramer (black) or null peptide NYESO (SEQ ID NO:5)/HLA.A2 phycoerythrin tetramer (gray) on ice for 45 min. MFI expressed for entire population of yeast cells are shown in upper right of each panel.

FIG. 8. Phe$_{Vα49}$Ser Improves the Stability of the Vα and Vβ 868 scTCR Domains. The 868 scTCR were expressed on the yeast surface with wild-type affinity CDRs (non-bold text, panel A) and high affinity CDR mutations (bold text, panel B) with and without Phe$_{Vα49}$Ser and stained on ice for 45 min with anti-HA antibody (Top Row), anti-Vβ5.2 antibody and goat anti-mouse Ig/APC labeled antibodies (Middle Row, control is goat anti-mouse Ig/APC antibodies only), or SL9 (SEQ ID NO:2)/HLA.A2 or Tax (SEQ ID NO:1)/HLA.A2 (null, Gray) PE tetramer at 100 nM (Black) (Bottom Row). (A) Single-chain 868 TCR with wild-type CDR loops. (8) Single-chain 868 TCR with high affinity CDR loops. 3α WT TNSG is designated SEQ ID NO:46. 3α HA GAHD is designated SEQ ID NO:47.

FIG. 9. CDR Mutations Also Affect Surface Expression of the 868 scTCRs. The 868 scTCR were expressed on the yeast surface with wild-type affinity and high affinity (bold) CDR mutations and stained on ice for 45 min Anti-HA antibody (Top Row, Secondary only control is shown in gray for HA), Anti-Vβ5.2 Antibody and Goat anti-Mouse Ig/APC (Middle Row), or SL9 (SEQ ID NO:2)/HLA.A2 or Tax (SEQ ID NO:1)/HLA.A2 (null, Gray) PE tetramer at 100 nM (Black) (Bottom Row) as in FIG. 5. (A) 868 CDR3α high affinity mutations introduced into 868 scTCR template (Vβ SEQ ID NO:40 and Vα SEQ ID NO:43). (8) 868 CDR2β high affinity mutations introduced into 868 scTCR template (Vβ SEQ ID NO:40 and Vα SEQ ID NO:43). 3α WT TNSG is designated SEQ ID NO:46. 3α HA GAHD is designated SEQ ID NO:47.

FIG. 10. Soluble Expression of the 868-Z11 scTCR: Analysis by SDS Polyacrylamide gel electrophoresis. Clone Z11 (Vβ SEQ ID NO:53 and Vα SEQ ID NO:59) was expressed in the E. coli pET28 expression system. (A) Induction of E. coli that expresses the scTCR 868 Clone Z11 (Vβ SEQ ID NO:53 and Vα SEQ ID NO:59) (expected size=29 kDA). Protein was refolded in vitro and biotinylated using Sulfo-NHS EZ-Link Kit (Pierce). (8) Biotinylation of the purified and biotinyated scTCR was monitored by gel shift of the 30 kDa labeled protein in the presence of streptavidin.

FIG. 11. Binding of HIV Peptide-Loaded Target Cells by Soluble, Biotinylated 868 scTCR. (A) Flow histograms of T2 antigen presenting cells (HLA.A2+) incubated with the SL9 (10 µM, SEQ ID NO:2) peptide or the control peptide Tax (10 µM, SEQ ID NO:1) incubated with the indicated concentrations of 868 Z11 (Vβ SEQ ID NO:53 and Vα SEQ ID NO:59) biotinylated scTCR (Gray, solid line as indicated). Cells were incubated at room temperature for 30 min with scTCR, washed, and incubated with SA:PE for 30 min. Concentrations of scTCR used are as indicated by arrows. The highest scTCR concentration, 100 nM was used with excess null Tax peptide (Gray, leftmost curve in histogram, SEQ ID NO:1). (8) MFI of scTCR titration shown in (A), with the EC50 (concentration of scTCR at half-maximal binding) calculated for 868 Z11 scTCR (Vβ SEQ ID NO:53 and Vα SEQ ID NO:59). (C) The SL9 peptide (Gray text, concentration as indicated, SEQ ID NO:2) was titrated on T2 peptide loaded cells using a saturating concentration (100 nM) of the multi-biotinylated 868 Z11 scTCR (Vβ SEQ ID NO:53 and Vα SEQ ID NO:59). Tax control peptide (SEQ ID NO:1) was used at 10 µM (dark gray) with 100 nM multi-biotinylated scTCR.

Figure 12:
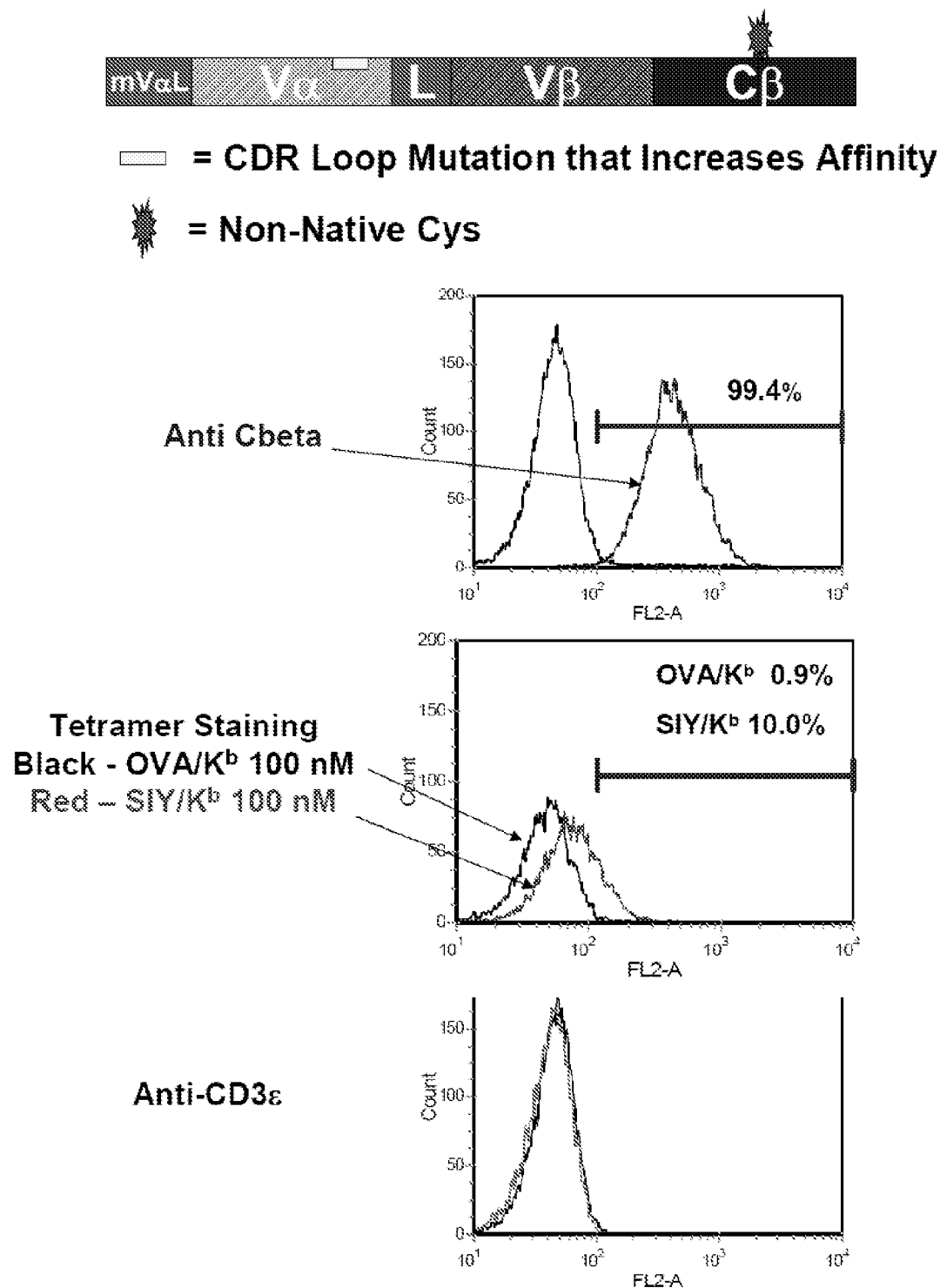

FIG. 12. Schematic and cell surface expression of three domain TCR (Vα-L-VβCβ) with stabilizing mutations. The construct shown was cloned into the retroviral vector, transduced into T cell hybridoma line 584, and the transduced, sorted cells were stained with an anti-Cβ antibody, the pepMHC tetramers SIY (SEQ ID NO:17)/$K^b$ and OVA (SEQ ID NO:18)/$K^b$, and an anti-CD3ε antibody. Control for Anti-Cβ and anti-CD3ε is 58−/−line stained with anti-Cβ or anti-CD3ε. For tetramer staining control, the sorted three domain TCR expressing line was stained with 100 nM OVA (SEQ ID NO:18)/$K^b$ PE tetramer. This construct was able to associate with endogenous alpha chains (data not shown) despite the fact that it contained a cysteine in the Cβ domain (Ser57Cys) that has been shown to reduce the association with a Cα containing chain.

Figure 13:
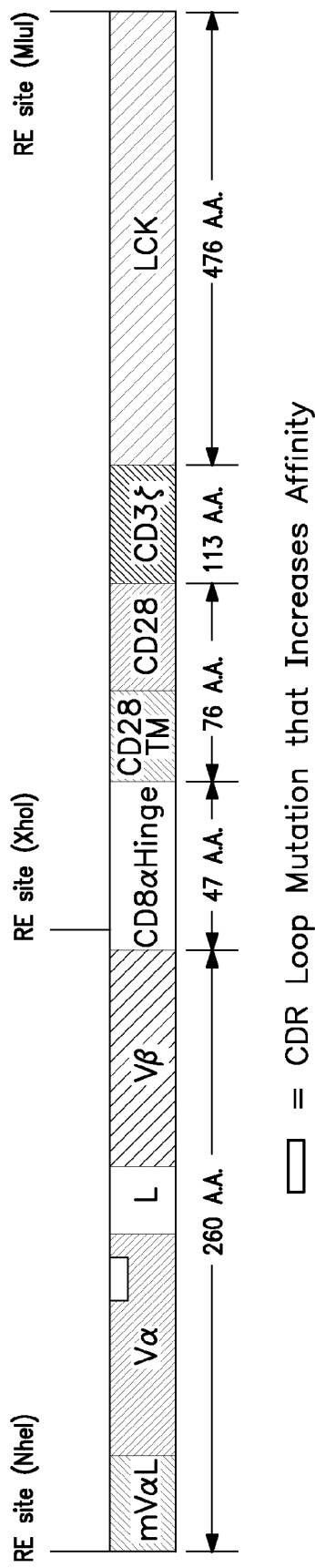

FIG. 13. Schematic of the single-chain TCR fusion to CD28, CD3zeta, LCK domains. The high-affinity scTCR called m33 (5) was cloned, with the CDR3α mutations that confer high affinity, as a fusion to the domains shown. The construct included linkers and restriction sites, as shown, for ease of cloning.

Figure 14:
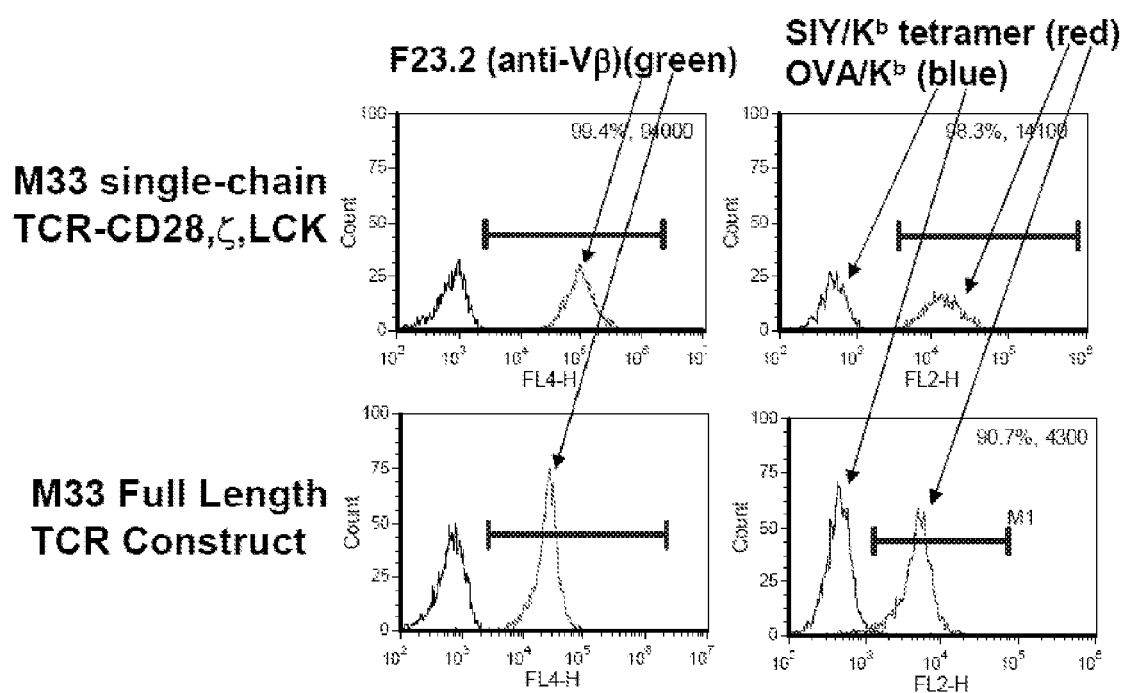

FIG. 14. Surface levels of M33 scTCR fusion compared to a conventional full-length TCR. The construct shown in FIG. 13 was cloned into the retroviral vector and transduced into T cell hybridoma line 58−/−. These transduced T cells or the conventional full length construct were stained with an anti-Vβ antibody (F23.2) (Control is 58−/− line stained with anti-Vβ8.2, black, left column of histograms) or the pepMHC tetramers SIY (SEQ ID NO:17)/$K^b$ or OVA (SEQ ID NO:18)/$K^b$ at 100 nM. The single-chain construct was expressed at about 3-times the surface level as the full-length conventional αβ TCR m33 (18).

Figure 15:
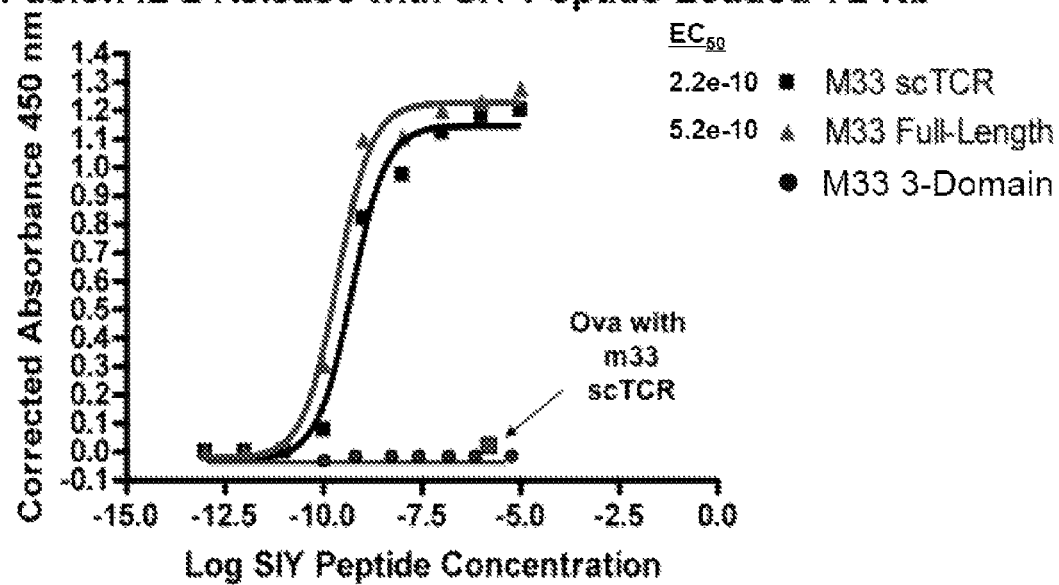

FIG. 15. T cells that express the M33 scTCR fusion are stimulated by specific antigenic peptide to release IL-2, a marker of T cell activation. Gray Triangles: M33 Full Length TCR, Black Squares: M33 scTCR fusion, Gray Circles: M33 three domain TCR (VαVβCβ, FIG. 12). The T cells shown in FIG. 14 were titrated with SIY peptide (SEQ ID NO:17) in the presence of an antigen presenting cell (T2-K$^b$). EC$_{50}$ values (concentrations of peptide that yield half-maximal stimulation) were based on 3 independent experiments. Arrow shows that a control null peptide OVA (SEQ ID NO:18) did not stimulate cells expressing the m33 scTCR fusion, showing that the T cells have excellent specificity. The results also show that the m33 scTCR fusion was activated at similar SIY (SEQ ID NO:17) concentrations to the full-length m33 ai3 TCR.

FIG. 16A-D. (A): Comparison of 2C (wild-type affinity) versus m33 (high affinity) scTCR fusion surface expression and peptide/MHC tetramer binding. The wild type TCR 2C that lacks the CDR3α mutations of m33 was cloned into the same scTCR signaling fusion as m33 (FIG. 13). The transduced T cells were stained with an anti-Vβ antibody (F23.2), an anti-clonotypic antibody 1 B2 that binds to 2C but not m33 TCRs, and the pepMHC tetramers SIY (SEQ ID NO:17)/K$^b$ or OVA (SEQ ID NO:18)/K$^b$. Control staining for anti-Vβ antibody (F23.2) and anti-clonotypic antibody 1 B2 is shown as 58−/− line stained with indicated antibody. The 2C full-length αβ TCR heterodimer expressing T cells (18) are also shown as a comparison. As with the m33 scTCR fusion, the 2C scTCR was expressed at several fold higher levels than the 2C full length TCR. (B, C, D): scTv and full-length 2C (K$_D$=30 μM for SIY (SEQ ID NO:17)/K$^b$) and m33 (K$_D$=30 nM for SIY (SEQ ID NO:17)/K$^b$) constructs were introduced into 58$^{-/-}$ cells. Cell surface expression was monitored with anti-Vβ8 (16B) or SIY (SEQ ID NO:17)/K$^b$ SA:PE labeled tetramer at 40 nM (16C) by flow cytometry. SIY (SEQ ID NO:17)/K$^b$ tetramer binding to scTv and full-length constructs was also examined at various concentrations of tetramer (16D).

Figure 16A:
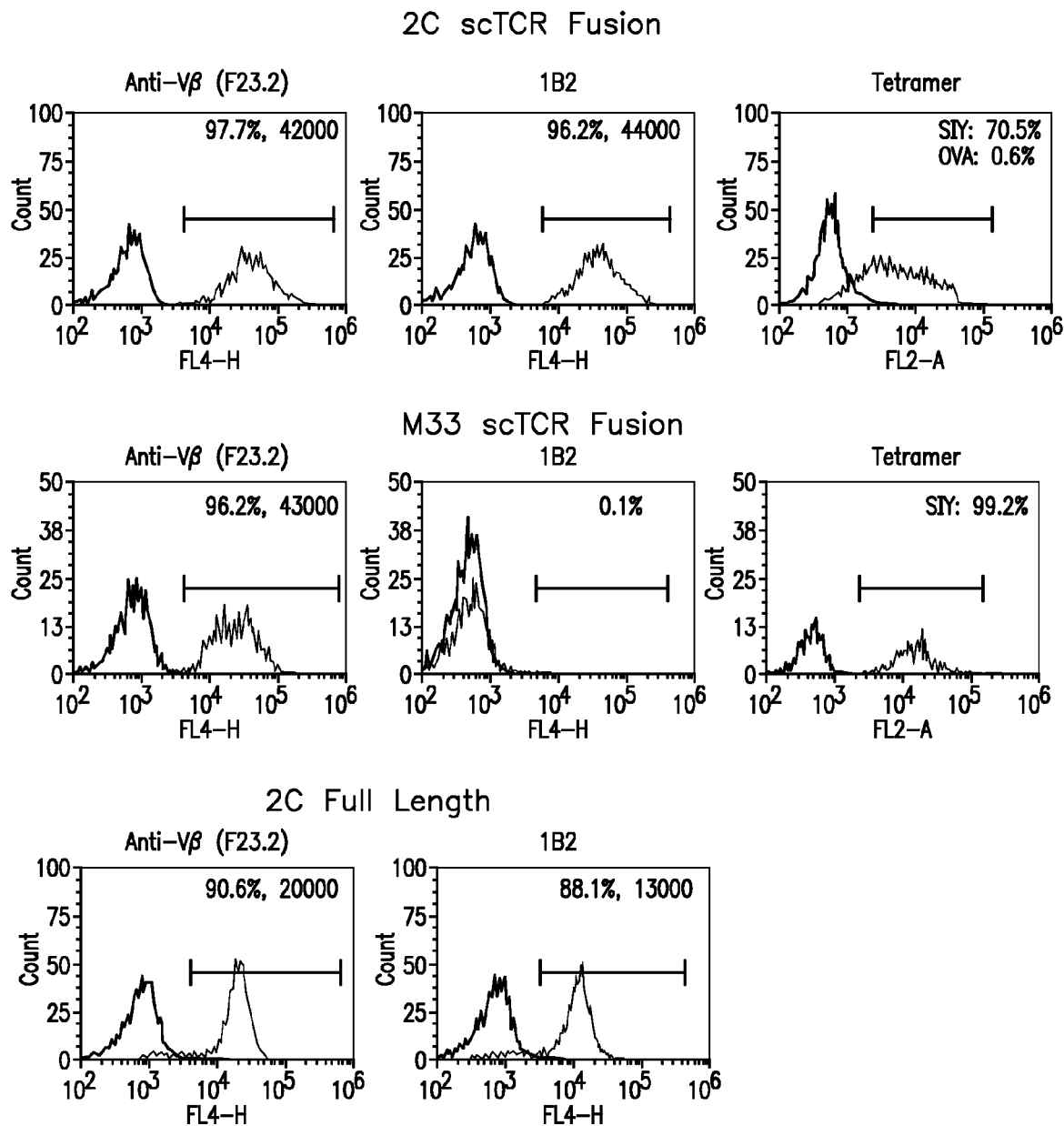
Figure 16B:
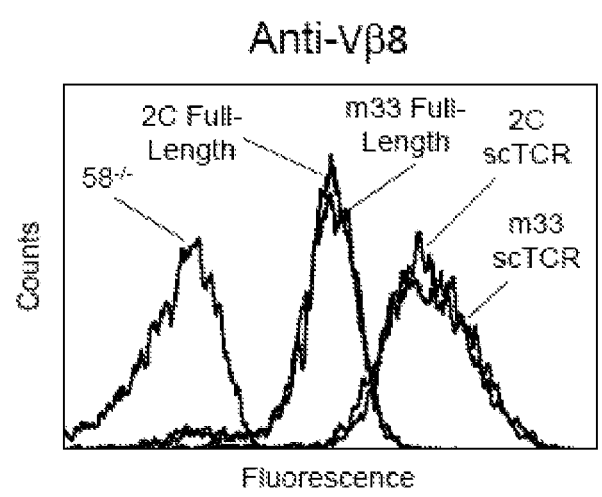
Figure 16C:
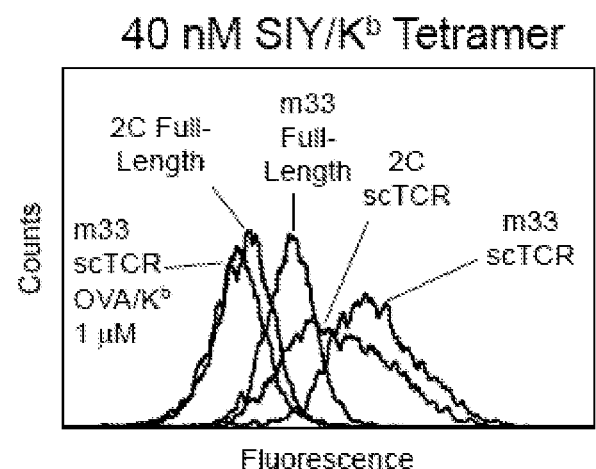
Figure 16D:
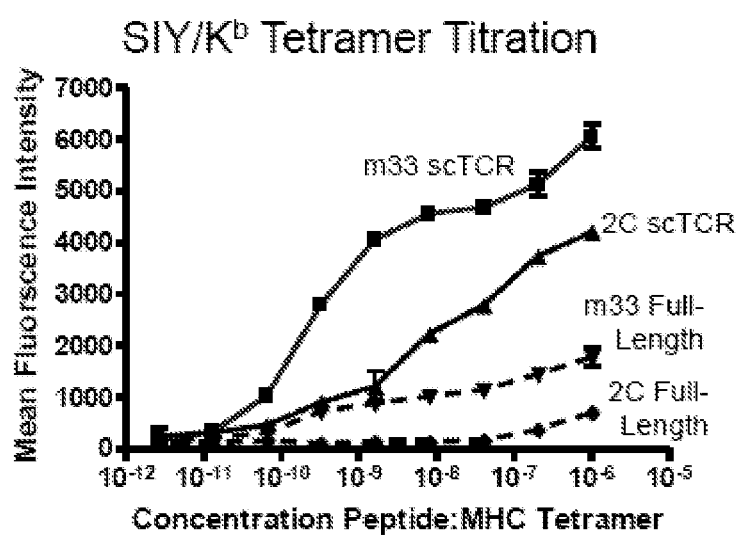
Figure 17:
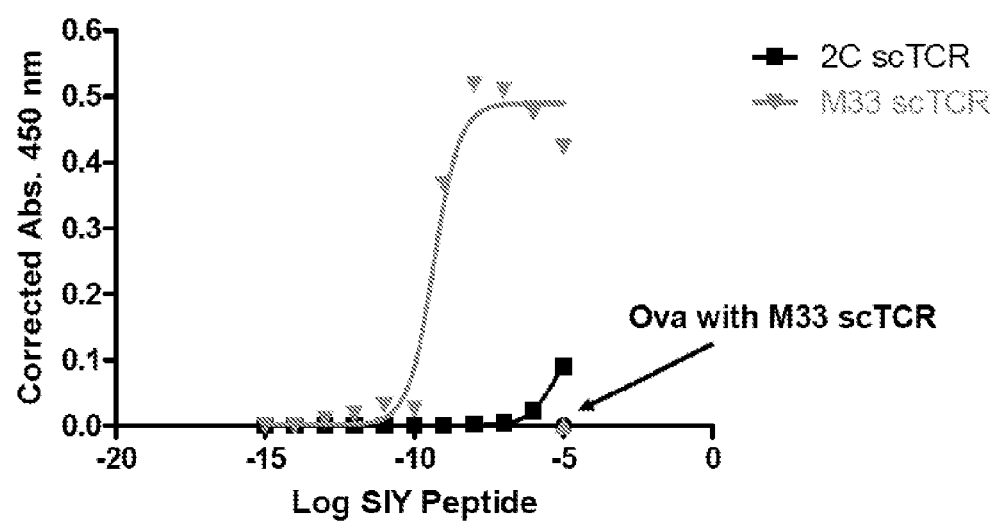

FIG. 17. T cells that express the M33 scTCR fusion are stimulated by specific antigenic peptide to release IL-2 with much higher sensitivity than the 2C scTCR. T cell hybridomas expressing the 2C and m33 scTCR fusions constructs shown in FIGS. 14 to 16 were assayed at various concentrations of SIY peptide (SEQ ID NO:17) in the presence of an antigen presenting cell (T2-K$^b$). The higher affinity of the m33 scTCR was necessary for improved activity, as the wild-type affinity 2C scTCR mediated T cell activation only at high concentrations of SIY peptide (SEQ ID NO:17). The control peptide OVA (SEQ ID NO:18) did not stimulate the m33 scTCR T cells.

Figure 18:
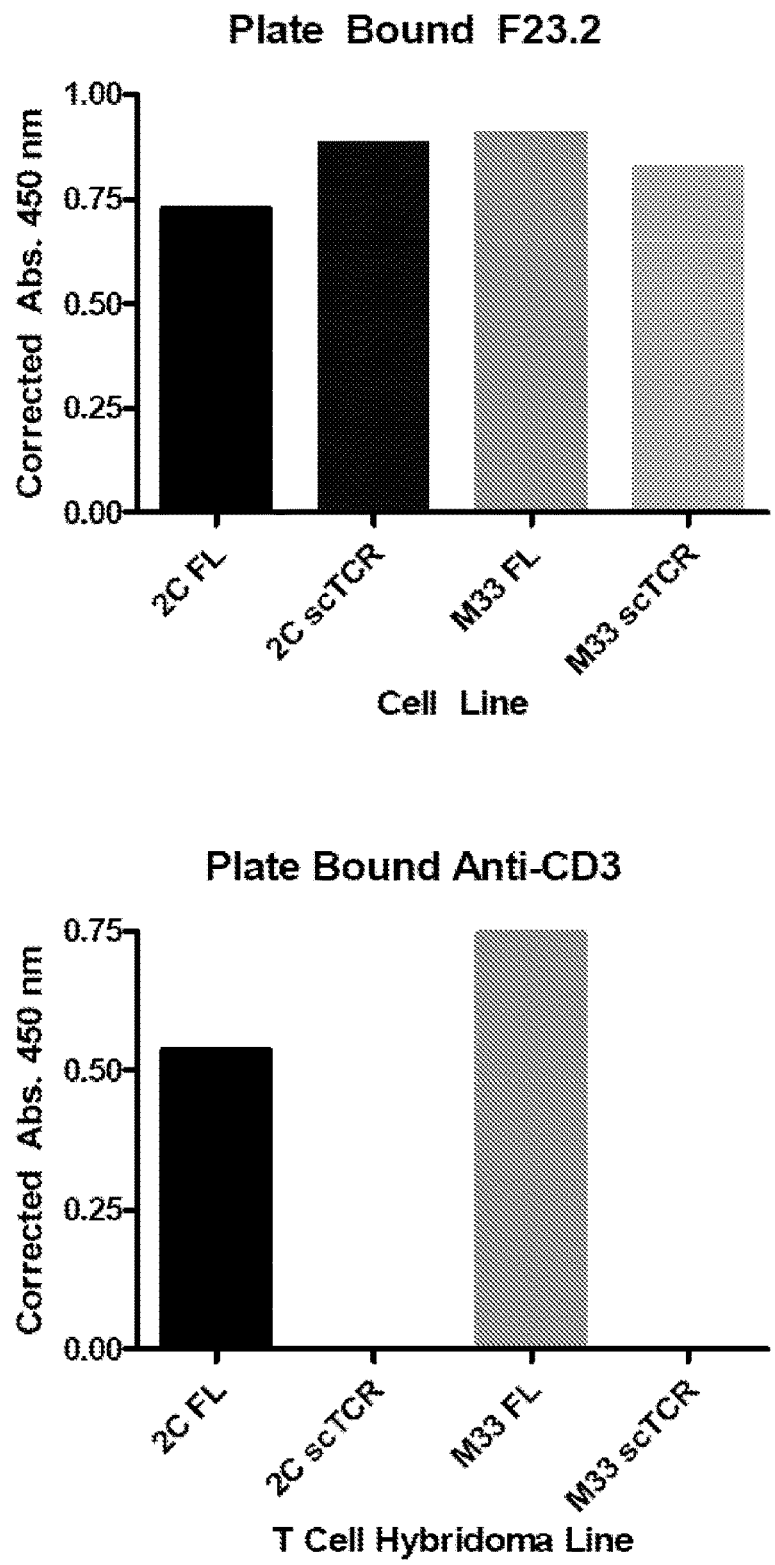

FIG. 18. IL-2 release from scTCR transduced T cells after 24 hour exposure to plate bound anti-mouse Vβ8 antibody or anti-CD3ε antibody. To prove that the T cell lines could all be activated through their scTCR constructs, and that the activity of the scTCR fusions did not require association with CD3, plate bound antibodies were used in a 24-hour IL-2 release assay. The full-length (FL) TCRs with conventional αβ TCR and CD3 complexes were used for comparison. The scTCR fusions were activated in the presence of Vβ antibody, but not in the presence of anti-CD3 antibody, whereas the full-length (FL) constructs mediated activity by both antibodies, consistent with the observations that the conventional FL TCR constructs are associated with CD3 on the cell surface.

FIG. 19. Expression and characterization of the stabilized scTCR 868 Z11 as a fusion to signaling domains. (A) Schematic of human Vα2+ 868-Z11 scTCR fused to CD28, CD3, and LCK. (B) Staining of transduced T cells with an anti-Vβ antibody (left, gray) and peptide/MHC tetramers (HIV SL9 (SEQ ID NO:2)/HLA-A2 cognate ligand, and WT1/HLA-A2, a null ligand). Control for anti-Vβ antibody (Black line, Left histogram) is the 58−/− line stained with anti-human Vβ5.2 antibody, and control for tetramer staining is the null peptide WT1/HLA-A2. (C) Activation of T cells with plate bound anti-human Vβ5.2, anti-CD3 antibody, or peptide-loaded HLA.A2+ antigen presenting cells (antigenic peptide SL9-HIV-Gag, SEQ ID NO:2, or the control null peptide Tax, SEQ ID NO:1). To assess antigen specific activation, 868 scTv expressing cells were stimulated with plate-bound SL9 (SEQ ID NO:2)/HLA.A2 or Tax (SEQ ID NO:1)/HLA.A2 tetramers at various concentrations. (D) Data in 19D are representative of two independent experiments. 868-Z11 scTCR is surface expressed as a fusion protein and is activated in a peptide dependent and specific manner. The transduced T cell is useful for adoptive therapy strategies targeting cells that express HIV.

DETAILED DESCRIPTION OF THE INVENTION

The following description is intended to facilitate understanding of the invention but is not intended to be limiting.

In general, the terms and phrases used herein have their art-recognized meaning, which can be found by reference to standard texts, journal references and contexts known to those skilled in the art. The definitions are provided to clarify their specific use in the context of the invention.

As used herein, "linked" refers to an association between two groups which can be a covalent or non-covalent association. Groups may be linked using a variable length peptide chain, a non-amino acid chemical group or other means as known in the art. A linker region can be an amino acid sequence that operably links two functional or structural domains of a protein or peptide.

The invention contemplates a DNA vector that includes at least one DNA segment encoding a scTCR of the invention.

As used herein, the term "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

As used herein, the term "effective amount" is intended to encompass contexts such as a pharmaceutically effective amount or therapeutically effective amount. For example, in embodiments the amount is capable of achieving a beneficial state, beneficial outcome, functional activity in a screening assay, or improvement of a clinical condition.

As used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art. Particular examples of cancer cells include breast cancer, colon cancer, skin cancer, ovarian cancer, leukemia, lung cancer, liver cancer, testicular cancer, esophageal cancer, and other types of cancer.

Therapeutic products can be made using the materials shown herein. Effective amounts of therapeutic products are the minimum dose that produces a measurable effect in a subject. Therapeutic products are easily prepared by one of ordinary skill in the art. In one embodiment, a scTCR of the invention is administered directly to a patient. In one embodiment, a scTCR of the invention is linked to PEG or to immunoglobulin constant regions, as known in the art. This embodiment lengthens the serum clearance. These methods and other methods of administering, such as intravenously, are known in the art. Useful dosages are easily determined by one of ordinary skill in the art.

In the figures and tables which present amino acid sequences, the wild type is designated "WT". In the sequences presented below the top sequence, a dash indicates the amino acid is not present as compared to other sequences. A letter indicates a substitution has been made in that position from the top sequence.

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Downstream means on the 3' side of any site in DNA or RNA.

Expression refers to the transcription of a gene into structural RNA (rRNA, tRNA) or messenger RNA (mRNA) and subsequent translation of a mRNA into a protein.

An amino acid sequence that is functionally equivalent to a specifically exemplified TCR sequence is an amino acid sequence that has been modified by single or multiple amino acid substitutions, by addition and/or deletion of amino acids, or where one or more amino acids have been chemically modified, but which nevertheless retains the binding specificity and high affinity binding activity of a cell-bound or a soluble TCR protein of the present invention. Functionally equivalent nucleotide sequences are those that encode polypeptides having substantially the same biological activity as a specifically exemplified cell-bound or soluble TCR protein. In the context of the present invention, a soluble TCR protein lacks the portions of a native cell-bound TCR and is stable in solution (i.e., it does not generally aggregate in solution when handled as described herein and under standard conditions for protein solutions).

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

Isolated means altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to effect their normal functions relative to each other. For instance, a promoter region would be operably linked to a coding sequence if the promoter were capable of effecting transcription of that coding sequence.

A polypeptide is a linear polymer of amino acids that are linked by peptide bonds.

Promoter means a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into at least one cloning site).

Transformation means the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

High affinity T cell receptor (TCR) means an engineered TCR with stronger binding to a target ligand than the wild type TCR. Some examples of high affinity include an equilibrium binding constant for a target ligand of between about $10^{-6}$ M and $10^{-12}$ M and all individual values and ranges therein.

It will be appreciated by those of skill in the art that, due to the degeneracy of the genetic code, numerous functionally equivalent nucleotide sequences encode the same amino acid sequence. These functionally equivalent sequences are intended to be included here to the same extent as if specifically described.

Additionally, those of skill in the art, through standard mutagenesis techniques, in conjunction with the assays described herein, can obtain altered TCR sequences and test them for the expression of polypeptides having particular binding affinity. Useful mutagenesis techniques known in the art include, without limitation, oligonucleotide-directed mutagenesis, region-specific mutagenesis, linker-scanning mutagenesis, and site-directed mutagenesis by PCR [see e.g. Sambrook et al. (1989) and Ausubel et al. (1999)].

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In an embodiment, a scTCR of the invention may contain additional mutations in any region or regions of the variable domain that results in a stabilized protein. In one embodiment, one or more additional mutations is in one or more of CDR1, CDR2, HV4, CDR3, FR2, and FR3. The regions used for mutagenesis can be determined by directed evolution, where crystal structures or molecular models are used to generate regions of the TCR which interact with the ligand of interest (toxin or antigen, for example). In other examples, the variable region can be reshaped, by adding or deleting amino acids to engineer a desired interaction between the scTCR and the ligand.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50° C., 6×SSC (sodium chloride/sodium citrate buffer) and 0.1% SDS (sodium dodecyl sulfate) indicate about 60-70% homology, hybridization and wash conditions of 50-65° C., 1×SSC and 0.1% SDS indicate about 82-97% homology, and hybridization and wash conditions of 52° C., 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the Internet at http://www.ncbi.nlm.nih.gov and a version of ClustalW is available at http://www2.ebi.ac.uk.

Industrial strains of microorganisms (e.g., *Aspergillus niger*, *Aspergillus ficuum*, *Aspergillus awamori*, *Aspergillus oryzae*, *Trichoderma reesei*, *Mucor miehei*, *Kluyveromyces lactis*, *Pichia pastoris*, *Saccharomyces cerevisiae*, *Escherichia coli*, *Bacillus subtilis* or *Bacillus licheniformis*) or plant species (e.g., canola, soybean, corn, potato, barley, rye, wheat) may be used as host cells for the recombinant production of the TCR peptides. As the first step in the heterologous expression of a high affinity TCR protein or soluble protein, an expression construct is assembled to include the TCR or soluble TCR coding sequence and control sequences such as promoters, enhancers and terminators. Other sequences such as signal sequences and selectable markers may also be included. To achieve extracellular expression of the scTCR, the expression construct may include a secretory signal sequence. The signal sequence is not included on the expression construct if cytoplasmic expression is desired. The promoter and signal sequence are functional in the host cell and provide for expression and secretion of the TCR or soluble TCR protein. Transcriptional terminators are included to ensure efficient transcription. Ancillary sequences enhancing expression or protein purification may also be included in the expression construct.

Various promoters (transcriptional initiation regulatory region) may be used according to the invention. The selection of the appropriate promoter is dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the invention. A signal sequence which is homologous to the TCR coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 by on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (λZAP and pBLUESCRIPT SK-1, Stratagene, LaJolla, Calif.; pET, Novagen Inc., Madison, Wis.—cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into S. cerevisiae cells by protoplast transformation or electroporation. Electroporation of S. cerevisiae is readily accomplished, and yields transformation efficiencies comparable to spheroplast transformation.

Monoclonal or polyclonal antibodies, preferably monoclonal, specifically reacting with a TCR protein at a site other than the ligand binding site may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1999) *Current Protocols in Molecular Biology*, John Wiley & Sons, Inc., New York.

scTCRs in cell-bound or soluble form which are specific for a particular target ligand are useful, for example, as diagnostic probes for screening biological samples (such as cells, tissue samples, biopsy material, bodily fluids and the like) or for detecting the presence of the target ligand in a test sample. Frequently, the scTCRs are labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. Additionally the scTCR can be coupled to a ligand for a second binding molecules: for example, the scTCR can be biotinylated. Detection of the TCR bound to a target cell or molecule can then be effected by binding of a detectable streptavidin (a streptavidin to which a fluorescent, radioactive, chemiluminescent, or other detectable molecule is attached or to which an enzyme for which there is a chromophoric substrate available). United States Patents describing the use of such labels and/or toxic compounds to be covalently bound to the scTCR include but are not limited to U.S. Pat. Nos. 3,817,837; 3,850,752; 3,927,193; 3,939,350; 3,996,345; 4,277,437; 4,275,149; 4,331,647; 4,348,376; 4,361,544; 4,468,457; 4,444,744; 4,640,561; 4,366,241; RE 35,500; 5,299,253; 5,101,827; 5,059,413. Labeled scTCRs can be detected using a monitoring device or method appropriate to the label used. Fluorescence microscopy or fluorescence activated cell sorting can be used where the label is a fluorescent moiety, and where the label is a radionuclide, gamma counting, autoradiography or liquid scintillation counting, for example, can be used with the proviso that the method is appropriate to the sample being analyzed and the radionuclide used. In addition, there can be secondary detection molecules or particle employed where there is a detectable molecule or particle which recognized the portion of the scTCR which is not part of the binding site for the target ligand in the absence of a MHC component as noted herein. The art knows useful compounds for diagnostic imaging in situ; see, e.g., U.S. Pat. Nos. 5,101,827; 5,059,413. Radionuclides useful for therapy and/or imaging in vivo include $^{111}$Indium, $^{97}$Rubidium, $^{125}$Iodine, $^{131}$Iodine, $^{123}$Iodine, $^{67}$Gallium, $^{99}$Technetium. Toxins include diphtheria toxin, ricin and castor bean toxin, among others, with the proviso that once the TCR-toxin complex is bound to the cell, the toxic moiety is internalized so that it can exert its cytotoxic effect. Immunotoxin technology is well known to the art, and suitable toxic molecules include, without limitation, chemotherapeutic drugs such as vindesine, antifolates, e.g. methotrexate, cisplatin, mitomycin, .anthrocyclines such as daunomycin, daunorubicin or adriamycin, and cytotoxic proteins such as ribosome inactivating proteins (e.g., diphtheria toxin, pokeweed antiviral protein, abrin, ricin, *pseudomonas* exotoxin A or their recombinant derivatives. See, generally, e.g., Olsnes and Pihl (1982) *Pharmac. Ther.* 25:355-381 and *Monoclonal Antibodies for Cancer Detection and Therapy*, Eds. Baldwin and Byers, pp. 159-179, Academic Press, 1985.

The general structure of TCR molecules and methods of making and using including binding to a peptide:Major Histocompatibility Complex have been disclosed. See, for example PCT/US98/04274; PCT/US98/20263; WO99/60120.

scTCRs specific for a particular target ligand are useful in treating animals and mammals, including humans believed to be suffering from a disease associated with the particular antigen.

The scTCR compositions can be formulated by any of the means known in the art. They can be typically prepared as injectables, especially for intravenous, intraperitoneal or synovial administration (with the route determined by the particular disease) or as formulations for intranasal or oral administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active ingredients are often mixed with optional pharmaceutical additives such as excipients or carriers which are pharmaceutically acceptable and compatible with the active ingredient. Suitable excipients include but are not limited to water, saline, dextrose, glycerol, ethanol, or the like and combinations thereof. The concentration of the scTCR in injectable, aerosol or nasal formulations is usually in the range of 0.05 to 5 mg/ml. The selection of the particular effective dosages is known and performed without undue experimentation by one of ordinary skill in the art. Similar dosages can be administered to other mucosal surfaces.

In addition, if desired, vaccines may contain minor amounts of pharmaceutical additives such as auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. Such additional formulations and modes of administration as are known in the art may also be used.

The scTCRs of the present invention and/or binding fragments having primary structure similarity (more than 90% identity) to the TCR variable regions and which maintain the high affinity for the target ligand may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

scTCRs for therapeutic use are administered in a manner compatible with the dosage formulation, and in such amount and manner as are prophylactically and/or therapeutically effective, according to what is known to the art. The quantity to be administered, which is generally in the range of about 100 to 20,000 µg of protein per dose, more generally in the range of about 1000 to 10,000 µg of protein per dose. Similar compositions can be administered in similar ways using labeled scTCRs for use in imaging, for example, to detect cells to which a target ligand is bound. Precise amounts of the active ingredient required to be administered may depend on the judgment of the physician or veterinarian and may be peculiar to each individual, but such a determination is within the skill of such a practitioner.

The vaccine or other immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months. Humans (or other animals) immunized with the retrovirus-like particles of the present invention are protected from infection by the cognate retrovirus.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*, Glover (ed.) (1985) DNA Cloning Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York. Abbreviations and nomenclature, where employed, are deemed standard in the field and commonly used in professional journals such as those cited herein.

Autoimmune diseases are those diseases in which the immune system produces an immune response against an antigen that is normally present in the host. Autoimmune diseases include rheumatoid arthritis, adjuvant arthritis, myasthenia gravis, encephalomyelitis, multiple sclerosis, thyroiditis, inflammatory bowel disease or systemic lupus erythematosus, type I diabetes, non-obese diabetes, Grave's disease, Hashimoto's disease, osteoarthritis, dermatitis, hepatitis, pemphigus vulgaris, celiac disease, Sjogren's syndrome, Addison's disease, primary myxedema, Goodpasture's syndrome, tuberculoid leprosy, ankylosing spondylitis, Reiter's disease, uveitis, amyloidosis, psoriasis vulgaris, idiopathic hemochromatosis and psorasis.

A cytokine is a protein, peptide or glycoprotein made by cells that affect other cells.

Mammal includes both human or non-human mammals.

As used herein, a sequence that is a "functional equivalent" of another sequence has the same or similar function in a given system. Some examples of functional equivalents of TCR disclosed herein include TCRs with mutations that do not affect the function of the TCR. The presence of and identity of these mutations are easily understood and determined by one of ordinary skill in the art. Other examples of functional equivalents include TCRs that share 90% sequence identity with the TCR disclosed. Other examples of functional equivalents include TCRs that share 95% sequence identity with the TCRs disclosed. Other examples of functional equivalents include TCRs that share 97% sequence identity with the TCRs disclosed. Functional equivalents of the scTCRs disclosed herein are intended to be included.

The following examples further describe nonlimiting examples of the invention. In the text herein, numbers in parentheses refer to references which are listed elsewhere herein.

Example 1. Yeast Display of Human Single-Chain and Full-Length TCRs

Figure 1:
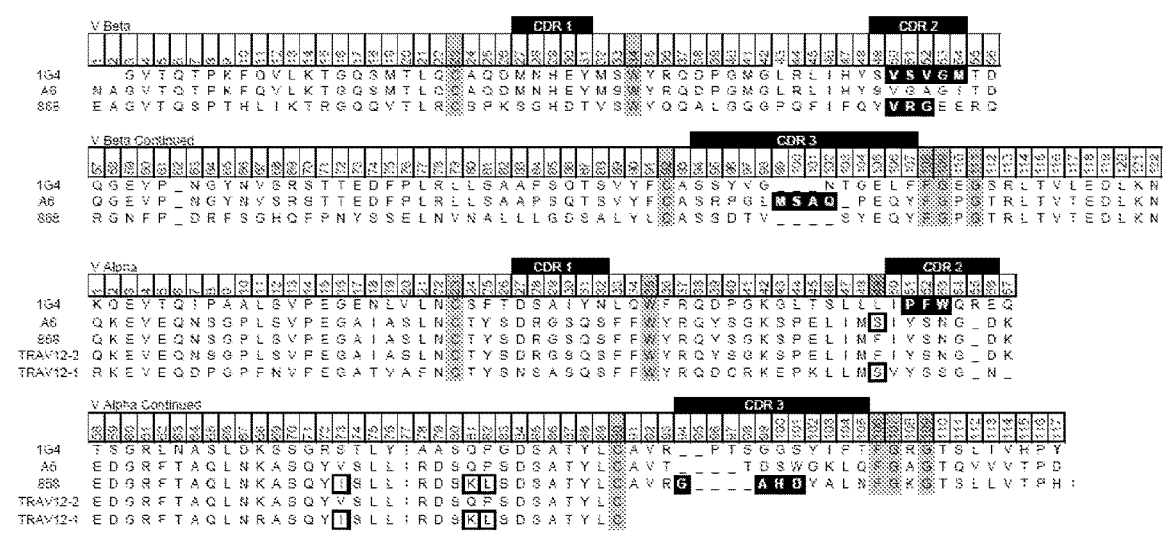

Three human T cell receptors (1G4, A6, 868) that were previously engineered for improved affinity by phage display using a full-length display format were used for this study (7, 9, 19). The variable domains of these TCRs contain complementarity determining region (CDR) mutations that confer high affinity for specific pep:MHC (FIG. 1). The variants selected all have measured KD values reported to be at least 10 nM. TCRs specific for peptides derived from NYESO prostate tumor antigen (1G4 TCR, SEQ ID NO:5), human T cell lymphotrophic virus tax protein (A6 TCR, SEQ ID NO:1), and human immunodeficiency virus gag protein (868 TCR) were synthesized (Genscript) with the variable domains attached by a flexible linker (Vβ-linker-Vα) and high affinity mutations as described (Table 1). The majority of T cell receptor variable domains cannot be expressed in heterologous expression systems in the absence of constant domains, and consequently stabilizing mutations need to be introduced into the scTCRs to allow for yeast surface expression (12, 15, 20). We used yeast display and in vitro evolution to attempt to isolate stabilized forms of the 1G4, A6 and 868 scTCRs (Table 1).

TABLE 1

T Cell Receptor High Affinity Mutations Used in Single Chain TCR Format

| TCR | Vα | Vβ | CDR2α | CDR3α | CDR2β | CDR3β | Antigen |
|---|---|---|---|---|---|---|---|
| 1G4 | 23.1 | 13.1 | IQSSQ (SEQ ID NO: 21) | PTSGGSYIPT (SEQ ID NO: 22) | VGAGI (SEQ ID NO: 23) | SSYVGNTGELF (SEQ ID NO: 24) | NYESO |
|  |  |  | IPFWQ (SEQ ID NO: 25) |  | VSVGM (SEQ ID NO: 26) |  | NYESO (SEQ ID NO: 5)/HLA.A2 |
| A6 | 2.1 | 13.1 | SIYSNG (SEQ ID NO: 27) | VTTDSWGKLQ (SEQ ID NO: 28) | SVGAGI (SEQ ID NO: 29) | RPGLAGGRPELY (SEQ ID NO: 30) | HTLV |
|  |  |  |  |  |  | RPGLMSAQPELY (SEQ ID NO: 31) | Tax (SEQ ID NO: 1)/HLA.A2 |
| 868 | 2.1 | 5.2 | FIYSNG (SEQ ID NO: 32) | VRTNSGYALN (SEQ ID NO: 33) | YYEEEE (SEQ ID NO: 34) | SDTVSYEQY (SEQ ID NO: 35) | HIV |
|  |  |  |  | VRGAHDYALN (SEQ ID NO: 36) | YVRGEE (SEQ ID NO: 37) |  | Gag SL9 (SEQ ID NO: 2)/HLA.A2 |

T Cell Receptor Mutations that confer high affinity are shown in bold below the corresponding CDR. The first residue of CDR2α for Vα2.1 is polymorphic, but is provided as phenylalanine in IMGT nomenclature (TRAV12-2). High affinity mutations (Bold) for 1G4 from Sami, Boulter, and Jakobsen et al., *Protein Eng Des Sel*, 2007, A6 from Li and Boulter et al., *Nature Biotechnology*, 2005, and for 868 from Varela-Rohena, June, Sewell, and Riley, *Nature Medicine*, 2008.

Table 2 shows sequence information for the sequences shown in FIG. 1. The sequence between Vβ and Vα is GSADDAKKDAAKKDGKS (SEQ ID NO:4) in the example shown.

TABLE 2

| Domain | SEQ ID NO: | Sequence |
|---|---|---|
| 1G4 Vβ13.1 | [SEQ ID NO: 38] | GVTQTPKFQVLKTGQSMTLQCAQDMNHEYMSWYRQDPGMGLRLIHYSVSVGMTDQGEVPNGYNVSRSTTEDFPLRLLSAAPSQTSVYFCASSYVGNTGELFFGEGSRLTVLEDLKN |
| 1G4 Vα23 | [SEQ ID NO: 41] | KQEVTQIPAALSVPEGENLVLNCSFTDSAIYNLQWFRQDPGKGLTSLLLIPFWQREQTSGRLNASLDKSSGTSTLYIAASQPGDSATYLCAVRPTSGGSYIPTFGRGTSLIVHPY |
| A6 Vβ13.1 | [SEQ ID NO: 39] | NAGVTQTPKFQVLKTGQSMTLQCAQDMNHEYMSWYRQDPGMGLRLIHYSVGAGITDQGEVPNGYNVSRSTTEDFPLRLLSAAPSQTSVYFCASRPGLMSAQPEQYFGPGTRLTVTEDLKN |
| A6 Vα2 | [SEQ ID NO: 42] | QKEVEQNSGPLSVPEGAIASLNCTYSDRGSQSFFWYRQYSGKSPELIMSIYSNGDKEDGRFTAQLNKASQYVSLLIRDSQPSDSATYLCAVTTDSWGKLQFGAGTQVVVTPD |
| 868 Vβ5.2 | [SEQ ID NO: 40] | EAGVTQSPTHLIKTRGQQVTLRCSPKSGHDTVSWYQQALGQGPQFIFQYVRGEERQRGNFPDRFSGHQFPNYSSELNVNALLLGDSALYLCASSDTVSYEQYFGPGTRLTVTEDLKN |
| 868 Vα2 | [SEQ ID NO: 43] | QKEVEQNSGPLSVPEGAIASLNCTYSDRGSQSFFWYRQYSGKSPELIMFIYSNGDKEDGRFTAQLNKASQYISLLIRDSKLSDSATYLCAVRGAHDYALNFGKGTSLLVTPHI |
| TRAV1 2-2 (Vα2) | [SEQ ID NO: 44] | QKEVEQNSGPLSVPEGAIASLNCTYSDRGSQSFFWYRQYSGKSPELIMFIYSNGDKEDGRFTAQLNKASQYVSLLIRDSQPSDSATYLC |
| TRAV1 2-1 (Vα2) | [SEQ ID NO: 45] | RKEVEQDPGPFNVPEGATVAFNCTYSNSASQSFFWYRQDCRKEPKLLMSVYSSGNEDGRFTAQLNRASQYISLLIRDSKLSDSATYLC |

The A6 and 868 both utilize the TRAV12 family (also called human Vα2), with primarily the characteristics of the TRAV12-2 subgroup (SEQ ID NO:44). For instance, both these wild-type affinity receptors share the same CDR1α and CDR2α residues. Despite this, there are some differences between the 868 and A6 Vα framework regions. The 868 TCR was originally selected from a phage display library using pools of random Vα chains in combination with Vβ chains (9). Once the Vα and Vβ of a HIV(GAG)-SL9 (SEQ ID NO:2)/HLA.A2 phage displayed TCR was isolated, similar Vα and Vβ usage was confirmed by antibody staining of the 868 CTL line which responded to SL9 (SEQ ID NO:2)/HLA.A2. Multiple attempts to clone the original 868 CTL by limiting dilution were previously reported to be unsuccessful. Hence, the residues with homology to TRAV12-1 (FIG. 1) may be artifacts of phage display engineering (9).

Figure 2A:
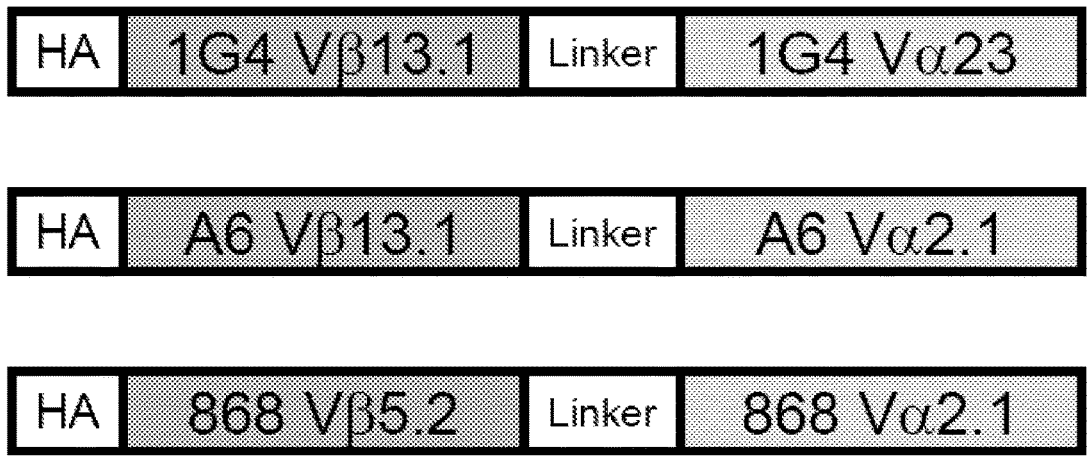
FIG. 2. Schematic of Yeast Surface Expressed Single-Chain TCRs. (A) Schematic of scTCRs expressed on the surface of yeast. 1G4 and A6 utilize the same Vβ gene family, and A6 and 868 use the same Vα gene family. 1G4 Vβ13.1 (SEQ ID NO:38), A6 Vβ13.1 (SEQ ID NO:39), 868 Vβ5.2 (SEQ ID NO:40), 1G4 Vα23 (SEQ ID NO:41), A6 Vα2 (SEQ ID NO:42), 868 Vα2 (SEQ ID NO:43), TRAV12-2 (Vα2) (SEQ ID NO:44) and TRAV12-1 (Vα2) (SEQ ID NO:45) are shown. (8) Yeast surface expression of scTCRs as monitored with an antibody to the N-terminal expression tag, followed by secondary antibody (HA, solid gray); secondary antibody only is the negative control (black line). Staining with peptide/MHC streptavidin:phycoerythrin tetramer. Null tetramer is shown (Gray line) as a control, along with the antigenic peptide/MHC tetramer ligand (black, solid). The antigenic peptides shown are NYESO (SEQ ID NO:5), Tax (SEQ ID NO:1) and SL9 (SEQ ID NO:2). The 868 scTCR is stable on the yeast cell surface without any additional mutations from the template.
Figure 2B:
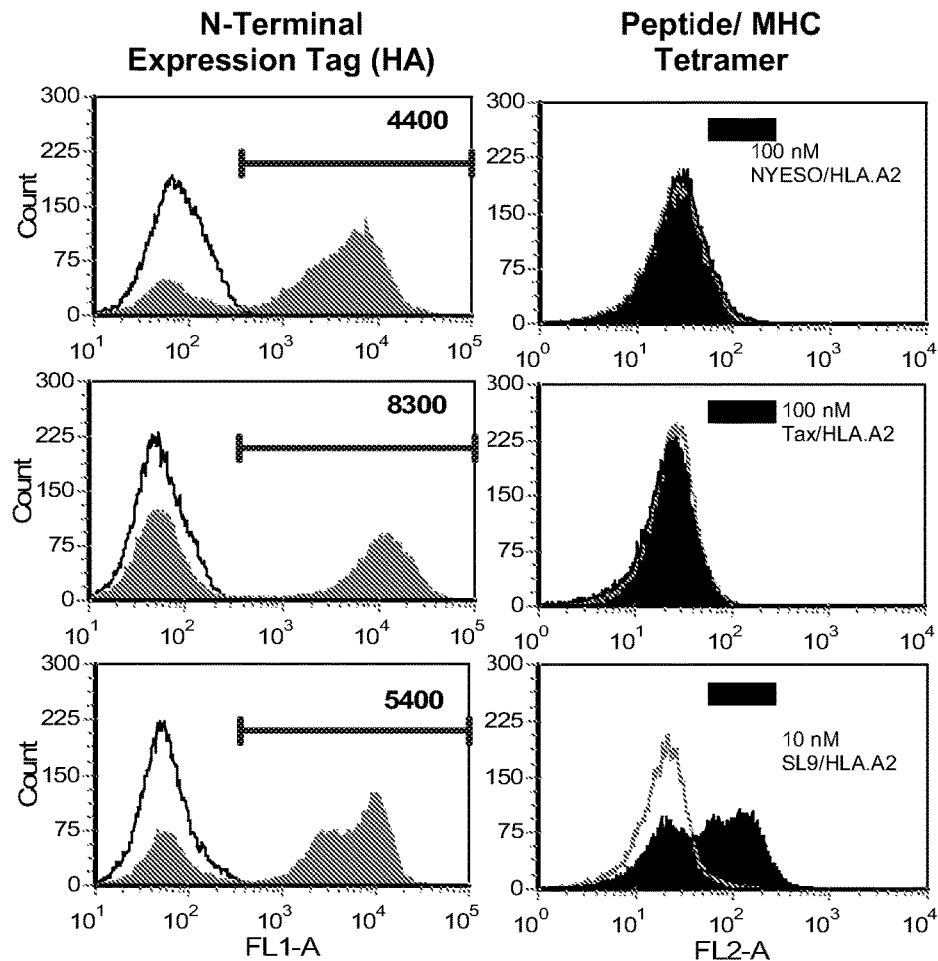

Previous successes engineering scTCRs have been predicated on the availability of a clonotypic antibody to detect yeast surface expressed protein. The variants of the 1G4, A6 and 868 TCRs selected using the full length TCR format containing the C regions have a relatively high affinity for pep:MHC. This should allow for the use of pep:MHC tetramers to detect surface expressed TCR, analogous to selections with a clonotypic antibody (6, 15). All three single-chain human T cell receptor variants (format shown in FIG. 2A) were introduced into the yeast display vector as a fusion to the Aga-2 yeast mating protein (FIG. 2). The 1G4 and A6 scTCRs were not detected with the pep:MHC tetramer, suggesting that these proteins were not stable on the surface of yeast (top and middle panels of FIG. 2B). The cells express a hemagglutinin (HA)N-terminal protein expression tag that was detected with an anti-HA antibody to confirm that the fusions were capable of being expressed on the surface of yeast, if their V domains were stable and folded properly. The cells were also not positive with an antibody to Vβ13, further confirming that the Vβ domain of these scTCR proteins were not expressed on the yeast surface (data not shown). This is consistent with previous observations by us and others that the yeast protein quality control apparatus does not prevent the export of misfolded proteins to the yeast cell surface (21). In contrast, the 868 scTCR was detected with the pep:MHC tetramer by flow cytometry (bottom panels of FIG. 2B), for the first time showing that a scTCR could be expressed on the yeast cell surface without mutations generated by random mutagenesis.

For comparison, the 1G4, A6 and 868 TCRs were also introduced into a full-length yeast display format, with the beta chain fused to the AGA-2 yeast mating protein and the alpha chain secreted. This construct contained a non-native cysteine to allow for improved ai3 pairing as previously described (11, 12). The high-affinity variants in the full-length TCR format bound to pep:MHC tetramer at detectable levels, suggesting that the affinity of the TCRs was sufficient to use pep:MHC tetramer as a probe for scTCR surface expression (see below), and that the lack of staining with the A6 and 1G4 scTCRs was due to a problem with V region stability in the absence of the C regions.

Figure 3A:
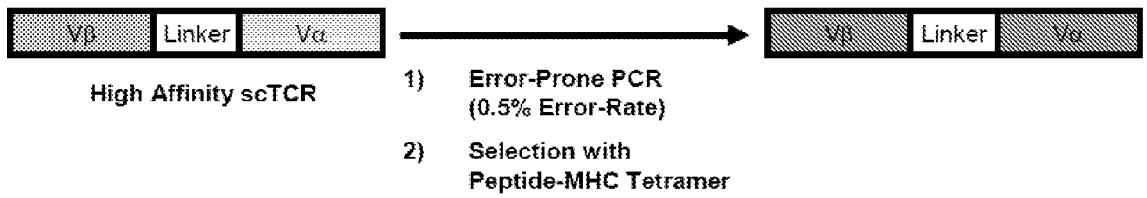
FIG. 3. Isolation of Stable Yeast Surface Expressed, High-Affinity scTCR Variants. Overview of engineering process for scTCRs. The scTCRs were synthesized (Genscript) and introduced into the yeast display vector. Mutagenesis by error-prone PCR and subsequent selection with pep:MHC tetramer after multiple rounds of fluorescence activated cell sorting (FAGS) allowed for isolation of stabilized, high-affinity scTCRs. Error prone PCR libraries of the A6 and 868 scTCRs were sorted by FAGS with soluble peptide/HLA.A2 PE tetramer to isolate stable, high affinity single-chain TCR expressing yeast cells. (8) A6 scTCR: The HTLV Tax (SEQ ID NO:1)/HLA.A2 specific scTCR (A6) expressing yeast were stained with an anti¬hemagglutinin antibody to monitor protein induction (gray solid), with secondary antibody only as a negative control (black line, left column of histograms). Surface expressed scTCR was monitored by phycoerythrin (PE) pep:MHC tetramer staining with 100 nM Tax (SEQ ID NO:1)/HLA.A2 (solid black) or 100 nM null peptide NYESO (SEQ ID NO:5)/HLA.A2 (gray line, right column of histograms). The A6 scTCR template (Vβ SEQ ID NO:39 and Vα SEQ ID NO:42) and A6-X15 (Vβ SEQ ID NO:50 and Vα SEQ ID NO:42) are shown. (C) 868 scTCR: Yeast expressing the 868 scTCR were stained with an anti-hemagglutinin antibody or secondary antibody only (Left column of histograms, Goat anti-Mouse FAb' 488) as in (B). The HIV Gag SL9 (SEQ ID NO:2)/HLA.A2 specific scTCR expressing yeast were stained with 10 nM SL9 (HIV-Gag, SEQ ID NO:2)/HLA.A2 (solid black, right column of histograms) or 10 nM null peptide Tax (SEQ ID NO:1)/HLA.A2 (gray line, right column of histograms). The 868 scTCR with high affinity CDR mutations was expressed at higher surface levels after selection of the scTCR with mutations (e.g. 868 clone Z11 (Vβ SEQ ID NO:53 and Vα SEQ ID NO:59) is shown) as monitored by SL9 (SEQ ID NO:2)/HLA.A2 tetramer binding.

Example 2. Engineering Surface Displayed scTCRs by Random Mutagenesis: TCR Against HTLV (Virus) Epitope To determine whether A6 and 1G4 scTCR mutations would enable expression on yeast cells, and whether the 868 scTCR could be mutated to facilitate higher levels of expression on yeast cells, the 1G4, A6, and 868 scTCRs were subjected to rounds of random mutagenesis and subsequently sorted with pep:MHC tetramer to isolate variants with improved surface expression (FIG. 3A). Despite multiple rounds of mutagenesis and sorting of the NYESO (SEQ ID NO:5) specific TCR 1G4, no stabilized variants were isolated. In contrast, stabilized mutants of the HTLV specific A6 scTCR and HIV specific 868 TCR were isolated after mutagenesis and fluorescence activated cell sorting, as described individually below.

Figure 3B:
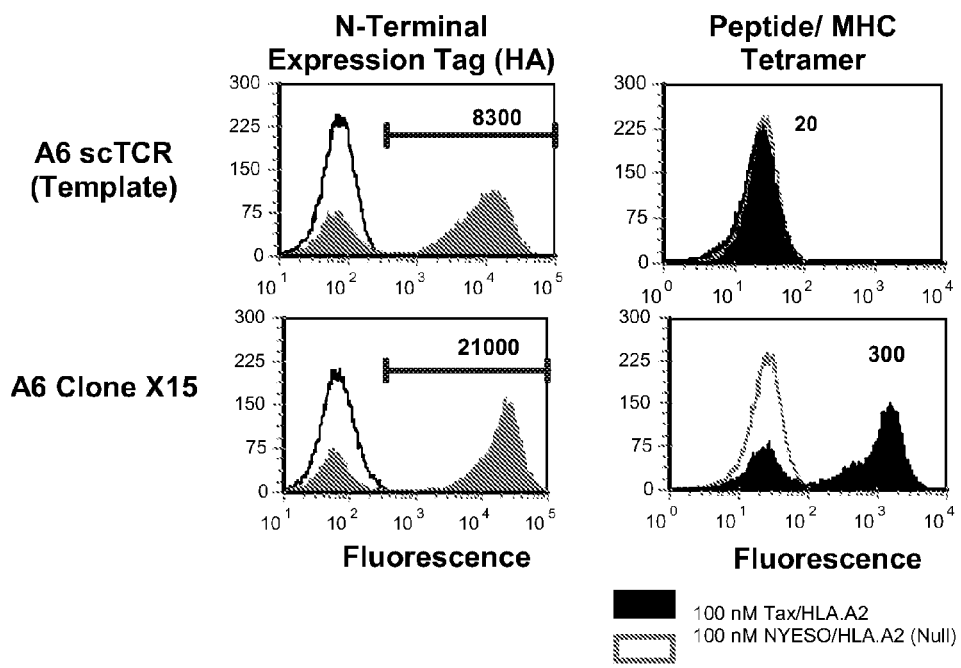
Figure 4:
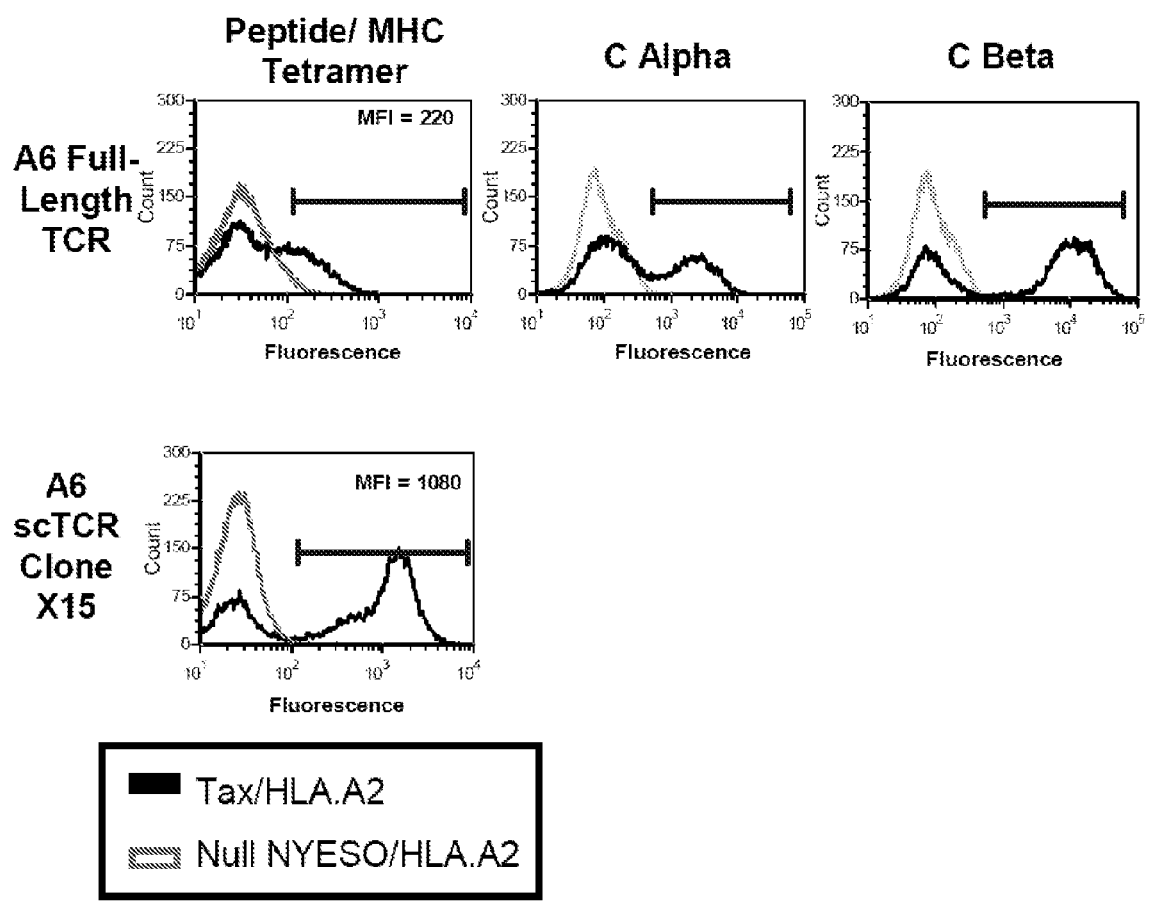
FIG. 4. Comparison of A6 Full Length Compared to Stabilized scTCR for Surface Levels. The full-length A6 TCR was expressed on the yeast cell surface with the β chain attached to the yeast cell surface mating protein Aga-2 and the α chain secreted as previously described (ref 12). A pair of mutations in the constant domains of the TCR to Cys (α:Thr48Cys, β:Ser57Cys) have been reported to facilitate formation of a non-native disulfide bond between the alpha and beta chain (ref 11). For Cα and Cβ (black), secondary antibody only (gray) was used as a control (Right two histograms, top row). The stabilized A6 scTCR with mutations (e.g. clone X15 (Vβ SEQ ID NO:50 and Vα SEQ ID NO:42)) allows for higher surface levels relative to the full-length construct as monitored by 100 nM Tax (SEQ ID NO:1)/HLA.A2 phycoerythrin tetramer (black). Null tetramer, 100 nM WT-1 (SEQ ID NO:6)/HLA.A2-PE (gray), is shown in peptide/MHC tetramer histograms (left column of histograms). Mean fluorescence intensity for the TCR surface expressing population is shown in the top right corner of peptide/MHC tetramer histograms.

A6 scTCR:

The HTLV Tax (SEQ ID NO:1) specific TCR A6 was sorted with Tax (SEQ ID NO:1)/HLA.A2 phycoerythrin tetramer to isolate variants that were expressed on the yeast surface. An error-prone PCR library was created across the entire A6 scTCR gene, with 0.5% error-rate (4-5 amino acid mutations/scTCR template). The yeast cells expressing the A6 error-prone PCR library were sorted five times with 100 nM Tax (SEQ ID NO:1)/HLA.A2 phycoerythrin tetramer, and the highest stability clone was subjected to a second round of mutagenesis. Previous experiments with the 2C TCR demonstrated that selection of scTCRs with increased resistance to thermal denaturation yielded mutants with significantly higher levels of display that correlated with soluble secretion efficiency (20). Consequently, the A6 library was sorted twice more, and after a third round of temperature stability selection two mutants with improved scTCR yeast surface levels called A6-X3 (Vβ SEQ ID NO:49 and Vα SEQ ID NO:51) and A6-X15 (Vβ SEQ ID NO:50 and Vα SEQ ID NO:42) were isolated that bound to Tax (SEQ ID NO:1)/HLA.A2 tetramer at detectable levels (FIG. 3B and data not shown). Both scTCR mutants were expressed at much higher surface levels than the A6 template scTCR, and the A6-X15 (Vβ SEQ ID NO:50 and Vα SEQ ID NO:42) was expressed at five times the level of the full-length TCR, as monitored by staining with pep:MHC tetramer (FIG. 4).

Figure 3C:
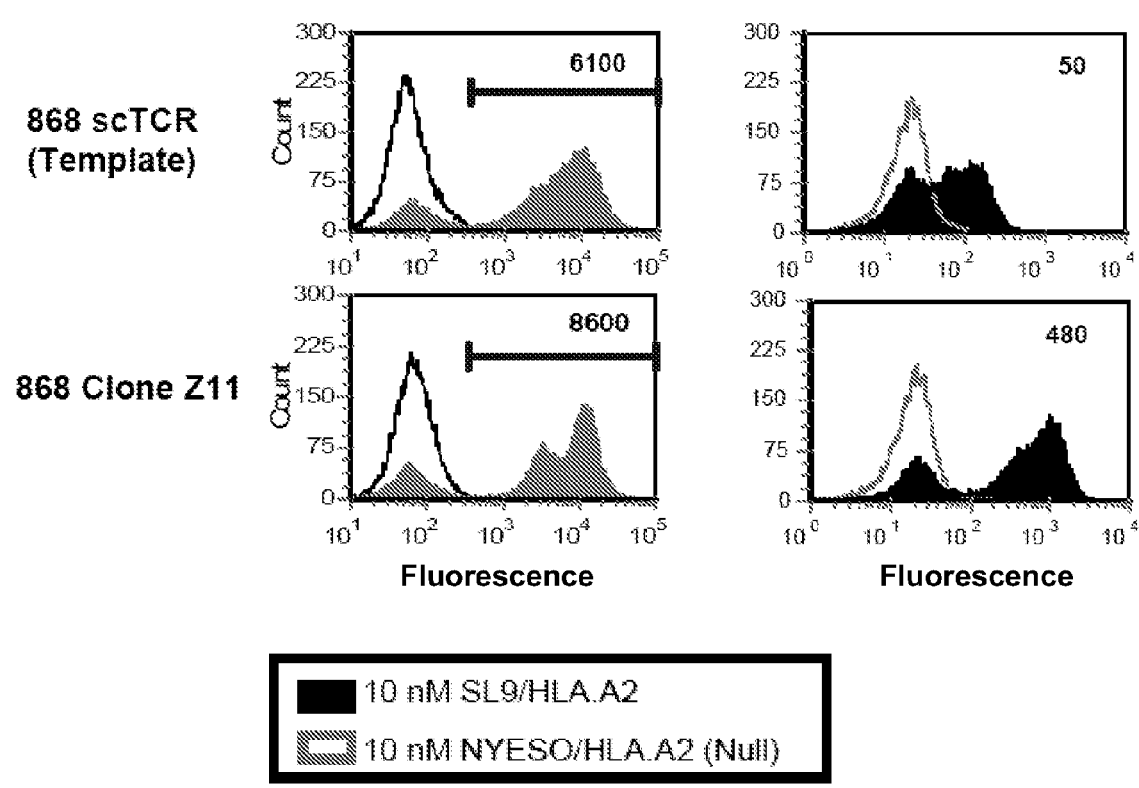
Figure 5:
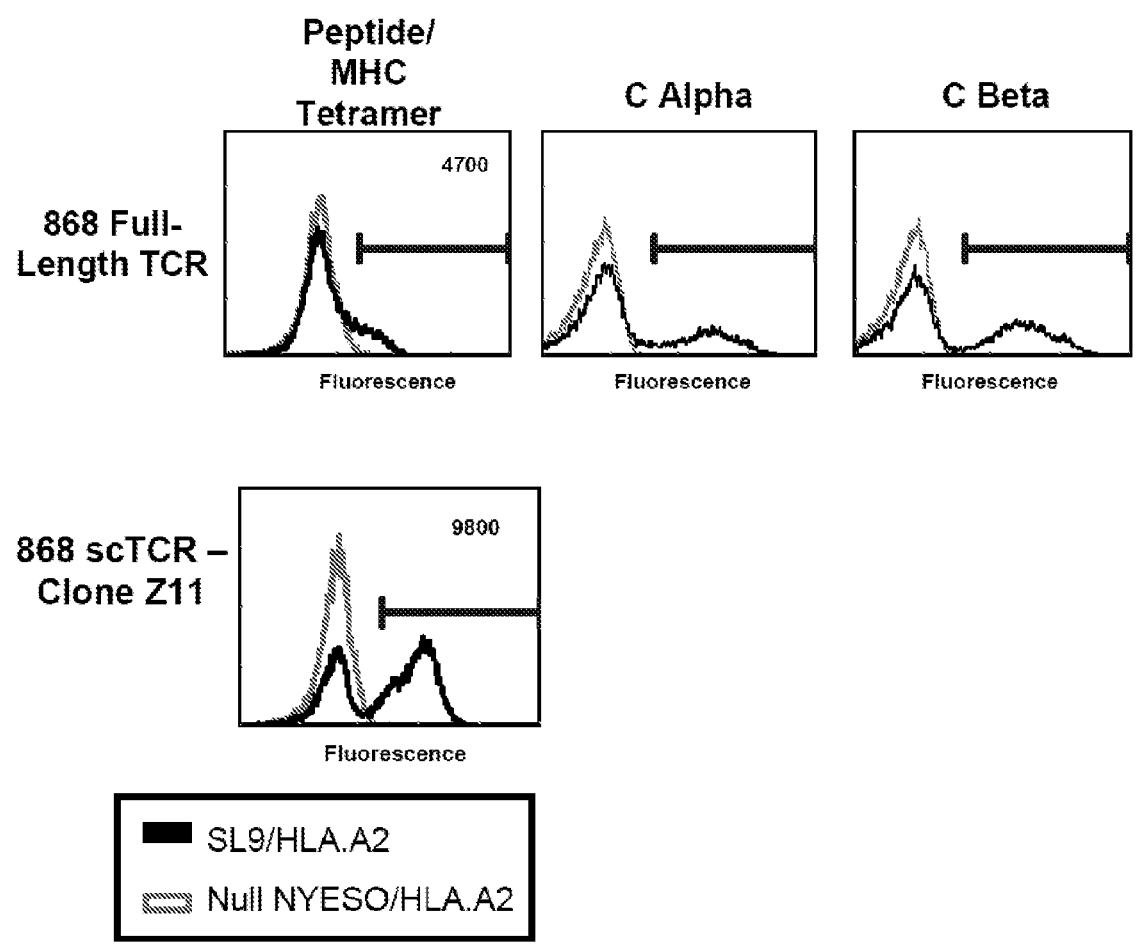
FIG. 5. Comparison of 868 Full Length Compared to Stabilized scTCR for Surface Levels. The full-length 868 TCR was expressed on the yeast cell surface with the β chain attached to the yeast cell surface mating protein Aga-2 and the α chain secreted as described for the A6 full-length TCR (FIG. 4). For Cα and Cβ (black), secondary antibody only (gray) was used as a control (Top row, right two histograms). The stabilized 868 scTCR (868-Z11 (Vβ SEQ ID NO:53 and Vα SEQ ID NO:59) allowed for higher surface levels relative to the full-length construct as monitored by 10 nM SL9 (SEQ ID NO:2)/HLA.A2 phycoerythrin tetramer (black). Null tetramer, 10 nM NYESO (SEQ ID NO:5)/HLA.A2-PE (gray), is shown in peptide/MHC tetramer histograms (Left column of histograms). Mean fluorescence intensity for the TCR surface expressing population is shown in the top right corner of peptide/MHC tetramer histograms.

Example 3. Engineering Surface Displayed scTCRs by Random Mutagenesis: TCR Against HIV (Virus) Epitope 868 scTCR:

For the HIV Gag (SL9 peptide, SEQ ID NO:2) specific 868 scTCR, we sought to improve the surface levels of the yeast-displayed protein by random mutagenesis (error-prone PCR) and temperature stability sorting. After two rounds of selection with pep:MHC tetramer and an additional round of temperature selection, a temperature stable, scTCR mutant called 868-Z11 (Vβ SEQ ID NO:53 and Vα SEQ ID NO:59) was isolated. The 868-Z11 mutant (Vβ SEQ ID NO:53 and Vα SEQ ID NO:59) bound to SL9 (SEQ ID NO:2)/HLA.A2 PE tetramer at concentrations as low as 1 nM as detected by flow cytometry (FIG. 3C and data not shown). 868 Z11 (Vβ SEQ ID NO:53 and Vα SEQ ID NO:59) also exhibited improved surface levels relative to the full-length 868 TCR expressed on the yeast cell surface (FIG. 5). This demonstrated that the single-chain format allows for higher surface levels of productively arranged Vβ-linker-Vα pairs relative to the full-length C region-containing format.

Example 4. A Single Mutation Near CDR2a Effects Vα and Vβ Domain Stability

Figure 6:
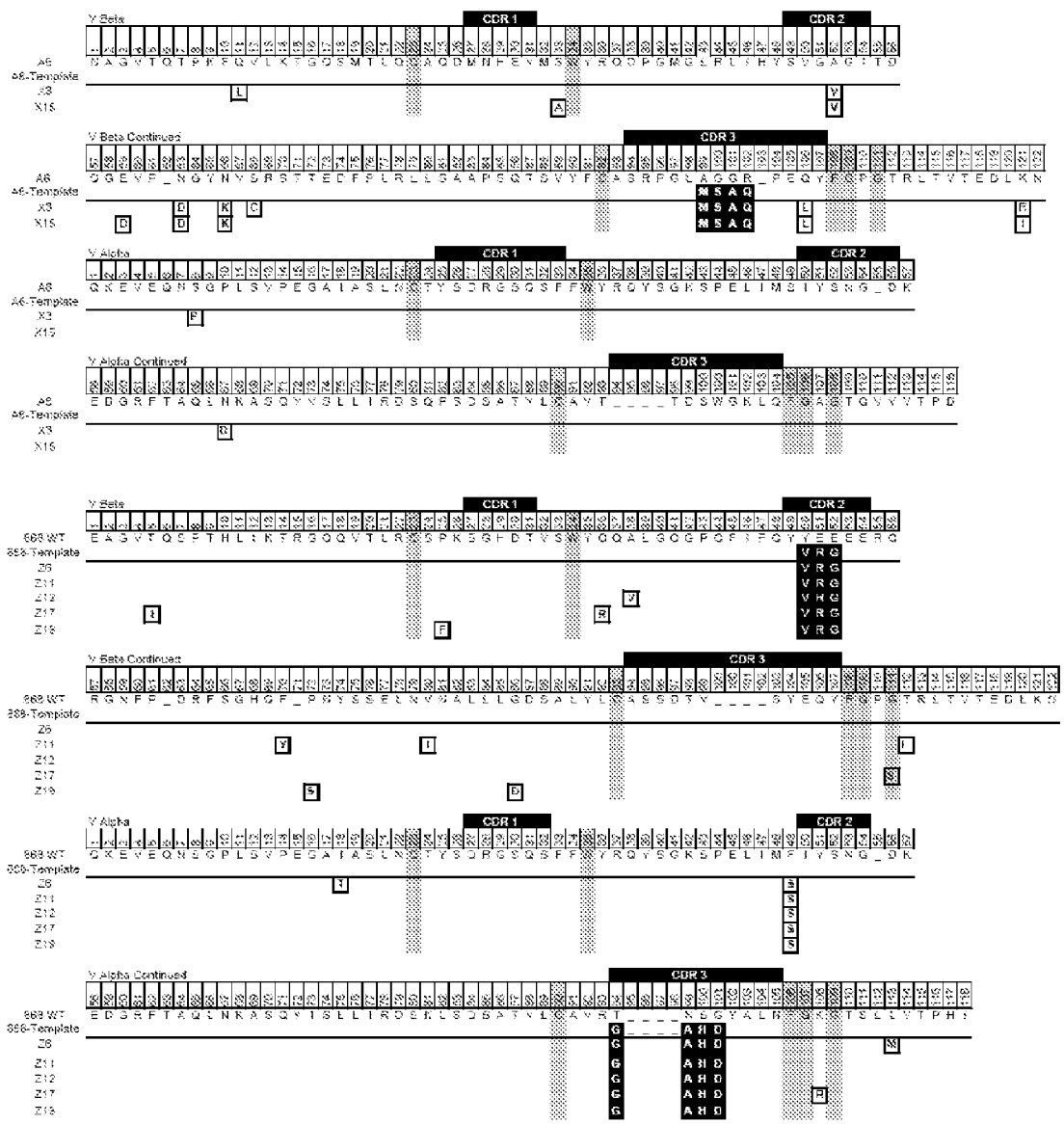
FIG. 6. Sequences of Stabilized scTCRs. Where no residue is shown for the template and stabilized clones, residue from the original A6 or 868 V region was retained in the sequence. Wild type A6 Vβ (SEQ ID NO:48), A6 template Vβ (SEQ ID NO:39), A6-X3 Vβ (SEQ ID NO:49), A6-X15 Vβ (SEQ ID NO:50), wild type A6 Vα (SEQ ID NO:42), A6 template Vα (SEQ ID NO:42), A6-X3 Vα (SEQ ID NO:51) and A6-X15 Vα (SEQ ID NO:42) are shown in FIG. 6A.

We then sought to analyze the specific mutations that contributed to improved surface levels for both A6 and 868, which utilize Vα2.1 (TRAV12-2). A6-X15 (Vβ SEQ ID NO:50 and Vα SEQ ID NO:42) did not contain any Vα mutations to improve stability, but it did contain mutations in the Vβ (FIG. 6). Thus, consistent with the results of the wild type 868 scTCR (Vβ SEQ ID NO:52 and Vα SEQ ID NO:57) expression, the native Vα2 region alone conferred adequate stability to allow surface expression of this V region domain.

The sequences of the 5 most stable 868 clones out of 20 isolated after temperature stability sorting (FIG. 6) demonstrated that there was only one Vα mutation, Phe$_{Vα49}$Ser, which was conserved among all variants. In addition, this was the only Vα mutation present in the most stable 868 clone isolated, clone 868-Z11 (FIGS. 3C and 5 (Vβ SEQ ID NO:53 and Vα SEQ ID NO:59)). This residue is identified as a phenylalanine in the IMGT nomenclature, but has been designated as a polymorphic residue for TRAV12-2 (Vα 2.1, SEQ ID NO:44). The A6 scTCR also utilizes TRAV12-2 (SEQ ID NO:44), but contains a serine at residue 49. Introduction of the Phe$_{Vα49}$Ser mutation into the 868 scTCR revealed that this single mutation provided the protein with improved resistance to thermal denaturation. The Phe$_{Vα49}$Ser mutation alone could provide adequate temperature stabilization and expression on the yeast surface (FIG. 7). However, additional mutations in the Vβ domain of clone Z11 could enhance surface levels slightly (FIG. 7).

Figure 8A:
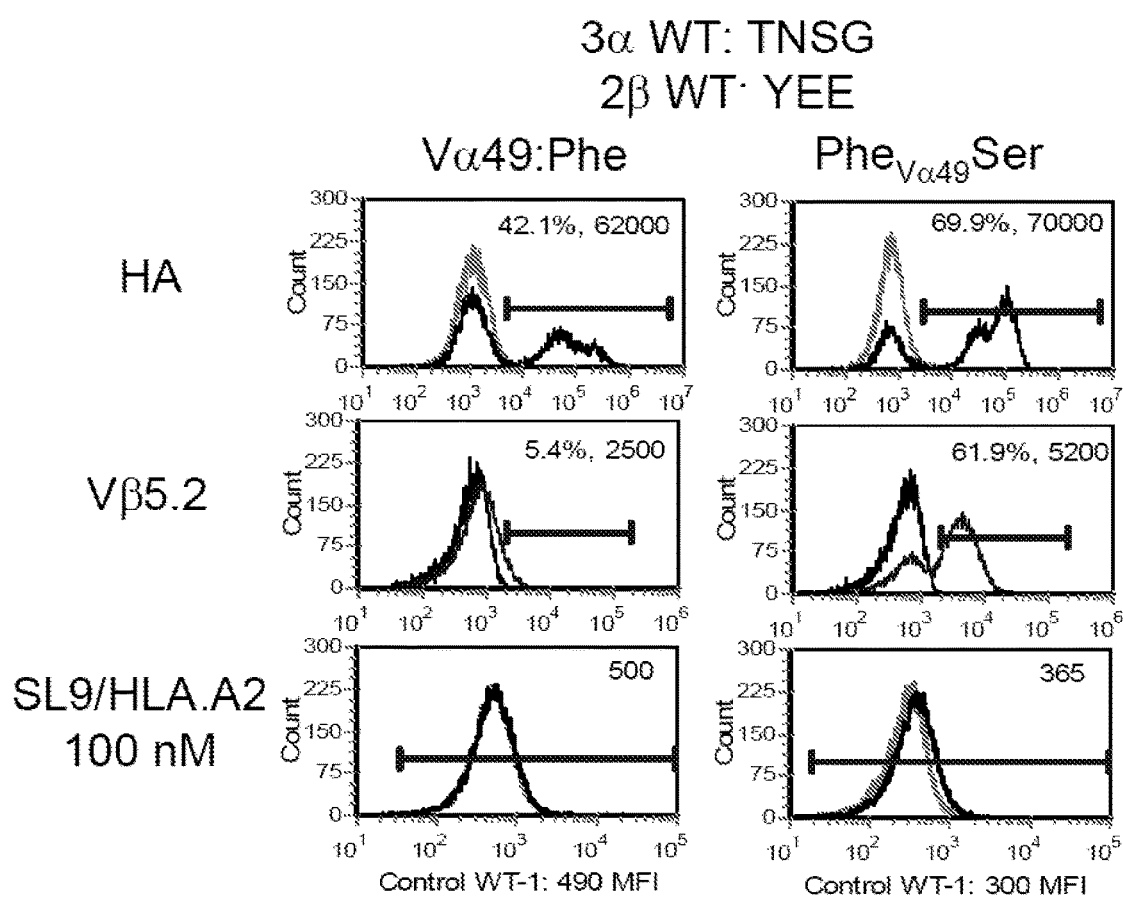
Figure 8B:
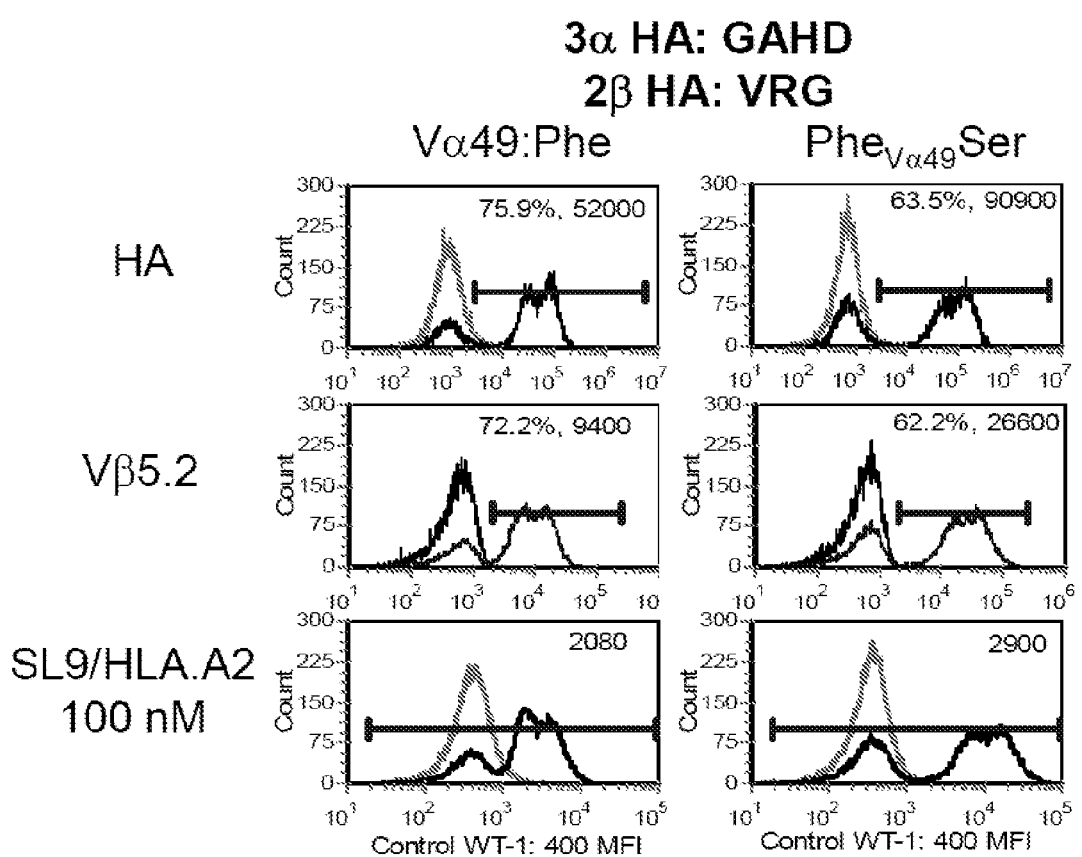

To further assess the impact of the Phe$_{Vα49}$Ser mutation, it was introduced into the 868 scTCR with the original wild type affinity CDR loop sequences as published (9). The 868 template (Vβ SEQ ID NO:40 and Vα SEQ ID NO:43) with the wild-type CDR loop residues is not of sufficient affinity to be monitored with pep:MHC tetramer by flow cytometry, so an antibody to the TCR Vβ domain was used to assess surface levels (FIG. 8). The addition of the Phe$_{Vα49}$Ser mutation alone conferred improved Vβ surface levels, showing that the single mutation allows for improved stability of the Vβ domain (FIG. 8A). It is important to note that the 868 scTCR contains 3 Vα residues that correspond to a different Vα2 subfamily (TRAV12-1, SEQ ID NO:45) (FIG. 1). The inability of the scTCR to be yeast surface expressed with wild-type CDR loops as monitored by anti-Vβ5.2 suggests that the residues derived from TRAV12-1 (SEQ ID NO:45) do not contribute to the improved stability of the 868 Vα2 domain to the same extent as the Pheva49Ser mutation. In the case of the 868 TCR with high affinity CDR mutations in both CDR2β and CDR3α (template for 868 scTCR engineering), the addition of Phe$_{Vα49}$Ser conferred improved scTCR surface levels (FIG. 8B). This demonstrated that Vα49:Ser is the only residue that is necessary from the 868 Vα2.1 domain to allow for improved thermal stability.

Example 5. Effects of Other CDR and Framework Mutations on scTCR Display

Figure 9A:
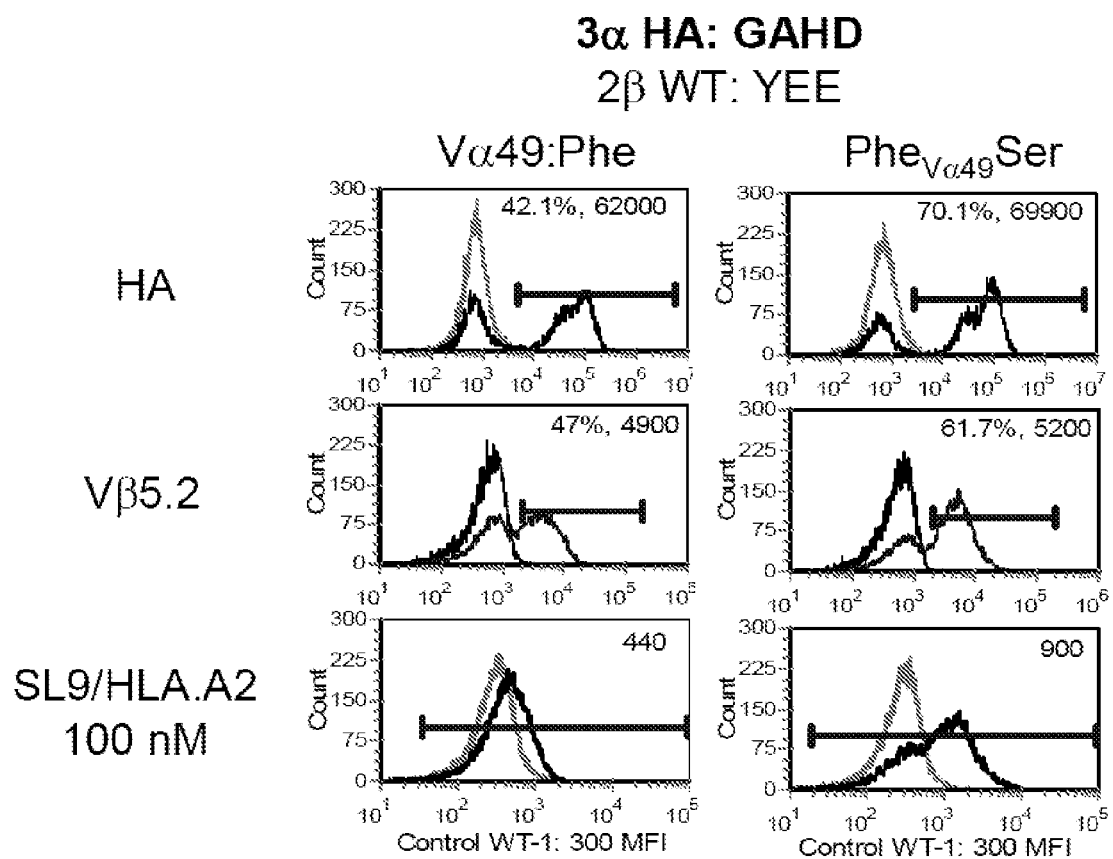

To further investigate other properties of the 868 scTCR that might confer this protein with exceptional stability, we analyzed the contribution of the CDR mutations that conferred higher affinity on the 868 scTCR. The wild-type CDR2β sequence and the wild-type CDR3α sequences (Table 1) were introduced into the template 868 scTCR (Vβ SEQ ID NO:40 and Vα SEQ ID NO:43) and yeast surface protein stability was monitored by pep:MHC tetramer. The high affinity mutations in CDR3α allow for improved Vβ surface levels as monitored with Vβ5.2, and improved Vα and Vβ stability as monitored by SL9 (SEQ ID NO:2)/ HLA.A2 tetramer staining (FIG. 9A). The surface levels of the protein were even further enhanced with the addition of the Phe$_{Vα49}$Ser mutation near CDR2a. This demonstrated that mutations within the Vα CDR3 region can improve the stability of complementary Vβ domains, but that even in this context the Vα2 region mutation is advantageous.

Figure 9B:
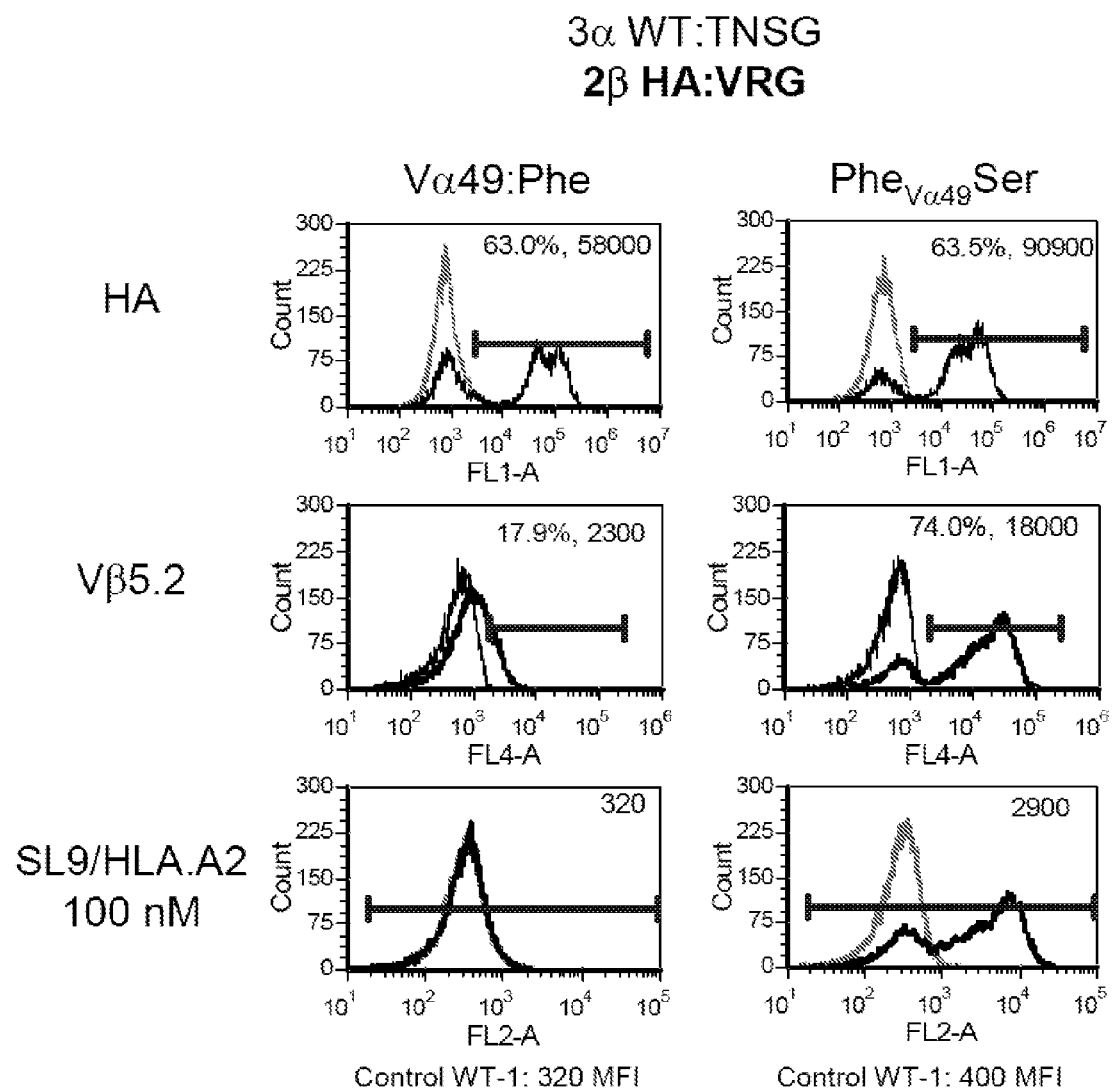

The mutations in CDR2β that alone conferred high affinity did not allow for complete stabilization of the Vβ domain, as no detectable tetramer or Vβ staining was observed (FIG. 9B). The Vβ5.2 antibody should still bind the high affinity CDR2β mutations, since the 868 scTCR, with high affinity mutations in both CDR3α and CDR2β is recognized by this antibody (FIG. 8). Thus, the mutations that confer high affinity in CDR2β do not contribute to the stability of the Vβ domain. The addition of the Phe$_{Vα49}$Ser mutation to the CDR2β high affinity variant (FIG. 9B) allow for surface display of the scTCR as monitored by SL9 (SEQ ID NO:2)/HLA.A2 tetramer, further suggesting that this single Vα mutation can stabilize the Vα and Vβ domains.

In the case of the A6 scTCR two residues in CDR2β and in CDR3β, Ala$_{Vβ52}$Val, and Gin$_{Vβ106}$Leu respectively, were mutated in all the isolated clones. In addition, the most stable A6 clones contained additional mutations in the Vβ framework 3 region. A6-X15 (Vβ SEQ ID NO:50 and Vα SEQ ID NO:42) contains three mutations within framework 3, two of which, Asn$_{Vβ62}$Asp and Asn$_{Vβ66}$Lys were conserved in the highest surface expressing clones (FIG. 4). The Vα2.1 domain of the A6-X15 (Vβ SEQ ID NO:50 and Vα SEQ ID NO:42) contained no mutations, despite maintaining high surface levels of scTCR capable of recognizing Tax (SEQ ID NO:1)/HLA.A2 tetramer (FIG. 3B).

Finally, it is important to point out that the only clone that did not express the Vα2 region, 1G4 (SEQ ID NO:41), was not able to be expressed as a scTCR, similar to many scTCRs that we have tested. Thus, the Vα2 region is exceptionally stable compared to other Vα regions, and it can be used in the context of different Vβ regions to generate scTCRs with different specificities (e.g. A6 and 868).

Example 6. Expression of Soluble Single-Chain TCRs in E. coli

Figure 10A:
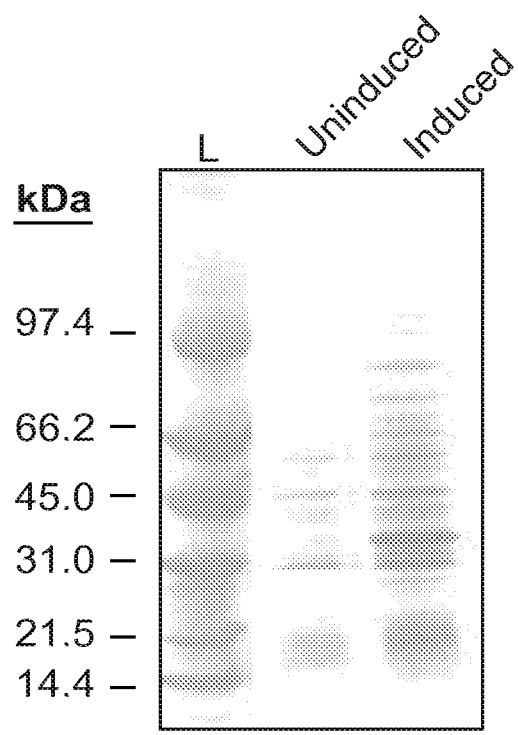

We have shown previously that the level of surface expression on yeast is directly correlated with the express levels of properly folded scTCR in yeast secretion system (20) or in E. coli (6, 22). The 868 scTCR mutant with improved resistance to thermal denaturation, 868-Z11 (Vβ SEQ ID NO:53 and Vα SEQ ID NO:59), was introduced into an E. coli expression vector for soluble expression and in vitro refolding. Accordingly, the 868 scTCR was cloned into an E. coli expression vector, transformed into E. coli, and inclusion bodies were harvested. The scTCR could be refolded in vitro, expressed and purified at milligram quantities per liter, and concentrated to >4 mg/mL (FIG. 10A and data not shown). For some of these experiments, the protein was labeled with biotin for detection purposes.

Example 7. Detection of Low Levels of HIV/HLA.A2 Complexes with Soluble scTCR 868

Figure 10B:
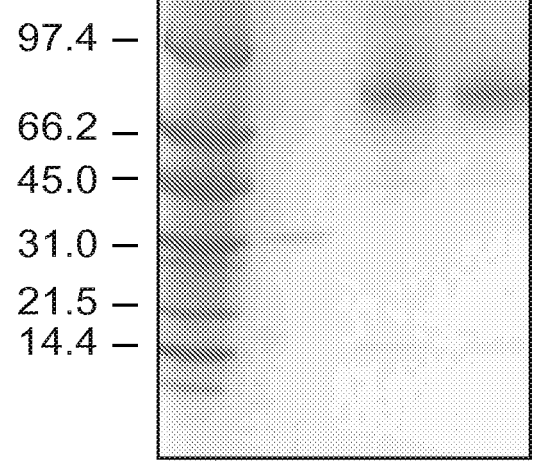
Figure 11A:
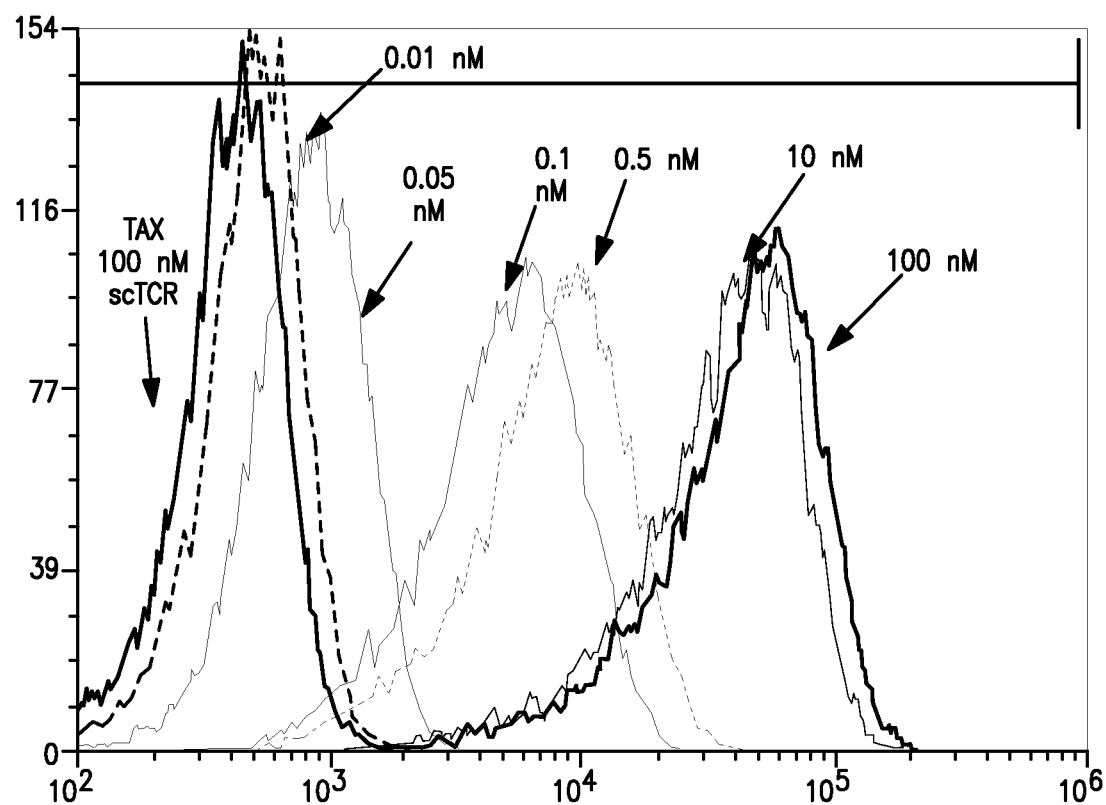
Figure 11B:
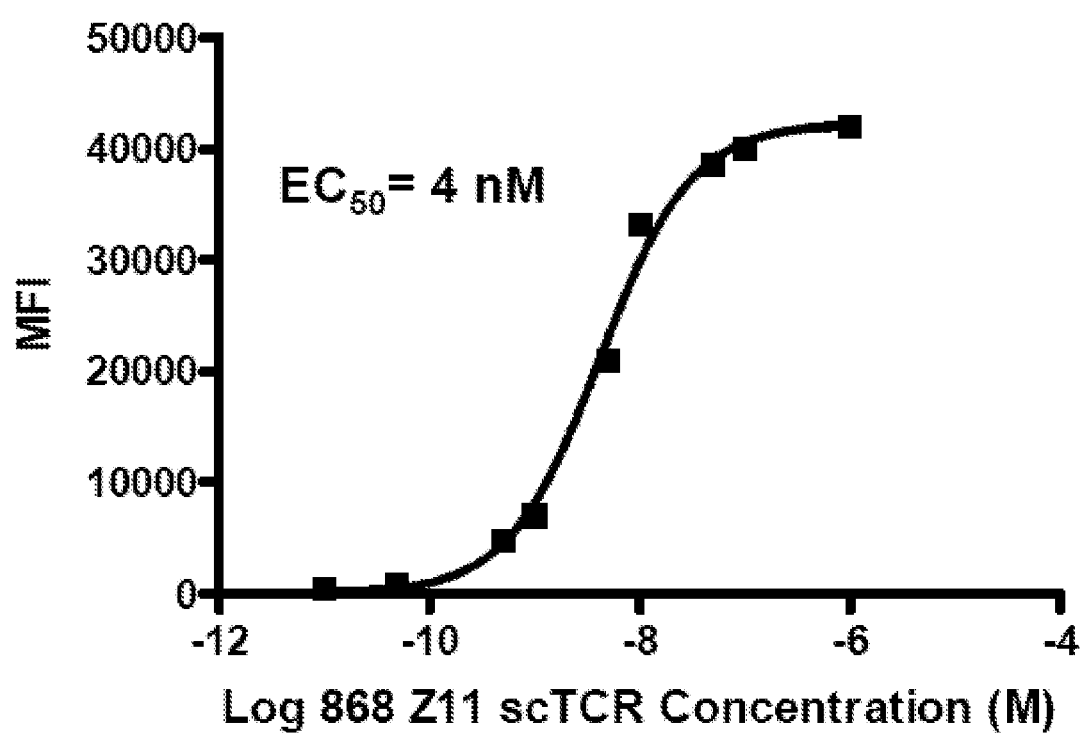
Figure 11C:
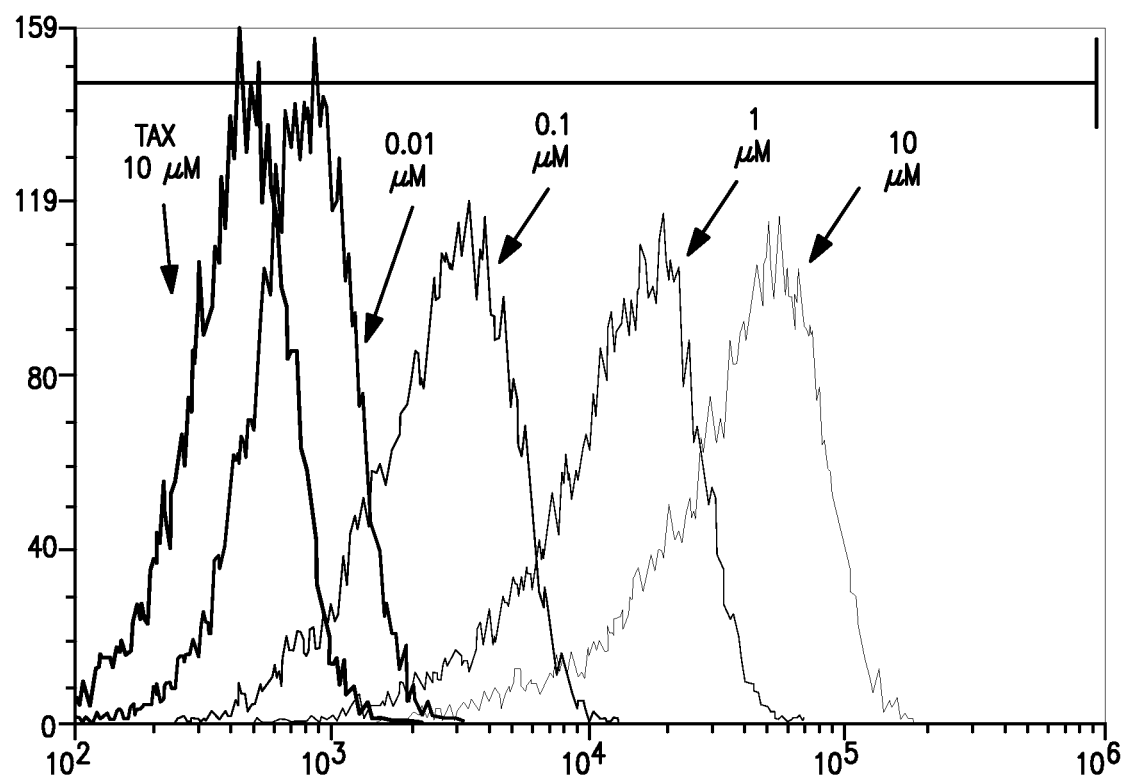

The 868 scTCR was subsequently biotinylated in vitro using Sulfo-NHS amide chemistry (EZ-Link Sulfo NHS Kit, Pierce) and percent biotinylation was estimated by streptavidin gel-shift on SDS-PAGE gels (FIG. 10B). The 868 scTCR linker (SEQ ID NO:4) contains >10 lysines which allow for multiple biotin sites per scTCR molecule. The 868 scTCR contains no lysine residues in CDR loops, and hence this modification should not effect the binding of the scTCR to pep:MHC. Using the TAP-deficient HLA.A2+ human cell line T2, SL9 peptide (SEQ ID NO:2) or Tax (null) peptide (SEQ ID NO:1) was loaded in excess (10 uM) on T2 cells for 2 hrs at 37° C., and cells were subsequently stained at a range of concentrations of biotinylated 868 scTCR followed by streptavidin:PE at room temperature (FIG. 11A). The soluble 868 scTCR detected T2 peptide loaded cells at scTCR concentrations as low as 0.1 nM. To estimate the binding affinity of the scTCR, the titration shown in FIG. 11A was plotted to calculate the half-maximal binding concentration ($EC_{50}$), which was 4 nM (FIG. 11B). To examine the sensitivity of binding in order to assess if this scTCR might be used in diagnostics with HIV infected cells, the SL9 peptide (SEQ ID NO:2) was titrated on T2 cells and the antigen presenting cells were stained with 868 biotinylated scTCR (FIG. 11C). The 868 scTCR could detect the peptide at concentrations as low as 10 nM, which represents an approximately 5-fold improvement in limit of detection by flow cytometry relative to the full-length 868 TCR variant described by Varela-Rohena et al (9).

Example 8. Single-Chain TCRs in Adoptive T Cell Therapies

To further demonstrate how a single-chain TCR can be used in a form that is advantageous as a therapeutic, the scTCR was cloned in a gene fusion construct for redirecting the activity of T cells (e.g. in an adoptive T cell approach). T cell receptor mispairing with endogenous TCRs has been proposed as a major hurdle for such adoptive therapy strategies (23, 24). To circumvent this issue, we sought to determine the effect of using three-domain TCR construct (Vα-linker-VβCβ) (FIG. 12) as has been previously reported (25), or the single-chain TCR constructs (Vα-linker-Vβ or Vβ-linker-Vα) that completely lack a C region. The single-chains in our example each contained the stabilizing mutations to facilitate enhanced TCR surface expression and thus antigen recognition. We introduced stabilizing mutations that were previously isolated by yeast display for creation of the 2C-T7 scTCR into the three domain and single-chain versions of the high affinity variant m33, which has a measured $K_D$ of 16 nM for SIY (SEQ ID NO:17)/$K^b$ (18). We also introduced the cysteine in the constant region of the β chain domain (11), as it has been suggested that this mutation would reduce the pairing with endogenous α chains that lack a corresponding mutation in the Cα domain (26). That is, we reasoned that the three domain TCR with a non-native cysteine in the constant β domain should limit mispairing with endogenous TCR that lack a complementary cysteine in close proximity to Cβ:Ser57Cys and prevent the formation of mixed ai3 heterodimers of unknown specificity as has been previously described (26),(27).

Although the three-domain M33 construct was expressed as evidenced by staining with the anti-Cβ antibody, this construct was unable to associate with CD3 subunits as evidenced by the absence of CD3ε on the surface of the transduced T cells (FIG. 12). In the absence of TCR surface expression, the T cell line lacking endogenous receptor will not express the CD3 subunits at the cell surface. The three domain TCR expressing cells were unable to release IL-2 in response to SIY peptide (SEQ ID NO:17) loaded antigen presenting cells even at the highest concentrations (data not shown), demonstrating that the three domain receptor was not able to recruit the T cell signaling machinery. More importantly, additional experiments demonstrated that the Cβ region containing the non-native cysteine (Cβ: Ser57Cys) did not prevent mis-pairing with an endogenous α chain. Thus, a form of an introduced TCR that contains a C region will not be able to completely eliminate problems with mis-pairing with endogenous TCR chains, and possible autoimmune consequences of this approach.

To avoid mis-pairing with endogenous TCR and facilitate TCR signaling, we subsequently created scTCR fusion proteins consisting only of the variable domains of the TCR as a single-chain construct (Vα-linker-Vβ). We also connected, by a flexible linker, the scTCR to C-terminal fusion of CD28, CD3ζ and LCK (FIG. 13). Previous work had demonstrated that three domain T cell receptors fused to CD28, CD3ζ and LCK were able to respond to antigen, albeit at high peptide concentrations, presumably through clustering of the TCR fusions which bring the protein kinase LCK into close proximity with immune tyrosine activation motifs (ITAMs) (25). The m33 scTCR construct was expressed on the surface of the T cells as evidenced by staining with an anti-Vβ antibody (F23.2) and binding to the pepMHC, SIY (SEQ ID NO:17)/$K^b$ but not to the null ligand OVA (SEQ ID NO:18)/$K^b$ (FIG. 14). Notably, the scTCR was expressed at approximately 3-fold higher surface levels than the full-length receptor, suggesting that the smaller size of the extracellular portion of the scTCR fusion, or perhaps the lack of requirement for limiting CD3 subunits, allowed for improved surface expression and potentially improved membrane mobility (FIG. 14).

The m33 scTCR-CD28, CD3 LCK expressing T cells were also able to respond to SIY peptide (SEQ ID NO:17) at similar concentrations to the full-length αβ m33 expressing T cells, with no reactivity to OVA (null) peptide (SEQ ID NO:18) loaded antigen presenting cells (FIG. 15). This example of expression of a single-chain TCR, consisting of only the variable domains of a TCR, expressed on the surface of a T cell suggests that stabilized scTCRs have advantages over C region containing formats, for adoptive therapy applications.

Example 9. Effectiveness of High-Affinity Single-Chain TCRs in Adoptive T Cell Therapies To establish the role of increased affinity on activation of scTCR expressing T cells, the wild type 2C scTCR with stabilizing mutations was introduced into the CD28, CD3ζ LCK fusion construct. Like the high-affinity m33 scTCR, the 2C scTCR fusion was also expressed at increased surface levels relative to the full-length 2C 043 TCR as detected with the anti-Vβ antibody and the clonotypic antibody 1B2 (FIG. 16). scTCR construct were expressed at 5-10 fold higher surface levels with an anti-Vβ8 antibody (FIG. 16B). The increased levels of scTCR surface expression presumably contributed to improved binding to pepMHC tetramer, despite the relatively low affinity for the 2C scTCR for SIY (SEQ ID NO:17)/$K^b$ (FIG. 16C, tetramer staining at 40 nM and FIG. 16D, tetramer titration). The increased level of expression also presumably contributed to the ability of the 2C scTCR fusion to bind to the peptide-MHC tetramer despite the relatively low affinity of the 2C scTCR for SIY (SEQ ID NO:17)/$K^b$ (FIG. 16).

Despite the increased surface levels, the 2C scTCR CD28, CD3, LCK expressing T cells released only low levels of IL-2 at the highest SIY peptide (SEQ ID NO:17) concentrations. In contrast, the T cells expressing the 1000-fold higher affinity m33 scTCR fusion are activated at peptide concentrations as low as 1 nM (FIG. 17). The decrease in activity for the 2C scTCR relative to the m33 scTCR fusion is due to affinity, as the scTCR is expressed on the surface at similar levels as monitored by anti-mouse Vβ8 and the scTCR expressing T cell lines are both activated by plate bound mouse Vβ8 antibody F23.2 (FIG. 18). Notably, the scTCRs were not activated by plate bound anti-CD3 since no extracellular CD3 subunits were presented on the cell surface with the scTCR (FIG. 18), although the full-length constructs were activated by anti-CD3 antibodies, as expected. Thus, the scTCR format by passes the need for association with intracellular CD3 subunits.

Figure 19A:
Figure 19B:
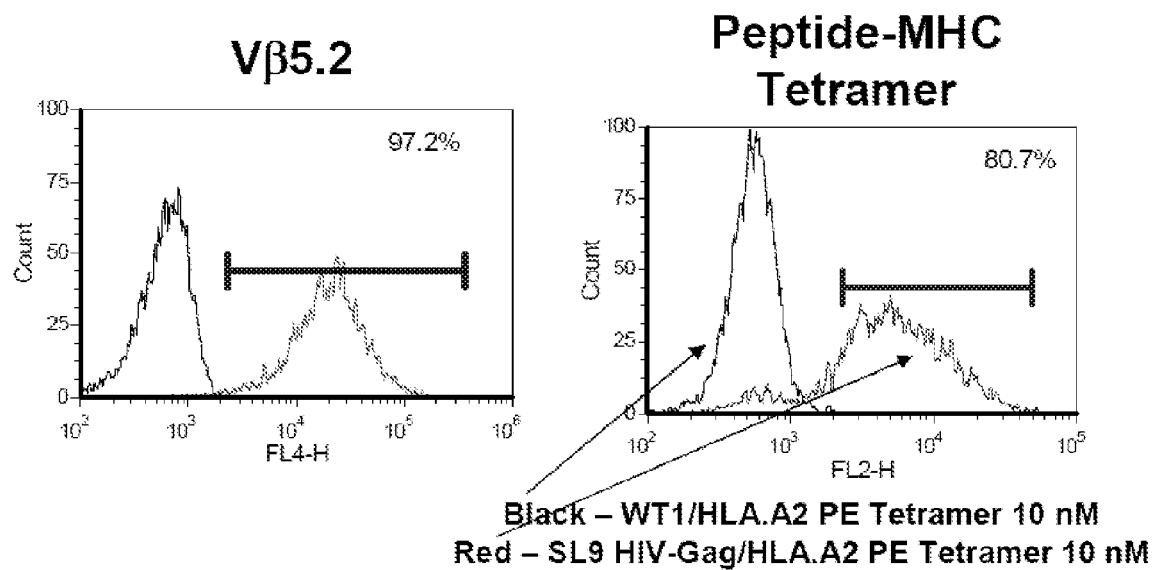
Figure 19C:
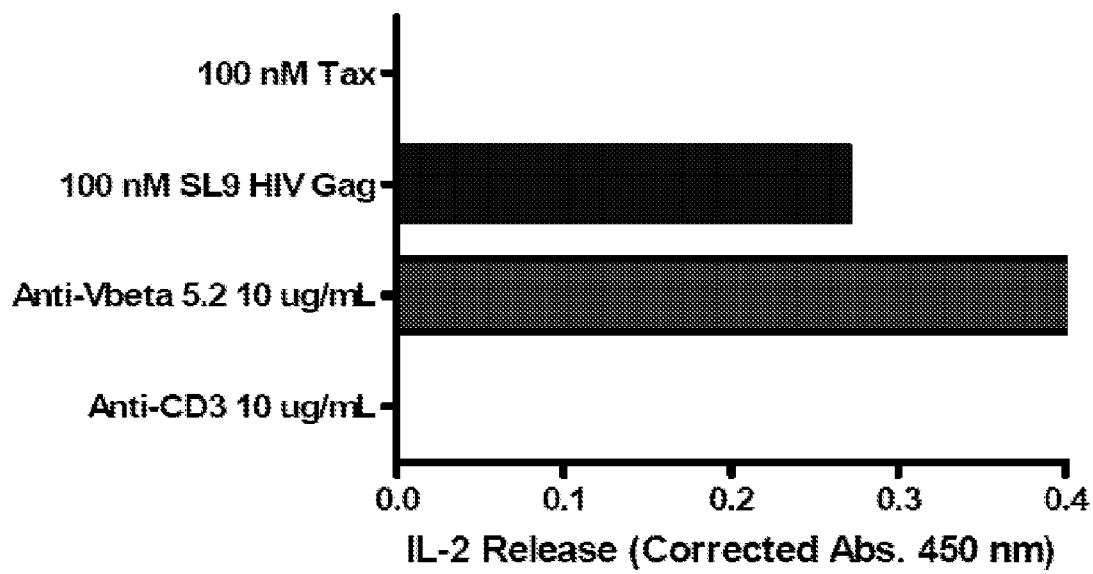
Figure 19D:
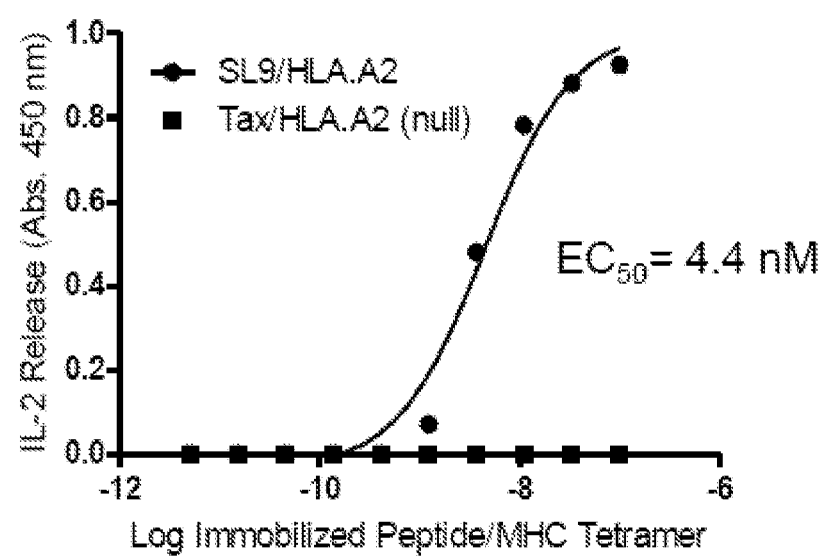

To show that this system would work with another scTCR, we introduced the stabilized human scTCR Vα2+ 868-Z11 (Vβ SEQ ID NO:53 and Vα SEQ ID NO:59) into the CD28, CD3ζ, LCK fusion construct in the MSCV retroviral vector (FIG. 19A). The 868-Z11 fusion protein was expressed on the surface of the T cells as monitored by binding to anti-human Vβ5.2 antibody and SL9 (SEQ ID NO:2)/HLA.A2 streptavidin PE tetramer at 10 nM (FIG. 19B). The utility of a human 868 scTCR fused to CD28, CD3, LCK was further demonstrated by the ability of T cells transduced with this receptor to respond to SL9 HIV peptide (SEQ ID NO:2)-pulsed HLA.A2 positive cells, but not those pulsed with the negative control peptide Tax (SEQ ID NO:1) (FIG. 19C). 868 scTCR fusion expressing T cells were also able to respond to plate-bound HIV-Gag/HLA.A2 pepMHC tetramer with an $EC_{50}$ of ~4 nM, whereas no activity was observed with the null Tax (SEQ ID NO:1)/HLA.A2 pepMHC tetramer (FIG. 19D). This data suggests that a similar fusion consisting of the analogous human intracellular signaling subunits would be capable of redirecting human T cells in adoptive therapy applications while avoiding the problems associated with TCR mis-pairing. Other Vα2+ TCRs engineered for improved stability can easily be introduced into this system because of the placement of a restriction site in the CD8α hinge region upstream of the transmembrane region of the CD28, CD3ζ, LCK fusion.

It is also important to note that there many other signaling constructs that have been tested in various systems, including early clinical trials, and which are amenable to our single-chain TCR format. These systems have relied largely on the use of single-chain Fv for testing (28), but the stabilized scTCR can be formatted in the same manner. These include recent constructs that contain the CD137 (4-1 BB) signaling domain in order to facilitate proliferation of the T cells (29-32).

In summary we demonstrate the surface expression of scTCRs in mouse and human high affinity TCR systems. Fusion of these scTCRs to intracellular cell signaling components allows for activation independent of cellular pools of LCK, which has been proposed to be a major hurdle in the redirection of TCRs derived from CD4+ T cells. The lack of a constant domain in these constructs will also avoid problems associated with mis-pairing between endogenous TCRs and introduced C-region containing receptors.

Discussion

In this study we have successfully engineered two human single-chain T cell receptors for improved stability using yeast display. The 868 and A6 TCRs, specific for peptides derived from viral proteins bound to the common human MHC allele HLA.A2, both utilize the TRAV12 family. We also attempted to engineer another high affinity TCR for improved stability in a scTCR format, the NYESO (SEQ ID NO:5) tumor antigen specific 1G4 TCR. However, repeated attempts to isolate stabilized 1G4 scTCRs were unsuccessful despite this receptor using the same Vβ gene as A6 (Vβ13.1, TRBV6-5). The A6 and 868 TCRs represent the first two human scTCRs engineered for improved stability, neither of which requires more than one mutation in the variable alpha domain for stable expression. To date, every single-chain TCR engineered for improved stability has required mutations in the Vα domain for yeast surface expression, and most scTCRs are not able to be stabilized adequately ((10) and data not shown). The use of the same Vα region in these stabilized scTCRs and a single mutation in the Vα domains of the stabilized versions (A6 X15 (Vβ SEQ ID NO:50 and Vα SEQ ID NO:42) and 868 Z11 (Vβ SEQ ID NO:53 and Vα SEQ ID NO:59)) of these two receptors suggest that Vα2 is exceptionally stable in comparison to other human Vα that have been tested. The findings are widely applicable, as it has been shown that T cells against other antigens, such as the melanoma antigen Melan-A (MART1, SEQ ID NO:61)/HLA-A2, frequently use the Vα2 region (33, 34). Therefore, the use of the techniques described here are used to produce a scTCR which binds with high affinity to a ligand which includes a peptide known as MART-1 (SEQ ID NO:61) expressed by melanoma.

The 868 TCR is the first single-chain TCR to be yeast surface expressed without additional stabilizing mutations. The mutation of a single Vα residue, $Phe_{V\alpha49}Ser$, also allowed for enhanced stable expression of the 868 scTCR after temperature challenge and improved expression of both the Vα and Vβ domains even when the wild-type affinity CDR loops were introduced into the construct as monitored by the Vβ5.2 antibody. This is especially $Phe_{V\alpha49}Ser$ $Phe_{V\alpha49}Ser$ improves pep:MHC tetramer staining and anti-Vβ5.2 staining of yeast surface expressed scTCR. It is remarkable, and quite unexpected, that a single mutation in the Vα domain can control the stability of both the Vα and Vβ domains.

The single mutation, $Phe_{V\alpha49}Ser$, may also provide an advantage in full-length TCR constructs for adoptive therapy strategies directed against HIV. The formation of mismatched α and β chain heterodimers between endogenous TCR and introduced TCR in adoptive T cell therapies has been proposed as a major hurdle for adoptive therapy. Such mismatched receptors could create new αβ. TCR heterodimers of unknown specificity (35, 36). The use of non-native cysteine residues within the TCR constant domains has been demonstrated to reduce mispairing (26, 27), but it may be necessary to create mutations within TCR variable domains to further promote the formation of the desired TCR on the surface of primary T cells. The presence of polymorphisms within TCR variable domains is one plausible explanation for the formation of dominant or strong TCR αβ heterodimers as have been described in multiple studies (37, 38). It is possible that TCRs which use Vα2 may act as dominant receptors in vivo due to the exceptional stability of receptors that use this alpha domain. Accordingly, the $Phe_{V\alpha49}Ser$ mutation may further allow the full-length 868 TCR to avoid the mis-pairing problem.

Previously, we have demonstrated that stabilizing mutations for scTCRs (Vβ-Linker-Vα) can be localized to the Vα:Vβ interface, the V:C interface, and the hypervariable-4 region of the Vβ domain (12). Although the $Phe_{V\alpha49}Ser$ mutation lies somewhat at the interface of the Vα and Vβ domains, this mutation could not have been predicted from these earlier studies. An additional residue located at the Vα:Vβ interface was mutated in all A6 stabilized scTCR clones isolated, $Gin_{V\beta106}$ ILeu. The position of this $Gin_{V\beta106}$ ILeu residue, which is within the CDR3β loop, is analogous to one of the stabilizing mutations present in the 2C scTCR (2C-T7) stabilized protein: 2C $Leu_{V\alpha104}$ Pro (15). The Leuvaio4Pro is at the Va:Vβ interface of the TCR, distal to the cell membrane. However, it is difficult to generalize the $Gin_{V\beta106}$ ILeu mutation to other Vβ domains paired with Vα2, as the stabilized version of the 868 scTCR contains a Gln residue at Vβ106 and this is the most variable region in a TCR it is difficult to predict the influence of other adjacent residues.

Results with the human scTCRs also allow us to propose a fourth possible area where stabilizing mutations can be isolated, within the T-cell receptor complementarity determining (CDR) loops. The high-affinity CDR mutations contribute to the stability of the 868 scTCR, with the CDR3α mutations providing the scTCR with improved stability relative to the CDR2β mutations. The ability of the high affinity CDR mutations to provide the scTCR with Vβ and Vα domain stability, even when only the CDR3α loop is mutated suggests that these mutations possibly stabilize the scTCR through increased interactions between the Vα and Vβ domains. These interactions most likely arise from close contacts between the CDR loops in each chain, but are difficult to predict without a crystal structure of the 868 TCR. In addition, the improved stability A6 scTCRs variants all contained a mutation within CDR2β: $Ala_{Vβ52}Val$. This mutation is required for the stabilization of the A6 scTCR. The requirement for the CDR2β mutation in A6, along with the data demonstrating that CDR3α mutations can stabilize the 868 scTCR, provide evidence that mutations within CDR loops can also contribute to scTCR stability.

The exceptional stability of the 868 scTCR allows for soluble expression of large quantities of this scTCR. The ability to produce soluble forms of this scTCR should make this protein amenable to use in many different formats for both diagnostics and therapeutics. Other T cell receptors derived from different T cell clones have been characterized for binding to SL9 peptide (SEQ ID NO:2) variants, with little cross-reactivity observed for other irrelevant peptides (39). However, the receptor characterized in that study had a much lower affinity for pep:MHC relative to the high affinity 868 variant selected for this study. The ability of HIV specific TCRs to react with SL9 peptide (SEQ ID NO:2) variants has been proposed to be important for controlling viral load, and it is probable that the increased affinity of 868 could be advantageous in controlling HIV progression (9, 40). Hence, the soluble version of the 868 scTCR has applications as a soluble therapy in strategies similar to those used with monoclonal antibodies. For example, the production of fusion proteins of the 868 scTCR to cytokines may allow for improved control of viral load and prevention of HIV immune escape.

The soluble 868 scTCR and other Vα2 containing scT-CRs also have applications as diagnostic probes. The ability to detect HIV derived peptides on the surface of APCs at lower levels of antigen may allow this protein to be used for detection of HIV infected cells, or in the quantification of SL9 (SEQ ID NO:2) MHC complexes in different stages of HIV infection. By using a lysine rich linker that can be modified to contain multiple biotin sites per molecule, the soluble scTCR can detect low numbers of pep:MHC on the surface of antigen presenting cells. The amplification of signal from a single scTCR may provide an advantage in detection of low numbers of antigen on target cells, as recent work has demonstrated that scTCR multimers are inefficient in detecting low numbers of antigen (41).

In summary, we demonstrate the exceptional stability of human Vα2 (TRAV12) as evidenced by the engineering of two human scTCRs. This finding, and the identification of the $Phe_{Vα49}Ser$ mutation, could not have been predicted based on any sequence or structural considerations. The stability of scTCRs that use Vα2 in soluble form also suggests that this gene family should be a target for the development of soluble therapeutics such as scTCR cytokine fusions. These soluble, MHC-restricted TCRs could be used in therapeutic strategies much like monoclonal antibodies. The discovery that Vα2 is exceptionally stable has additional implications for adoptive therapy strategies. If future adoptive therapy strategies will rely on redirecting T cells to tumor or viral antigens, it will be necessary to generate high affinity receptors from CD8+ T cells to generate an effective immune response. Clearly, the exceptional stability of Vα2 expressing TCRs will make this family of receptors more amenable to affinity maturation in vitro using single-chain TCR formats, and T cell clones with different specificities that use Vα2 can be isolated and used as described here.

Materials and Methods

Antibodies, Peptide/HLA.A2 Tetramer, and Staining for Flow Cytometry

Antibodies used to detect yeast surface expression include: anti-human Vβ 5.2, clone 1C1 (Thermo Scientific), anti-HA eptiope tag clone HA.11 (Covance), anti-human Cβ clone 8A3 (Endogen/Pierce), anti-human Cα clone 3A8 (Endogen/Pierce), goat anti-mouse IgG F(ab')$_2$ AlexaFluor 488 secondary antibody (Invitrogen), goat-anti-mouse IgG F(ab')2 AlexaFluor 647 secondary antibody (Invitrogen), and streptavidin-phycoerythrin (SA:PE, BD Pharmingen). Peptides that bind to HLA.A2 ($Tax_{11-19}$: LLFGYPVYV (SEQ ID NO:1), $NYESO-Val_{157-165}$: SLLMWITNV (SEQ ID NO:5), $SL9_{77-85}$ (HIV-Gag): SLYNTVATL(SEQ ID NO:2), and $WT-1_{126-134}$: RMFPNAPYL(SEQ ID NO:6)) were synthesized by standard F-moc (N-(9-fluorenyl) methoxycarbonyl) chemistry at the Macromolecular Core Facility at Penn State University College of Medicine (Hershey, Pa.). HLA.A2 heavy-chain was produced as inclusion bodies and refolded in vitro with HLA.A2 binding peptides and human b-2 microglobulin as described (42). The HLA.A2 heavy chain contains a biotinylation substrate sequence which allows for in vitro biotinylation (Avidity, BirA enzyme) and subsequently for formation of strepavidin:phycoerythrin peptide/MHC tetramer. All tetramer and antibody staining of yeast cells was performed on ice for 45 mins using ~$1 \times 10^6$ cells. Cells were subsequently washed with 500 mL PBS/BSA (0.5%) and analyzed by flow cytometry with an Accuri C6 flow cytometer.

TCR Selection and Yeast Display of Single-Chain T Cell Receptor

The genes for T cell receptors were synthesized by Genscript (Piscataway, N.J.) with the variants isolated for improved affinity by phage display. These receptors were originally isolated using a full-length TCR display format with a non-native disulfide bond. The 1G4 variant (clone C49, C50, $K_D$=1.3 nM) specific for NYESO (SEQ ID NO:5) (19), the A6 variant (clone 134, $K_D$=2.5 nM) specific for Tax (SEQ ID NO:1)/HLA.A2 from human T cell lymphotrophic virus (7), and the 868 variant ($K_D$ of at least 10 nM) specific for human immunodeficiency virus Gag SL9 (SEQ ID NO:2)/HLA.A2 peptide (9) were ordered as single-chain T cell receptors (Table 1, Valpha/Vbeta Usage), consisting of the variable domains attached by a lysine rich linker region (GSADDAKKDAAKKDGKS SEQ ID NO:4). For the 868 variant, the most prevalent clone listed from CDR2β (Bold: high affinity mutations, Sequence: YVRGEE SEQ ID NO:7) and CDR3α (Sequence: CAVRGAHDYALN SEQ ID NO:8) libraries was selected, since the sequence of the highest affinity clone was not specified (9). The Val-Arg-Gly mutations in CDR2β provide at least a 14-fold improvement in dissociation constant, suggesting the dissociation constant for the 868 variant used is at least 10 nM (wild-type affinity 868 TCR KD=143 nM). The scTCRs containing CDR mutations that confer high affinity for peptide/HLA.A2 were introduced into the yeast display vector pCT302 using NheI and XhoI restriction sites. The scTCRs in pCT302 were then used as templates for error-prone PCR with 0.5% error-rate as described (43). Mutagenized PCR products were produced and electroporated along with NheI and XhoI digested vector into yeast strain EBY100 to generate libraries of at least ~1×10$^7$ transformants by homologous recombination.

For construction of full-length TCR constructs, the scTCR genes as synthesized were introduced into the human full-length VαCα and VβCβ as described (11, 12). In brief, the Vβ domains of 868 and A6 were introduced into the p315 plasmid as a fusion to AGA-2 by ligation into NheI and BglII restriction sites. The BglII site was introduced into the Cβ domain as described (11). The Vα domain was introduced into the pCT302-sec plasmid into NheI and BamHI sites with the BamHI site introduced into the Cα domain. Full-length TCR constructs contained a non-native Cys in each constant domain (α: Thr48Cys, β: Ser57Cys) to facilitate formation of a disulfide bond. The cysteine residues that normally participate in the interchain disulfide bond in the stalk region were replaced with a stop codon. In addition, the free Cβ cysteine at position 71 was mutated to a serine (Cβ: Cys71Ser).

scTCRs and VβCβ for full-length TCR constructs were expressed from yeast display plasmid pCT302 (Vβ-L-Vα scTCRs) (44) or p315 (VβCβ generously provided by Dane Wittrup and colleagues, MIT) which contain a galactose-inducible AGA2 fusion and allow for growth in Trp-media or Leu-media respectively. VαCα for full-length TCR constructs was expressed from pCT302-sec, which contains a galactose inducible secretion construct and allows for growth in Trp-media. Surface expression of TCR constructs was performed by transferring EBY100 yeast that had been transformed with plasmid and grown to stationary phase in selection media to galactose containing media to drive expression from the galactose-responsive promoter.

Yeast Display scTCR Libraries, Sorting and Characterization of Improved Stability scTCRs Libraries were generated for the A6, 868, and 1G4 scTCR, and expanded for 2 days in dextrose (SD-CAA) growth media. Cells were switched to galactose containing media (SG-CAA) for 48 hours and then washed with 500 mL 0.5% PBS/BSA. Cells were subsequently stained on ice with corresponding pep:MHC tetramer (Table 1) at 100 nM, which is of sufficient affinity to detect TCRs with $K_D$ values on the order of 1 nM if properly processed and presented on the cell surface. Cells were washed once in 5 mLs 0.5% PBS/BSA to remove unbound pep:MHC ligand, and the most fluorescent cells were selected on MoFlo (Cytomation) or FAGS Aria (BD Bioscience) high speed sorters. Yeast libraries were subjected to an additional round of temperature stability sorting where yeast were preincubated at increased temperature (A6: 42° C. for 45 minutes, 868 40° C. for 30 min) prior to staining of cells on ice. The percent collected and pertinent details of each sort are provided below.

A6 scTCR.

5 Sorts on initial error-prone Library: Sort 1: top 0.5%, 500,000 cells, Sort 2: top 0.5%, 210,000 cells, Sort 3: top 0.5%, 150,000 cells, Sort 4: top 0.5%, 100,000 cells, Sort 5: top 0.5%, 100,000 cells. After 5 sorts, a clone was isolated that showed detectable binding to peptide:MHC tetramer. This clone was then used as a template for an additional round of error-prone mutagenesis. The second error-prone library was sorted twice: Sort 2-1: top 0.5%, 300,000 cells, Sort 2-2: top 10%, 1,000,000 cells. Sort 2-3: after induction in galactose containing media, preincubated yeast at 42° C. in water bath for 45 minutes and then stained with Tax (SEQ ID NO:1)/HLA.A2 tetramer at 100 nM for 45 minutes on ice and collected top 0.7%, 350,000 cells. Individual yeast cell clone were selected from the population isolated after this sort and tested for resistance to thermal denaturation at 40° C. (Clones X1-X20).

868 scTCR.

1 Sort on initial error-prone library and 1 round of temperature stability sorting. Sort 1: top 2%, 500,000 cells, Sort 2: after induction in galactose containing media, preincubated yeast at 40° C. in water bath for 30 minutes, stained with Tax (SEQ ID NO:1)/HLA.A2 tetramer at 100 nM for 45 minutes on ice, and collected the top 0.5%, 21,000 cells. Cells were expanded in selection media and individual yeast clones were isolated and tested for resistance to thermal denaturation at 40° C. (Clones Z1-Z20).

Cloning of 868 scTCR Variants for Analysis of Contribution to Stability

The Phe$_{V\alpha49}$Ser mutation was introduced using Quikchange Lightning Kit (Stratagene, Agilent Technologies) with forward primer: 5' GGTAAATCTCCA GAATT-GATCATGTCCATCTACTCTAATGGTGACAAAGAAG 3' (SEQ ID NO:9) and reverse complement primer: 5' CTTCTTTGTCACCATTAGAGTAGAT GGACATGAT-CAATTCTGGAGATTTACC 3' (SEQ ID NO:10). The 868 scTCR with CDR2β (Sequence: YYEEEE, SEQ ID NO:11) and CDR3α (Sequence:CAVRTNSGYALNFG, SEQ ID NO:12) wild-type residues was synthesized by Genscript. The high affinity mutations for each CDR were introduced into this template by splicing by overlap extension (SOE) PCR (45).

scTCR Soluble Expression and Binding to Peptide Loaded APCs

The 868 Z11 mutant with high affinity mutations in CDR2β and CDR3α was introduced in the single-chain format into the pET28a expression vector using NcoI and EcorI (Forward primer: 5'TATACCATGGGCAGCAGC-CATCATCATCATCAT CACAGCAGCGGCCTGGTGC-CGCGCGGCAGCGAAGCTGGTGTTACTCAATCTC C 3' (SEQ ID NO:13) Reverse primer: AAATGAATTCT-TAAATATGTGGAGTAACCCAAAAAGAAG TACC (SEQ ID NO:14)). Protein was produced in BL21 cells, cells were passed through a microfluidizer and protein was harvested as inclusion bodies as described (46). Protein was refolded from inclusion bodies and purified with Ni agarose resin (Qiagen, Valencia, Calif.) followed by gel filtration (Superdex 200). The refolded protein was biotinylated through amine groups on lysine residues using N-hydroxy-succinimide (NHS) activated biotins which react with primary amine groups to form amide bonds (EZ-Link Sulfo-NHS-LC-Biotin Kit, Pierce/Thermo Scientific). The biotinylated protein was verified by gel-shift with streptavidin.

For soluble scTCR binding assays, T2 cells were incubated for 2 hrs with excess (10 mM) or a range of concentrations of SL9 (SEQ ID NO:2) or null Tax peptide (SEQ ID NO:1). Subsequently, cells were washed 2× to remove excess peptide with 0.5% PBS/BSA and then stained at room temperature for 30 minutes with biotinylated 868 scTCR at indicated concentrations. The cells were washed 2× with PBS/BSA (200 uL/wash) and then stained with SA:PE for 30 min. at room temperature. Cells were washed twice more and analyzed using an Accuri C6 Flow Cytometer.

Creation of Three Domain TCRs and scTCR Fusion Proteins

The murine CD28 transmembrane, CD3 zeta, LCK intracellular portion of the fusion protein (from sequence: Pubmed Accession # AY452130.1, GenBank: AAS07035.1)

and the M33 Vα-linker-VβCβ three domain TCR were independently synthesized by Genscript (Piscataway, N.J.). The genes for the three domain TCR were introduced into the murine stem cell virus (MSCV) retroviral vector using AgeI and MluI restriction sites. In addition to the CDR loop mutations that confer m33 with enhanced affinity for m33 (3α: LHRPA (SEQ ID NO:15)), the 2C variants described contain stabilizing mutations from the 2C-T7 scTCR (15). For the M33 scTCR fusion protein, the Vα-linker-Vβ region of the three domain construct was amplified by PCR and attached to the CD28, CD3 LCK gene by introduction of the hinge region of CD8α using splicing by overlap extension PCR (primers from IDT DNA, amino acid sequence of M33 scTCR fusion protein attached). Mutations to the wild-type affinity CDR3α (3α: GFASA (SEQ ID NO:16)) of the 2C scTCR were introduced by splicing by overlap extension PCR using the M33 scTCR fusion as a template. For creation of the 868 human scTCR fusion, the 868 clone Z11 scTCR (Vβ-linker-Vα) was amplified by PCR. The leader sequence added to this fusion protein was derived from the 2C Vα leader. The 868-Z11 scTCR with the 2C Vα leader was introduced into the AgeI and XhoI sites present in the M33 scTCR fusion protein.

Packaging Line, Transduction, and Surface Expression of Fusion Proteins in T Cell Hybridomas The PLAT-E packaging line was transfected with 30-40 ug of DNA for each construct. In brief, $2 \times 10^6$ PLAT-E cells were plated in a 10 cm dish the night prior to transfection. DNA was introduced into packaging line using Lipofectamine 2000 (Invitrogen) and cells were incubated with transfection mix for 4 to 6 hours in serum free media. After 4-hour incubation, cells were quenched with 6 additional mLs IMDM. 12 hours later, transfection mix was removed and cells were placed into 6 mLs RPMI (T cell media) for an additional 24 hours. Subsequently, $1 \times 10^6$ 58-/- hybridoma T cells were spinfected at 24° C. for 45 minutes with 1.5 mLs filtered retroviral supernatant with 6 uLs lipofectamine 2000. Cells were sorted twice for surface expression and subsequently used in T cell activation assays as has been previously described (18).

Equilibrium Binding to Peptide-MHC Tetramers

All equilibrium binding experiments to peptide-MHC tetramer were performed at 4° C. $1 \times 10^5$ T cells were incubated with SIY (SEQ ID NO:17)/$K^b$ or OVA (SEQ ID NO:18)/$K^b$ tetramer for 1 hr 4° C. For the 868 scTCR, $1 \times 10^5$ T cells were incubated with 10 nM SL9 HIV Gag (SEQ ID NO:19)/HLA.A2 or 10 nM WT-1 (SEQ ID NO:20)/HLA.A2 SA:PE tetramer for 1 hour at room temperature. Cells were washed 3× with 500 mL of 0.5% PBS/BSA, and flow cytometry was performed. Peptide sequences: SIY (SIYRYYGL (SEQ ID NO:17)), OVA (SIINFEKL (SEQ ID NO:18)), SL9 HIV-Gag (SLYNTVATL (SEQ ID NO:19)), WT-1 (RMFPNAPYL (SEQ ID NO:20)).

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art or to use methods or materials that are in the state of the art without the specific inclusion of the methods or materials in the disclosure herein. For example, when a compound is claimed, it should be understood that compounds known in the prior art, including certain compounds disclosed in the references disclosed herein (particularly in referenced patent documents), are not intended to be included in the claim.

When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of substances are intended to be exemplary, as it is known that one of ordinary skill in the art can name the same substances differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, target ligands, biologically active groups, starting materials, and synthetic methods other than those specifically exemplified can be employed in the practice of the invention without resort to undue experimentation. All art-known functional equivalents, of any such methods, target ligands, biologically active groups, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

The exact formulation, route of administration and dosage can be chosen by the individual physician in view of the patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of to thereby describe further embodiments that are not necessarily coextensive. For clarification, as used herein "comprising" is synonymous with "having," "including," "containing," or "characterized by," and is inclusive or open-ended and does not exclude additional, unrecited elements or method steps. As used herein, "consisting of excludes any element, step, component, or ingredient not specified in the claim element. As used herein, "consisting essentially of does not exclude materials or steps that do not materially affect the basic and novel characteristics of the claim (e.g., not affecting an active ingredient). In each instance herein any of the terms "comprising", "consisting essentially of and "consisting of may be replaced with either of the other two terms. The invention illustratively described herein suitably may be practiced in the absence of any element or elements, limitation or limitations which is not specifically disclosed herein.

The invention has been described with reference to various specific and preferred embodiments and techniques. However, it should be understood that many variations and modifications may be made while remaining within the spirit and scope of the invention. It will be appreciated by one of ordinary skill in the art that compositions, methods, devices, device elements, materials, optional features, procedures and techniques other than those specifically described herein can be applied to the practice of the invention as broadly disclosed herein without resort to undue experimentation. All art-known functional equivalents of compositions, methods, devices, device elements, materials, procedures and techniques described herein; and portions thereof; are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. Some references provided herein are incorporated by reference herein to provide details concerning additional starting materials, additional methods of synthesis, additional methods of analysis and additional uses of the invention.

One skilled in the art would readily appreciate that the present invention is well adapted to carry out the objects and obtain the ends and advantages mentioned, as well as those inherent therein. The compositions and methods and accessory methods described herein as presently representative of preferred embodiments are exemplary and are not intended as limitations on the scope of the invention. Changes therein and other uses will occur to those skilled in the art, which are encompassed within the spirit of the invention.

The reference numbers in the following list correspond to the numbers herein.
1. Rudolph, M. G., R. L. Stanfield, and I. A. Wilson. 2006. How TCRs bind MHCs, peptides, and coreceptors. *Annu Rev Immunol* 24:419-466.
2. Starr, T. K., S. C. Jameson, and K. A. Hogquist. 2003. Positive and negative selection of T cells. *Annu Rev Immunol* 21:139-176.
3. Stone, J. D., A. S. Chervin, and D. M. Kranz. 2009. T-cell receptor binding affinities and kinetics: impact on T-cell activity and specificity. *Immunology* 126:165-176.
4. Holler, P. D., P. O. Holman, E. V. Shusta, S. O'Herrin, K. D. Wittrup, and D. M. Kranz. 2000. In vitro evolution of a T cell receptor with high affinity for peptide/MHC. *Proc Nati Acad Sci USA* 97:5387-5392.
5. Holler, P. D., L. K. Chlewicki, and D. M. Kranz. 2003. TCRs with high affinity for foreign pMHC show self-reactivity. *Nat Immunol* 4:55-62.
6. Weber, K. S., D. L. Donermeyer, P. M. Allen, and D. M. Kranz. 2005. Class II restricted T cell receptor engineered in vitro for higher affinity retains peptide specificity and function. *Proc Natl Acad Sci USA* 102:19033-19038.
7. Li, Y., R. Moysey, P. E. Molloy, A. L. Vuidepot, T. Mahon, E. Baston, S. Dunn, N. Liddy, J. Jacob, B. K. Jakobsen, and J. M. Boulter. 2005. Directed evolution of human T-cell receptors with picomolar affinities by phage display. *Nat Biotechnol* 23:349-354.
8. Dunn, S. M., P. J. Rizkallah, E. Baston, T. Mahon, B. Cameron, R. Moysey, F. Gao, M. Sami, J. Boulter, Y. Li, and B. K. Jakobsen. 2006. Directed evolution of human T cell receptor CDR2 residues by phage display dramatically enhances affinity for cognate peptide-MHC without increasing apparent cross-reactivity. *Protein Sci* 15:710-721.
9. Varela-Rohena, A., P. E. Molloy, S. M. Dunn, Y. Li, M. M. Suhoski, R. G. Carroll, A. Milicic, T. Mahon, D. H. Sutton, B. Laugel, R. Moysey, B. J. Cameron, A. Vuidepot, M. A. Purbhoo, D. K. Cole, R. E. Phillips, C. H. June, B. K. Jakobsen, A. K. Sewell, and J. L. Riley. 2008. Control of HIV-1 immune escape by CD8 T cells expressing enhanced T-cell receptor. *Nat Med* 14:1390-1395.
10. Richman, S. A., and D. M. Kranz. 2007. Display, engineering, and applications of antigen-specific T cell receptors. *Biomol Eng* 24:361-373.
11. Boulter, J. M., M. Glick, P. T. Todorov, E. Baston, M. Sami, P. Rizkallah, and B. K. Jakobsen. 2003. Stable, soluble T-cell receptor molecules for crystallization and therapeutics. *Protein Eng* 16:707-711.
12. Richman, S. A., D. H. Aggen, M. L. Dossett, D. L. Donermeyer, P. M. Allen, P. D. Greenberg, and D. M. Kranz. 2009. Structural features of T cell receptor variable regions that enhance domain stability and enable expression as single-chain ValphaVbeta fragments. *Mol Immunol* 46:902-916.
13. Soo Hoo, W. F., M. J. Lacy, L. K. Denzin, E. W. J. Voss, K. D. Hardman, and D. M. Kranz. 1992. Characterization of a single-chain T cell receptor expressed in *E. Coli*. *Proc. Natl. Acad. Sci.* 89:4759-4763.
14. Novotny, J., R. K. Ganju, S. T. Smiley, R. E. Hussey, M. A. Luther, M. A. Recny, R. F. Siliciano, and E. L. Reinherz. 1991. A soluble, single-chain T-cell receptor fragment endowed with antigen-combing properties. *Proc. Natl. Acad. Sci.* 88:8646-8650.
15. Kieke, M. C., E. V. Shusta, E. T. Boder, L. Teyton, K. D. Wittrup, and D. M. Kranz. 1999. Selection of functional T cell receptor mutants from a yeast surface-display library. *Proc Natl Acad Sci USA* 96:5651-5656.
16. Shusta, E. V., P. D. Holler, M. C. Kieke, D. M. Kranz, and K. D. Wittrup. 2000. Directed evolution of a stable scaffold for T-cell receptor engineering. *Nat Biotechnol* 18:754-759.
17. Zhang, B., Y. Zhang, N. A. Bowerman, A. Schietinger, Y. X. Fu, D. M. Kranz, D. A. Rowley, and H. Schreiber. 2008. Equilibrium between host and cancer caused by effector T cells killing tumor stroma. *Cancer Res* 68:1563-1571.
18. Chervin, A. S., J. D. Stone, P. D. Holler, A. Bai, J. Chen, H. N. Eisen, and D. M. Kranz. 2009. The impact of TCR-binding properties and antigen presentation format on T cell responsiveness. *J Immunol* 183:1166-1178.
19. Sami, M., P. J. Rizkallah, S. Dunn, P. Molloy, R. Moysey, A. Vuidepot, E. Baston, P. Todorov, Y. Li, F. Gao, J. M. Boulter, and B. K. Jakobsen. 2007. Crystal structures of high affinity human T-cell receptors bound to peptide major histocompatibility complex reveal native diagonal binding geometry. *Protein Eng Des Sel* 20:397-403.
20. Shusta, E. V., M. C. Kieke, E. Parke, D. M. Kranz, and K. D. Wittrup. 1999. Yeast polypeptide fusion surface display levels predict thermal stability and soluble secretion efficiency. *J Mol Biol* 292:949-956.

21. Park, S., Y. Xu, X. F. Stowell, F. Gai, J. G. Saven, and E. T. Boder. 2006. Limitations of yeast surface display in engineering proteins of high thermostability. *Protein Eng Des Sel* 19:211-217.
22. Jones, L. L., S. E. Brophy, A. J. Bankovich, L. A. Coif, N. A. Hanick, K. C. Garcia, and D. M. Kranz. 2006. Engineering and characterization of a stabilized alphaI/alpha2 module of the class I major histocompatibility complex product Ld. *J Biol Chem* 281:25734-25744.
23. Dossett, M. L., R. M. Teague, T. M. Schmitt, X. Tan, L. J. Cooper, C. Pinzon, and P. D. Greenberg. 2009. Adoptive immunotherapy of disseminated leukemia with TCR-transduced, CD8+ T cells expressing a known endogenous TCR. *Mol Ther* 17:742-749.
24. Schmitt, T. M., G. B. Ragnarsson, and P. D. Greenberg. 2009. TCR Gene Therapy for Cancer. *Hum Gene Ther.*
25. Zhang, T., X. He, T. C. Tsang, and D. T. Harris. 2004. Transgenic TCR expression: comparison of single chain with full-length receptor constructs for T-cell function. *Cancer Gene Ther* 11:487-496.
26. Kuball, J., M. L. Dossett, M. Wolfl, W. Y. Ho, R. H. Voss, C. Fowler, and P. D. Greenberg. 2007. Facilitating matched pairing and expression of TCR chains introduced into human T cells. *Blood* 109:2331-2338.
27. Cohen, C. J., Y. F. Li, M. El-Gamil, P. F. Robbins, S. A. Rosenberg, and R. A. Morgan. 2007. Enhanced antitumor activity of T cells engineered to express T-cell receptors with a second disulfide bond. *Cancer Res* 67:3898-3903.
28. Sadelain, M., R. Brentjens, and I. Riviere. 2009. The promise and potential pitfalls of chimeric antigen receptors. *Curr Opin Immunol* 21:215-223.
29. Tammana, S., X. Huang, M. Wong, M. C. Milone, L. Ma, B. L. Levine, C. H. June, J. E. Wagner, B. Blazar, and X. Zhou. 2009. 4-1 BB and CD28 Signaling Plays A Synergistic Role in Redirecting Umbilical Cord Blood T Cells Against B-Cell Malignancies. *Hum Gene Ther.*
30. Milone, M. C., J. D. Fish, C. Carpenito, R. G. Carroll, G. K. Binder, D. Teachey, M. Samanta, M. Lakhal, B. Gloss, G. Danet-Desnoyers, D. Campana, J. L. Riley, S. A. Grupp, and C. H. June. 2009. Chimeric receptors containing CD137 signal transduction domains mediate enhanced survival of T cells and increased antileukemic efficacy in vivo. *Mol Ther* 17:1453-1464.
31. Carpenito, C., M. C. Milone, R. Hassan, J. C. Simonet, M. Lakhal, M. M. Suhoski, A. Varela-Rohena, K. M. Haines, D. F. Heitjan, S. M. Albelda, R. G. Carroll, J. L. Riley, I. Pastan, and C. H. June. 2009. Control of large, established tumor xenografts with genetically retargeted human T cells containing CD28 and CD137 domains. *Proc Natl Acad Sci USA* 106:3360-3365.
32. Kochenderfer, J. N., S. A. Feldman, Y. Zhao, H. Xu, M. A. Black, R. A. Morgan, W. H. Wilson, and S. A. Rosenberg. 2009. Construction and preclinical evaluation of an anti-CD19 chimeric antigen receptor. *J Immunother* 32:689-702.
33. Mantovani, S., B. Palermo, S. Garbelli, R. Campanelli, G. Robustelli Della Cuna, R. Gennari, F. Benvenuto, E. Lantelme, and C. Giachino. 2002. Dominant TCR-alpha requirements for a self antigen recognition in humans. *J Immunol* 169:6253-6260.
34. Dietrich, P. Y., F. A. Le Gal, V. Dutoit, M. J. Pittet, L. Trautman, A. Zippelius, I. Cognet, V. Widmer, P. R. Walker, O. Michielin, P. Guillaume, T. Connerotte, F. Jotereau, P. G. Coulie, P. Romero, J. C. Cerottini, M. Bonneville, and D. Valmori. 2003. Prevalent role of TCR alpha-chain in the selection of the preimmune repertoire specific for a human tumor-associated self-antigen. *J Immunol* 170:5103-5109.
35. de Witte, M. A., A. Jorritsma, A. Kaiser, M. D. van den Boom, M. Dokter, G. M. Bendle, J. B. Haanen, and T. N. Schumacher. 2008. Requirements for effective antitumor responses of TCR transduced T cells. *J Immunol* 181:5128-5136.
36. Heemskerk, M. H., R. S. Hagedoorn, M. A. van der Hoorn, L. T. van der Veken, M. Hoogeboom, M. G. Kester, R. Willemze, and J. H. Falkenburg. 2007. Efficiency of T-cell receptor expression in dual-specific T cells is controlled by the intrinsic qualities of the TCR chains within the TCR-CD3 complex. *Blood* 109:235-243.
37. Hart, D. P., S. A. Xue, S. Thomas, M. Cesco-Gaspere, A. Tranter, B. Willcox, S. P. Lee, N. Steven, E. C. Morris, and H. J. Stauss. 2008. Retroviral transfer of a dominant TCR prevents surface expression of a large proportion of the endogenous TCR repertoire in human T cells. *Gene Ther* 15:625-631.
38. Sommermeyer, D., J. Neudorfer, M. Weinhold, M. Leisegang, B. Engels, E. Noessner, M. H. Heemskerk, J. Charo, D. J. Schendel, T. Blankenstein, H. Bernhard, and W. Uckert. 2006. Designer T cells by T cell receptor replacement. *Eur J Immunol* 36:3052-3059.
39. Martinez-Hackert, E., N. Anikeeva, S. A. Kalams, B. D. Walker, W. A. Hendrickson, and Y. Sykulev. 2006. Structural basis for degenerate recognition of natural HIV peptide variants by cytotoxic lymphocytes. *J Biol Chem* 281:20205-20212.
40. Turnbull, E. L., A. R. Lopes, N. A. Jones, D. Cornforth, P. Newton, D. Aldam, P. Pellegrino, J. Turner, I. Williams, C. M. Wilson, P. A. Goepfert, M. K. Maini, and P. Borrow. 2006. HIV-1 epitope-specific CD8+ T cell responses strongly associated with delayed disease progression cross-recognize epitope variants efficiently. *J Immunol* 176:6130-6146.
41. Anikeeva, N., T. Mareeva, W. Liu, and Y. Sykulev. 2009. Can oligomeric T-cell receptor be used as a tool to detect viral peptide epitopes on infected cells? *Clin Immunol* 130:98-109.
42. Garboczi, D. N., P. Ghosh, U. Utz, Q. R. Fan, W. E. Biddison, and D. C. Wiley. 1996. Structure of the complex between human T-cell receptor, viral peptide and HLA-A2. *Nature* 384:134-141.
43. Richman, S. A., D. M. Kranz, and J. D. Stone. 2009. Biosensor detection systems: engineering stable, high-affinity bioreceptors by yeast surface display. *Methods Mol Biol* 504:323-350.
44. Boder, E. T., and K. D. Wittrup. 2000. Yeast surface display for directed evolution of protein expression, affinity, and stability. *Methods Enzymol* 328:430-444.
45. Warrens, A. N., M. D. Jones, and R. I. Lechler. 1997. Splicing by overlap extension by PCR using asymmetric amplification: an improved technique for the generation of hybrid proteins of immunological interest. *Gene* 186:29-35.
46. Garcia, K. C., C. G. Radu, J. Ho, R. J. Ober, and E. S. Ward. 2001. Kinetics and thermodynamics of T cell receptor-autoantigen interactions in murine experimental autoimmune encephalomyelitis. *Proc Natl Acad Sci USA* 98:6818-6823.

U.S. Pat. No. 6,759,243

Richman, Kranz, 2007, Display, engineering, and applications of antigen-specific T cell receptors, Biomolecular Engineering 24, 361-373

Kieke, et al., 1999, Selection of functional T cell receptor mutants from a yeast surface-display library, Proc. Natl. Acad. Sci. USA, 96, 5651-5656

Richman, et al., 2009, Structural features of T cell receptor variable regions that enhance domain stability and enable expression as single-chain VαVβ fragments, Molecular Immunology, 46, 902-916 7569664

EP 0552142 (Connetics Corporation)

EP 1188825 (Universiteit Leiden)

WO98/39482 PCT/US98/04274(Sunol Molecular Corporation)

US publication 2007/0116718 (Weidanz)

U.S. Pat. No. 7,456,263 (Sherman)

US publication 2006/0166875 (Jakobsen)

U.S. Pat. No. 7,462,486 (Vandenbark)

US 2009/0208502 (Willemsen)

US publication 2003/0144474 (Weidanz)

Neves, Amino acids specifying MHC class preference in TCR V alpha 2 regions. J. Immunol. 1999: 163, 5471-7.

WO00/31239 (Yeda Research and Development Co., Ltd).

Hilyard. 1994. Binding of soluble natural ligands to a soluble human T-cell receptor fragment produced in *Escherichia coli*. Proc. Natl. Acad. Sci. USA. 91:9057-9061.

US2004/0137457

We claim:

1. A soluble human single-chain T cell receptor (TCR) having the structure:
Vα2-L-Vβ or Vβ-L-Vα2, wherein L is a linker peptide that links Vβ with Vα, Vβ is a TCR variable β region, and Vα2 is a TCR variable α region of family 2, wherein the single-chain TCR does not contain a TCR constant domain, wherein the Vα2 comprises a serine mutation at the position corresponding to position 49 of SEQ ID NO: 43 and wherein the Vα2 comprises an amino acid sequence that is at least 95% identical to the amino acid sequence of SEQ ID NO. 43.

2. The TCR of claim 1, wherein the serine mutation at position 49 is a phenylalanine to a serine.

3. The TCR of claim 1, further comprising one or more mutations in CDR2β or CDR3α.

4. The TCR of claim 1, wherein the linker peptide contains more than 5 lysine residues.

5. The TCR of claim 1, wherein the linker peptide contains between 10 and 30 amino acids.

6. The TCR of claim 1, wherein the linker peptide is GSADDAKKDAAKKDGKS (SEQ ID NO: 4).

7. The TCR of claim 1, wherein the TCR specifically binds a ligand comprising a peptide known as SL9 (SEQ ID NO: 2) from the HIV Gag protein.

8. The TCR of claim 7 that has the sequence of the Vα (SEQ ID NO: 59) and Vβ (SEQ ID NO:53) regions from the scTCR known as 868-Z11.

9. The TCR of claim 1, further comprising a biologically active group.

10. The TCR of claim 9, wherein the biologically active group is selected from: an anti-inflammatory group, an anti-tumor agent, a cytokine, a radioisotope, a toxin, or an antibody such as a single-chain Fv.

11. The TCR of claim 9, wherein the biologically active group is a cytotoxic molecule.

12. The TCR of claim 1, further comprising a detectable group.

13. The TCR of claim 12, wherein the detectable group can be detected by spectroscopic or enzyme-based methods.

14. The TCR of claim 12, wherein the detectable group is a fluorescent group, a radiolabeled group, an absorbing group, or an enzyme with properties that generate detectable products.

15. The TCR of claim 9, wherein the biologically active group is bound to the single-chain TCR through a linker.

16. A method for producing single-chain T cell receptors comprising expressing a single-chain TCR of claim 1 in *E. coli*.

17. A pharmaceutical composition comprising the TCR of claim 1 and a pharmaceutically acceptable carrier.

18. The TCR of claim 1 which has been linked to signaling domains that yields an active TCR on the surface of a T cell.

* * * * *

UNITED STATES PATENT AND TRADEMARK OFFICE
CERTIFICATE OF CORRECTION

| | |
|---|---|
| PATENT NO. | : 10,464,987 B2 |
| APPLICATION NO. | : 13/500123 |
| DATED | : November 5, 2019 |
| INVENTOR(S) | : David M. Kranz and David H. Aggen |

It is certified that error appears in the above-identified patent and that said Letters Patent is hereby corrected as shown below:

On the Title Page

Item (74), "Womble Bond Dickson (US) LLP" should read as --Womble Bond Dickinson (US) LLP--.

Signed and Sealed this
Seventh Day of June, 2022

Katherine Kelly Vidal
*Director of the United States Patent and Trademark Office*

```
                        SEQUENCE LISTING

<160> NUMBER OF SEQ ID NOS: 61

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Leu Leu Phe Gly Tyr Pro Val Tyr Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Ser Leu Tyr Asn Thr Val Ala Thr Leu
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic construct

<400> SEQUENCE: 3

Gly Gly Gly Ser
1

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Gly Ser Ala Asp Asp Ala Lys Lys Asp Ala Ala Lys Lys Asp Gly Lys
1               5                   10                  15

Ser

<210> SEQ ID NO 5
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 5

Ser Leu Leu Met Trp Ile Thr Asn Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Arg Met Phe Pro Asn Ala Pro Tyr Leu
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic construct

<400> SEQUENCE: 7

Tyr Val Arg Gly Glu Glu
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic construct

<400> SEQUENCE: 8

Cys Ala Val Arg Gly Ala His Asp Tyr Ala Leu Asn
1               5                   10

<210> SEQ ID NO 9
<211> LENGTH: 52
<212> TYPE: DNA
<213> ORGANISM: Artificial Sequence
<220> FEATURE:
<223> OTHER INFORMATION: Synthetic construct

<400> SEQUENCE: 9
ggtaaatctc cagaattgat catgtccatc tactctaatg gtgacaaaga ag          52

<210> SEQ ID NO 10
<211> LENGTH: 52
<212> TYPE: DNA
<213> ORGANISM: Artificial Sequence
<220> FEATURE:
<223> OTHER INFORMATION: Synthetic construct

<400> SEQUENCE: 10
cttctttgtc accattagag tagatggaca tgatcaattc tggagattta cc          52

<210> SEQ ID NO 11
<211> LENGTH: 6
<212> TYPE: PRT
<213> ORGANISM: Artificial Sequence
<220> FEATURE:
<223> OTHER INFORMATION: Synthetic construct

<400> SEQUENCE: 11

Tyr Tyr Glu Glu Glu Glu
1               5

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Cys Ala Val Arg Thr Asn Ser Gly Tyr Ala Leu Asn Phe Gly
1               5                   10

<210> SEQ ID NO 13
<211> LENGTH: 86
<212> TYPE: DNA
<213> ORGANISM: Artificial Sequence
<220> FEATURE:
<223> OTHER INFORMATION: Synthetic construct

<400> SEQUENCE: 13
tataccatgg gcagcagcca tcatcatcat catcacagca gcggcctggt gccgcgcggc      60
agcgaagctg gtgttactca atctcc                                          86

<210> SEQ ID NO 14
<211> LENGTH: 43
<212> TYPE: DNA
<213> ORGANISM: Artificial Sequence
<220> FEATURE:
<223> OTHER INFORMATION: Synthetic construct

<400> SEQUENCE: 14
aaatgaattc ttaaatatgt ggagtaaccc aaaaagaagt acc                        43

<210> SEQ ID NO 15
<211> LENGTH: 5
<212> TYPE: PRT
<213> ORGANISM: Artificial Sequence
<220> FEATURE:
<223> OTHER INFORMATION: Synthetic construct

<400> SEQUENCE: 15

Leu His Arg Pro Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic construct

<400> SEQUENCE: 16

Gly Phe Ala Ser Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic construct

<400> SEQUENCE: 17

Ser Ile Tyr Arg Tyr Tyr Gly Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic construct

<400> SEQUENCE: 18

Ser Ile Ile Asn Phe Glu Lys Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic construct

<400> SEQUENCE: 19

Ser Leu Tyr Asn Thr Val Ala Thr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Arg Met Phe Pro Asn Ala Pro Tyr Leu
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic construct

<400> SEQUENCE: 21

Ile Gln Ser Ser Gln
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic construct

<400> SEQUENCE: 22

Pro Thr Ser Gly Gly Ser Tyr Ile Pro Thr
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic construct

<400> SEQUENCE: 23

Val Gly Ala Gly Ile

<210> SEQ ID NO 24
<211> LENGTH: 11
<212> TYPE: PRT
<213> ORGANISM: Artificial Sequence
<220> FEATURE:
<223> OTHER INFORMATION: Synthetic construct

<400> SEQUENCE: 24

Ser Ser Tyr Val Gly Asn Thr Gly Glu Leu Phe
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic construct

<400> SEQUENCE: 25

Ile Pro Phe Trp Gln
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic construct

<400> SEQUENCE: 26

Val Ser Val Gly Met
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic construct

<400> SEQUENCE: 27

Ser Ile Tyr Ser Asn Gly
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic construct

<400> SEQUENCE: 28

Val Thr Thr Asp Ser Trp Gly Lys Leu Gln
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Synthetic construct

<400> SEQUENCE: 29

Ser Val Gly Ala Gly Ile
1               5

<210> SEQ ID NO 30
<211> LENGTH: 12
<212> TYPE: PRT
<213> ORGANISM: Artificial Sequence
<220> FEATURE:
<223> OTHER INFORMATION: Synthetic construct

<400> SEQUENCE: 30

Arg Pro Gly Leu Ala Gly Gly Arg Pro Glu Leu Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic construct

<400> SEQUENCE: 31

Arg Pro Gly Leu Met Ser Ala Gln Pro Glu Leu Tyr
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Synthetic construct

<400> SEQUENCE: 32

Phe Ile Tyr Ser Asn Gly
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct

<400> SEQUENCE: 33

Val Arg Thr Asn Ser Gly Tyr Ala Leu Asn
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Synthetic construct

<400> SEQUENCE: 34

Tyr Tyr Glu Glu Glu Glu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic construct

<400> SEQUENCE: 35

Ser Asp Thr Val Ser Tyr Glu Gln Tyr
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic construct

<400> SEQUENCE: 36

Val Arg Gly Ala His Asp Tyr Ala Leu Asn
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Synthetic construct

<400> SEQUENCE: 37

Tyr Val Arg Gly Glu Glu
1               5

<210> SEQ ID NO 38
<211> LENGTH: 116
<212> TYPE: PRT
<213> ORGANISM: Artificial Sequence
<220> FEATURE:
<223> OTHER INFORMATION: Synthetic construct

<400> SEQUENCE: 38

Gly Val Thr Gln Thr Pro Lys Phe Gln Val Leu Lys Thr Gly Gln Ser
1               5                   10                  15

Met Thr Leu Gln Cys Ala Gln Asp Met Asn His Glu Tyr Met Ser Trp
            20                  25                  30

Tyr Arg Gln Asp Pro Gly Met Gly Leu Arg Leu Ile His Tyr Ser Val
        35                  40                  45

Ser Val Gly Met Thr Asp Gln Gly Glu Val Pro Asn Gly Tyr Asn Val
    50                  55                  60

Ser Arg Ser Thr Thr Glu Asp Phe Pro Leu Arg Leu Leu Ser Ala Ala
65                  70                  75                  80

Pro Ser Gln Thr Ser Val Tyr Phe Cys Ala Ser Ser Tyr Val Gly Asn
                85                  90                  95

Thr Gly Glu Leu Phe Phe Gly Glu Gly Ser Arg Leu Thr Val Leu Glu
            100                 105                 110

Asp Leu Lys Asn
        115

<210> SEQ ID NO 39
<211> LENGTH: 120
<212> TYPE: PRT
<213> ORGANISM: Artificial Sequence
<220> FEATURE:
<223> OTHER INFORMATION: Synthetic construct

<400> SEQUENCE: 39

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

```
Ser Val Gly Ala Gly Ile Thr Asp Gln Gly Glu Val Pro Asn Gly Tyr
 50                  55                  60
Asn Val Ser Arg Ser Thr Thr Glu Asp Phe Pro Leu Arg Leu Leu Ser
 65                  70                  75                  80
Ala Ala Pro Ser Gln Thr Ser Val Tyr Phe Cys Ala Ser Arg Pro Gly
                 85                  90                  95
Leu Met Ser Ala Gln Pro Glu Gln Tyr Phe Gly Pro Gly Thr Arg Leu
                100                 105                 110
Thr Val Thr Glu Asp Leu Lys Asn
            115                 120

<210> SEQ ID NO 40
<211> LENGTH: 117
<212> TYPE: PRT
<213> ORGANISM: Artificial Sequence
<220> FEATURE:
<223> OTHER INFORMATION: Synthetic construct

<400> SEQUENCE: 40

Glu Ala Gly Val Thr Gln Ser Pro Thr His Leu Ile Lys Thr Arg Gly
  1               5                  10                  15
Gln Gln Val Thr Leu Arg Cys Ser Pro Lys Ser Gly His Asp Thr Val
                 20                  25                  30
Ser Trp Tyr Gln Gln Ala Leu Gly Gln Gly Pro Gln Phe Ile Phe Gln
             35                  40                  45
Tyr Val Arg Gly Glu Glu Arg Gln Arg Gly Asn Phe Pro Asp Arg Phe
 50                  55                  60
Ser Gly His Gln Phe Pro Asn Tyr Ser Ser Glu Leu Asn Val Asn Ala
 65                  70                  75                  80
Leu Leu Leu Gly Asp Ser Ala Leu Tyr Leu Cys Ala Ser Ser Asp Thr
                 85                  90                  95
Val Ser Tyr Glu Gln Tyr Phe Gly Pro Gly Thr Arg Leu Thr Val Thr
                100                 105                 110
Glu Asp Leu Lys Asn
            115

<210> SEQ ID NO 41
<211> LENGTH: 115
<212> TYPE: PRT
<213> ORGANISM: Artificial Sequence
<220> FEATURE:
<223> OTHER INFORMATION: Synthetic construct

<400> SEQUENCE: 41

Lys Gln Glu Val Thr Gln Ile Pro Ala Ala Leu Ser Val Pro Glu Gly
  1               5                  10                  15
Glu Asn Leu Val Leu Asn Cys Ser Phe Thr Asp Ser Ala Ile Tyr Asn
                 20                  25                  30
Leu Gln Trp Phe Arg Gln Asp Pro Gly Lys Gly Leu Thr Ser Leu Leu
             35                  40                  45
Leu Ile Pro Phe Trp Gln Arg Glu Gln Thr Ser Gly Arg Leu Asn Ala
 50                  55                  60
Ser Leu Asp Lys Ser Ser Gly Thr Ser Thr Leu Tyr Ile Ala Ala Ser
 65                  70                  75                  80
Gln Pro Gly Asp Ser Ala Thr Tyr Leu Cys Ala Val Arg Pro Thr Ser
                 85                  90                  95
Gly Gly Ser Tyr Ile Pro Thr Phe Gly Arg Gly Thr Ser Leu Ile Val
                100                 105                 110
```

-continued

His Pro Tyr
        115

<210> SEQ ID NO 42
<211> LENGTH: 112
<212> TYPE: PRT
<213> ORGANISM: Artificial Sequence
<220> FEATURE:
<223> OTHER INFORMATION: Synthetic construct

<400> SEQUENCE: 42

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Thr Thr Asp Ser Trp
                85                  90                  95

Gly Lys Leu Gln Phe Gly Ala Gly Thr Gln Val Val Thr Pro Asp
            100                 105                 110

<210> SEQ ID NO 43
<211> LENGTH: 113
<212> TYPE: PRT
<213> ORGANISM: Artificial Sequence
<220> FEATURE:
<223> OTHER INFORMATION: Synthetic construct

<400> SEQUENCE: 43

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile

<210> SEQ ID NO 44
<211> LENGTH: 89
<212> TYPE: PRT
<213> ORGANISM: Artificial Sequence
<220> FEATURE:
<223> OTHER INFORMATION: Synthetic construct

<400> SEQUENCE: 44

Gln Lys Glu Val Glu Gln Asn Ser Gly Pro Leu Ser Val Pro Glu Gly

```
                1               5                   10                  15
Ala Ile Ala Ser Leu Asn Cys Thr Tyr Ser Asp Arg Gly Ser Gln Ser
                20                  25                  30

Phe Phe Trp Tyr Arg Gln Tyr Ser Gly Lys Ser Pro Glu Leu Ile Met
            35                  40                  45

Phe Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys
                85
```

<210> SEQ ID NO 45
<211> LENGTH: 88
<212> TYPE: PRT
<213> ORGANISM: Artificial Sequence
<220> FEATURE:
<223> OTHER INFORMATION: Synthetic construct

<400> SEQUENCE: 45

```
Arg Lys Glu Val Glu Gln Asp Pro Gly Pro Phe Asn Val Pro Glu Gly
1               5                   10                  15

Ala Thr Val Ala Phe Asn Cys Thr Tyr Ser Asn Ser Ala Ser Gln Ser
                20                  25                  30

Phe Phe Trp Tyr Arg Gln Asp Cys Arg Lys Glu Pro Lys Leu Leu Met
            35                  40                  45

Ser Val Tyr Ser Ser Gly Asn Glu Asp Gly Arg Phe Thr Ala Gln Leu
        50                  55                  60

Asn Arg Ala Ser Gln Tyr Ile Ser Leu Leu Ile Arg Asp Ser Lys Leu
65                  70                  75                  80

Ser Asp Ser Ala Thr Tyr Leu Cys
                85
```

<210> SEQ ID NO 46
<211> LENGTH: 4
<212> TYPE: PRT
<213> ORGANISM: Artificial Sequence
<220> FEATURE:
<223> OTHER INFORMATION: Synthetic construct

<400> SEQUENCE: 46

```
Thr Asn Ser Gly
1
```

<210> SEQ ID NO 47
<211> LENGTH: 4
<212> TYPE: PRT
<213> ORGANISM: Artificial Sequence
<220> FEATURE:
<223> OTHER INFORMATION: Synthetic construct

<400> SEQUENCE: 47

```
Gly Ala His Asp
1
```

<210> SEQ ID NO 48
<211> LENGTH: 120
<212> TYPE: PRT
<213> ORGANISM: Artificial Sequence
<220> FEATURE:
<223> OTHER INFORMATION: scTCR Sequence -continued

```
<400> SEQUENCE: 48

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Ala Gly Gly Arg Pro Glu Gln Tyr Phe Gly Pro Gly Thr Arg Leu
            100                 105                 110

Thr Val Thr Glu Asp Leu Lys Asn
        115                 120

<210> SEQ ID NO 49
<211> LENGTH: 120
<212> TYPE: PRT
<213> ORGANISM: Artificial Sequence
<220> FEATURE:
<223> OTHER INFORMATION: scTCR sequence

<400> SEQUENCE: 49

Asn Ala Gly Val Thr Gln Thr Pro Lys Phe Leu Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Val Gly Ile Thr Asp Gln Gly Glu Val Pro Asp Gly Tyr
    50                  55                  60

Lys Val Cys Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Arg Asn
        115                 120

<210> SEQ ID NO 50
<211> LENGTH: 120
<212> TYPE: PRT
<213> ORGANISM: Artificial sequence
<220> FEATURE:
<223> OTHER INFORMATION: scTCR sequence

<400> SEQUENCE: 50

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45
```

```
Ser Val Gly Val Gly Ile Thr Asp Gln Gly Asp Val Pro Asp Gly Tyr
    50              55                  60
Lys Val Ser Arg Ser Thr Thr Glu Asp Phe Pro Leu Arg Leu Leu Ser
65              70                  75                  80
Ala Ala Pro Ser Gln Thr Ser Val Tyr Phe Cys Ala Ser Arg Pro Gly
                85                  90                  95
Leu Met Ser Ala Gln Pro Glu Leu Tyr Phe Gly Pro Gly Thr Arg Leu
            100                 105                 110
Thr Val Thr Glu Asp Leu Ile Asn
            115                 120
```

<210> SEQ ID NO 51
<211> LENGTH: 112
<212> TYPE: PRT
<213> ORGANISM: Artificial Sequence
<220> FEATURE:
<223> OTHER INFORMATION: scTCR sequence

<400> SEQUENCE: 51

```
Gln Lys Glu Val Glu Gln Asn Pro Gly Pro Leu Ser Val Pro Glu Gly
1               5                   10                  15
Ala Ile Ala Ser Leu Asn Cys Thr Tyr Ser Asp Arg Gly Ser Gln Ser
            20                  25                  30
Phe Phe Trp Tyr Arg Gln Tyr Ser Gly Lys Ser Pro Glu Leu Ile Met
        35                  40                  45
Ser Ile Tyr Ser Asn Gly Asp Lys Glu Asp Gly Arg Phe Thr Ala Gln
    50              55                  60
Leu Asp Lys Ala Ser Gln Tyr Val Ser Leu Leu Ile Arg Asp Ser Gln
65              70                  75                  80
Pro Ser Asp Ser Ala Thr Tyr Leu Cys Ala Val Thr Thr Asp Ser Trp
                85                  90                  95
Gly Lys Leu Gln Phe Gly Ala Gly Thr Gln Val Val Val Thr Pro Asp
            100                 105                 110
```

<210> SEQ ID NO 52
<211> LENGTH: 117
<212> TYPE: PRT
<213> ORGANISM: Artificial Sequence
<220> FEATURE:
<223> OTHER INFORMATION: scTCR sequence

<400> SEQUENCE: 52

```
Glu Ala Gly Val Thr Gln Ser Pro Thr His Leu Ile Lys Thr Arg Gly
1               5                   10                  15
Gln Gln Val Thr Leu Arg Cys Ser Pro Lys Ser Gly His Asp Thr Val
            20                  25                  30
Ser Trp Tyr Gln Gln Ala Leu Gly Gln Gly Pro Gln Phe Ile Phe Gln
        35                  40                  45
Tyr Tyr Glu Glu Glu Glu Arg Gln Arg Gly Asn Phe Pro Asp Arg Phe
    50              55                  60
Ser Gly His Gln Phe Pro Asn Tyr Ser Ser Glu Leu Asn Val Asn Ala
65              70                  75                  80
Leu Leu Leu Gly Asp Ser Ala Leu Tyr Leu Cys Ala Ser Ser Asp Thr
                85                  90                  95
Val Ser Tyr Glu Gln Tyr Phe Gly Pro Gly Thr Arg Leu Thr Val Thr
            100                 105                 110
Glu Asp Leu Lys Asn
            115
```

<210> SEQ ID NO 53
<211> LENGTH: 117
<212> TYPE: PRT
<213> ORGANISM: Artificial Sequence
<220> FEATURE:
<223> OTHER INFORMATION: scTCR sequence

<400> SEQUENCE: 53

```
Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Tyr Pro Asn Tyr Ser Ser Glu Leu Asn Ile Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Ile Arg Leu Thr Val Thr
            100                 105                 110

Glu Asp Leu Lys Asn
        115
```

<210> SEQ ID NO 54
<211> LENGTH: 117
<212> TYPE: PRT
<213> ORGANISM: Artificial Sequence
<220> FEATURE:
<223> OTHER INFORMATION: scTCR sequence

<400> SEQUENCE: 54

```
Glu Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Val Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Gly Thr Arg Leu Thr Val Thr
            100                 105                 110

Glu Asp Leu Lys Asn
        115
```

<210> SEQ ID NO 55
<211> LENGTH: 117
<212> TYPE: PRT
<213> ORGANISM: Artificial Sequence
<220> FEATURE:
<223> OTHER INFORMATION: scTCR sequence

<400> SEQUENCE: 55

Glu Ala Gly Val Ile Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Arg Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Asp Thr
                85                  90                  95

Val Ser Tyr Glu Gln Tyr Phe Gly Pro Ser Thr Arg Leu Thr Val Thr
            100                 105                 110

Glu Asp Leu Lys Asn
            115

<210> SEQ ID NO 56
<211> LENGTH: 117
<212> TYPE: PRT
<213> ORGANISM: Artificial Sequence
<220> FEATURE:
<223> OTHER INFORMATION: scTCR sequence

<400> SEQUENCE: 56

Glu Ala Gly Val Thr Gln Ser Pro Thr His Leu Ile Lys Thr Arg Gly
1               5                   10                  15

Gln Gln Val Thr Leu Arg Cys Ser Phe Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Val Arg Gly Glu Glu Arg Gln Arg Gly Asn Phe Pro Asp Arg Phe
    50                  55                  60

Ser Gly His Gln Phe Ser Asn Tyr Ser Ser Glu Leu Asn Val Asn Ala
65                  70                  75                  80

Leu Leu Leu Asp Asp Ser Ala Leu Tyr Leu Cys Ala Ser Ser Asp Thr
                85                  90                  95

Val Ser Tyr Glu Gln Tyr Phe Gly Pro Gly Thr Arg Leu Thr Val Thr
            100                 105                 110

Glu Asp Leu Lys Asn
            115

<210> SEQ ID NO 57
<211> LENGTH: 113
<212> TYPE: PRT
<213> ORGANISM: Artificial Sequence
<220> FEATURE:
<223> OTHER INFORMATION: scTCR sequence

<400> SEQUENCE: 57

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Thr Asn Ser Gly
                85                  90                  95

Tyr Ala Leu Asn Phe Gly Lys Gly Thr Ser Leu Leu Val Thr Pro His
            100                 105                 110

Ile

<210> SEQ ID NO 58
<211> LENGTH: 113
<212> TYPE: PRT
<213> ORGANISM: Artificial Sequence
<220> FEATURE:
<223> OTHER INFORMATION: scTCR sequence

<400> SEQUENCE: 58

Gln Lys Glu Val Glu Gln Asn Ser Gly Pro Leu Ser Val Pro Glu Gly
1               5                   10                  15

Ala Thr Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Met Val Thr Pro His
            100                 105                 110

Ile

<210> SEQ ID NO 59
<211> LENGTH: 113
<212> TYPE: PRT
<213> ORGANISM: Artificial Sequence
<220> FEATURE:
<223> OTHER INFORMATION: scTCR sequence

<400> SEQUENCE: 59

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Lys Gly Thr Ser Leu Leu Val Thr Pro His
            100                 105                 110

Ile

```
<210> SEQ ID NO 60
<211> LENGTH: 113
<212> TYPE: PRT
<213> ORGANISM: Artificial Sequence
<220> FEATURE:
<223> OTHER INFORMATION: scTCR sequence

<400> SEQUENCE: 60

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Ile Ser Leu Leu Ile Arg Asp Ser Lys
65                  70                  75                  80

Leu Ser Asp Ser Ala Thr Tyr Leu Cys Ala Val Arg Gly Ala His Asp
                85                  90                  95

Tyr Ala Leu Asn Phe Gly Arg Gly Thr Ser Leu Leu Val Thr Pro His
            100                 105                 110

Ile

<210> SEQ ID NO 61
<211> LENGTH: 10
<212> TYPE: PRT
<213> ORGANISM: Homo sapiens

<400> SEQUENCE: 61

Glu Leu Ala Gly Ile Gly Ile Leu Thr Val
1               5                   10
```